United States Patent
Agrawal et al.

(10) Patent No.: US 11,419,904 B2
(45) Date of Patent: Aug. 23, 2022

(54) IMMUNOMODULATORY COMPOSITIONS AND METHODS OF USE THEREOF

(71) Applicants: Babita Agrawal, Edmonton (CA); Rakesh Kumar, Edmonton (CA); Nancy Gupta, Edmonton (CA)

(72) Inventors: Babita Agrawal, Edmonton (CA); Rakesh Kumar, Edmonton (CA); Nancy Gupta, Edmonton (CA)

(*) Notice: Subject to any disclaimer, the term of this patent is extended or adjusted under 35 U.S.C. 154(b) by 0 days.

(21) Appl. No.: 17/372,614

(22) Filed: Jul. 12, 2021

(65) Prior Publication Data
US 2021/0369792 A1 Dec. 2, 2021

Related U.S. Application Data

(62) Division of application No. 15/754,580, filed as application No. PCT/IB2016/055016 on Aug. 22, 2016, now Pat. No. 11,065,283.

(60) Provisional application No. 62/209,693, filed on Aug. 25, 2015.

(51) Int. Cl.
| | |
|---|---|
| A61K 39/02 | (2006.01) |
| A61K 35/74 | (2015.01) |
| A61P 37/06 | (2006.01) |
| A61K 45/06 | (2006.01) |

(52) U.S. Cl.
CPC .......... *A61K 35/74* (2013.01); *A61K 45/06* (2013.01); *A61P 37/06* (2018.01)

(58) Field of Classification Search
None
See application file for complete search history.

(56) References Cited

U.S. PATENT DOCUMENTS 6,368,599 B1 * 4/2002 Langermann .......... A61P 37/04
424/283.1

FOREIGN PATENT DOCUMENTS

| CA | 2935511 A1 | 7/2015 |
|---|---|---|
| WO | 2015104656 A1 | 7/2015 |

OTHER PUBLICATIONS

Declaration under 35 USC 1.132 by inventor Babita Agrawal submitted in parent U.S. Appl. No. 15/7654,580 on Feb. 8, 2021.*
International Search Report and Written Opinion issued in PCT/IB2016/055016 dated Nov. 18, 2016.
Bhatnagar, P.K. et al., Anti-tumor effects of the bacterium caulobacteur crescentus in murine tumor models, Cancel Biology & Therapy, vol. 5, No. 5, May 1, 2006, pp. 485-491.
Partial Supplementary European Search Report dated Mar. 7, 2019 for European application No. 16838643.1.
Ash, K. et al., A comparison fo the Caulobacter NA 1000 and K31 genomes reveals extensive genome rearrangements and differences in metabolic potential, Open Biology, The Royal Society Publishing, vol. 4, No. 10, Sep. 30, 2014.
Presley, G.N. et al., Extracellular gluco-oligosaccharide degradation by Caulobacter crescentus, Microbiology, vol. 160, pp. 635-645, 2014.
Supplementary European Search Report issued in corresponding European application No. 16838643 dated Jun. 6, 2019.

* cited by examiner

*Primary Examiner* — Jennifer E Graser
(74) *Attorney, Agent, or Firm* — BCF LLP

(57) ABSTRACT

The present disclosure provides immunomodulatory compositions comprising live *Caulobacter crescentus* (CC). Immunomodulatory compositions of the present disclosure are useful for modulating an immune response in an individual. The present disclosure thus provides methods of modulating an immune response in an individual, involving administering an immunomodulatory composition comprising live CC to the individual.

6 Claims, 30 Drawing Sheets

Oral treatment with CC leads to reduced inflammatory cytokine production from LPS-stimulated mesenteric lymph nodes Oral treatment with CC leads to enhancement in IL-10 producing $CD4^+$ and $CD8^+$ T cells in spleen Treatment with CC protects mice from LPS-induced liver damage LPS challenged: Treated orally 2x with CC-1

LPS challenged: Treated orally 2x with CC-2

LPS challenged: Control

Normal mouse liver

Modulation of cytokines upon oral treatment with CC in psoriasis afflicted mice

Oral treatment with CC reduces pro-inflammatory cytokines and chemokines in colon tissue of DSS-induced IBD afflicted mice Oral treatment with CC suppresses auto-antigen specific T cell and antibody responses in experimental autoimmune encephalomyelitis (EAE) model Oral treatment with CC suppresses the levels of allergen (OVA) specific IgE in serum and lung washes in an ovalbumin induced airway inflammation model Oral treatment with CC reduces allergen (OVA)-specific cytokines (IL-4 and IL-6) in spleen in murine model Oral treatment with CC in combination with dexamethasone (DEX) provides enhanced reduction in IL-4 and IL-6 levels in spleen in OVA-induced allergic airway inflammation model, compared to DEX alone Oral treatment with CC reduces the production of the pro-inflammatory cytokines in liver of high-fat diet fed mice Oral treatment with CC inhibits pro-inflammatory cytokines in spleen of diet-induced obese mice Oral treatment with CC exhibits positive benefits on serum biochemical markers of metabolic diseases in diet-induced obesity model Oral treatment with CC improves glucose tolerance in high-fat diet fed mice Oral treatment with CC reduces cyclophosphamide associated nephro- and hepato-toxicities in EL-4 lymphoma-bearing C57bl/6 mice Oral treatment with CC reduces cisplatin associated nephro- and hepato-toxicities in B16 metastatic cancer model Oral treatment with CC reduces anti-PD1 monoclonal antibody associated hepatotoxicity in B16 tumor bearing C57bl/6 mice CC modulates human dendritic cells (DCs) *ex vivo*

CC leads to differentiation/expansion of pluripotent stem cells (HSC, CD34$^+$) from human PBMCs into myeloid cells

| Groups | Total CD34$^+$CD45$^-$ | CD34$^+$CD45$^-$ CD11c$^+$ | CD34$^+$CD45$^-$ CD11b$^Á$ |
|---|---|---|---|
| CC, 500x10$^6$/ml | 1.3 | 14 | 11.2 |
| CC, 50x10$^6$/ml | 1.3 | 10.7 | 13.2 |
| CC, 10x10$^6$/ml | 0.9 | 7.2 | 7.2 |
| CC, 1x10$^6$/ml | 0.9 | 2 | 0.7 |
| Saline | 0.9 | 1.2 | 2 |

Figure 30

IMMUNOMODULATORY COMPOSITIONS AND METHODS OF USE THEREOF

CROSS-REFERENCE TO RELATED APPLICATIONS

This application is a division of U.S. application Ser. No. 15/754,580, filed Feb. 22, 2018, which is a national phase filing under 35 U.S.C. 371 of International Application No. PCT/IB2016/055016, filed Aug. 22, 2016, which claims the benefit of U.S. Provisional Patent Application No. 62/209,693, filed Aug. 25, 2015. The contents of the aforementioned applications are incorporated by reference in their entirety herein.

INTRODUCTION

*Caulobacter crescentus* is non-pathogenic, harmless, aquatic, gram-negative bacterium that grows at ~23° C. in many soil and freshwater environments *Caulobacter* has been studied for nearly 50 years. The main laboratory strain (*C. crescentus* CB15) is well characterized genetically and biochemically, and the genome of *C. crescentus* has been sequenced. Caulobacters are readily grown using standard laboratory equipment. They can also be easily grown in commercial fermenters to at least 30 optical density units (ODs) in animal protein free, defined minimal media.

There is a need in the art for immunomodulatory compositions that can be used in the prophylaxis and/or treatment of disorders such as inflammation, undesirable inflammatory activity, exacerbated immune responses, aberrant immune responses, immune dysregulation and autoimmune diseases.

SUMMARY

The present disclosure provides immunomodulatory compositions comprising *Caulobacter crescentus* (CC). Immunomodulatory compositions of the present disclosure are useful for modulating an immune response in an individual. The present disclosure provides methods of modulating an immune response in an individual, involving administering an immunomodulatory composition comprising CC to the individual.

BRIEF DESCRIPTION OF THE DRAWINGS

FIG. 30 demonstrates that CC can be used to differentiate/expand myeloid cells from pluripotent stem cells present in human peripheral blood. The data represent $CD34^+CD45^-$, $CD34^+ CD45^-CD11c^+$ and $CD34^+CD45^-CD11b^+$ populations as determined by flow cytometry.

DEFINITIONS

Figure 1:
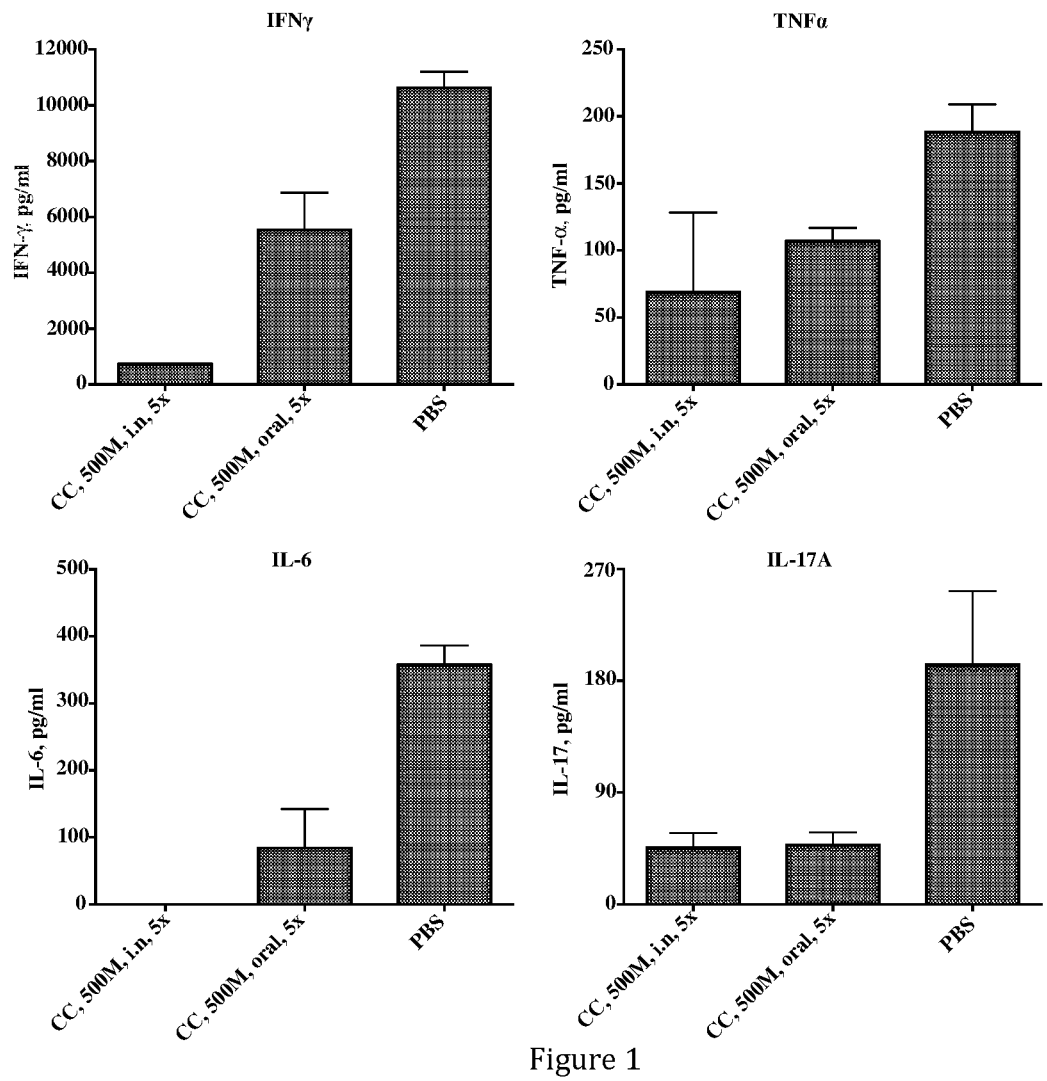
FIG. 1 demonstrates the reduction in concanavalin A (ConA) induced pro-inflammatory cytokines (IFN-γ, TNF-α, IL-6 and IL-17A) production in splenocytes isolated from CC and PBS treated mice by intranasal and oral routes twice weekly. Data are expressed in pg/ml and shown as average±standard deviation (SD) of triplicates.

The terms "individual," "host," "subject," and "patient" are used interchangeably herein, and refer to mammals, including, but not limited to, humans, non-human primates (e.g. simians), non-human mammals (e.g., mammalian livestock animals (e.g., bovine, porcine, caprine, and ovine animals)), and mammalian pets (e.g., cats, dogs); fish; and birds (e.g., chicken).

A "biological sample" encompasses a variety of sample types obtained from an individual. The definition encompasses blood, serum, plasma, and other liquid samples of biological origin; solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as epithelial cells. The term "biological sample" encompasses a clinical sample, and also includes cells in culture, cell supernatants, organs, tissue samples, lung biopsy samples, lung epithelial cells, gastrointestinal epithelial cells, gastrointestinal tract tissue samples, bronchoalveolar lavage (BAL) fluid samples, nasal lavage fluid samples, blood, plasma, serum, cerebrospinal fluid, fecal samples, and the like.

An "immunomodulator" or "immunomodulatory agent" is any agent which does one or more of: restores depressed immune function, down-regulates an abnormal immune function, regulates abnormal/excessive immune function, enhances normal immune function, and provide desired immune response. Immune function includes one or more of: humoral (antibody-mediated) immunity, cellular immunity, and innate immunity. An "immunomodulator" includes agents acting directly on the cells involved in the expression of immune response, or on cellular or molecular mechanisms, which, in turn, act to modify the function of cells involved in immune response. Regulation of immune function may result from the action of an immunomodulatory agent to abrogate activating mechanisms derived by positive-feedback influences endogenous or exogenous to the immune system. Regulation of immune function may result from the action of an immunomodulatory agent to abrogate suppressing mechanisms derived by negative-feedback influences endogenous or exogenous to the immune system. Thus, immunomodulators can have diverse mechanisms of action.

The terms "modulate" and "modulation" refer to increasing, reducing, or balancing the number and/or activity of immune cells, cytokines, chemokines, antibodies, soluble factors, surface molecules, intracellular molecules, effector functions, regulatory functions etc.

The terms "autoimmune disease" and "autoimmune disorder" are used interchangeably herein to refer to diseases characterized by an immune response to a self antigen, i.e., an immune response to substances and tissues normally present in the body.

The term "inflammatory disease" refers to a disease caused by, resulting from, or resulting in inflammation. The term "inflammatory disease" may also refer to a dysregulated inflammatory reaction that causes an exaggerated response by various innate and adaptive immune cells leading to abnormal tissue damage and/or cell death.

An "adjuvant" is any agent which is capable of potentiating an immune response and are, therefore, one class of immunopotentiators (Stites and Terr, *Basic and Clinical Immunology*, 7$^{th}$ Ed., Appleton and Lange Norwalk Conn. pp. 797, 1991). Adjuvants are used to increase the immune responses in vaccination in order to enhance the humoral and/or cell mediated immune responses.

A "cytokine" means any secreted polypeptide that affects the functions of other cells, and is a molecule, which modulates interactions between cells in the immune or inflammatory response. A cytokine includes, but is not limited to monokines, chemokines, and lymphokines, regardless of which cells produce them.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, bi-specific antibodies, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. An antibody may be monovalent or bivalent.

A "therapeutically effective amount" or "efficacious amount" means the amount of a compound or agent that, when administered to a mammal or other subject for treating a disease, is sufficient to effect such treatment for the disease. The "therapeutically effective amount" will vary depending on the compound or agent, the disease and its severity and the age, weight, general health status, sex, etc., of the subject to be treated. In some cases, an "effective amount" of an agent is an amount that: 1) restores the immune function to normal levels; 2) modulates immune function to normal levels; or 3) reduces immune function to below a pathological level.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

A "pharmaceutically acceptable carrier or excipient" means a non-toxic solid, semi-solid, or liquid filler, diluent, encapsulating material or formulation auxiliary of any type. One skilled in the art of preparing formulations can readily select the proper form and mode of administration depending upon the particular characteristics of the gent selected, the disease state to be treated, the stage of the disease, and other relevant circumstances.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a live *Caulobacter crescentus*" includes a plurality of such bacteria and reference to "the cytokine" includes references to one or more cytokines and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure relates to *Caulobacter crescentus* (CC) and its use as an immunomodulatory biotherapeutic agent. CC has been shown to have immunomodulatory effects by modulating innate and adaptive immune responses. The present disclosure provides immunomodulatory compositions comprising live *Caulobacter crescentus* (CC). Immunomodulatory compositions of the present disclosure are useful for modulating an immune response in an individual. Immunomodulatory compositions of the present disclosure are useful for reducing an undesired immune response in an individual. Immunomodulatory compositions of the present disclosure are useful for reducing inflammation in an individual. The present disclosure provides methods of modulating an immune response in an individual, involving administering an immunomodulatory composition comprising CC to the individual. The present disclosure provides methods of reducing an undesired immune response in an individual, involving administering an immunomodulatory composition comprising live CC to the individual. The present disclosure provides methods of reducing inflammation in an individual, involving administering an immunomodulatory composition comprising live CC to the individual.

Immunomodulatory Compositions

The present disclosure provides immunomodulatory compositions comprising *Caulobacter crescentus* (CC). CC in an immunomodulatory composition of the present disclosure are viable. CC in an immunomodulatory composition can be non-denatured, mutated, attenuated and/or genetically modified. An immunomodulatory composition of the present disclosure can comprise a cocktail of one or more different strains of *Caulobacter crescentus* bacteria.

CC-containing immunomodulatory compositions include the CC by itself with a pharmaceutically acceptable carrier or excipients for immunomodulatory activity, including "adjuvanting" in which CC administration to a subject may be wholly independent of, and/or separated temporally and/or spatially from, administration to the subject of one or more antigens against which modulation or regulation of an immune response (e.g., an antigen specific response) in the subject is desired.

An immunomodulatory composition of the present disclosure can modulate (e.g., reduce) an immune response in an individual. In some cases, an effective amount of an immunomodulatory composition of the present disclosure is an amount that is effective, when administered in a single dose or in multiple doses, to modulate (e.g., reduce) the number of B cells in an individual. For example, in some cases, an effective amount of an immunomodulatory composition of the present disclosure is an amount that is effective, when administered in a single dose or in multiple doses, to modulate (e.g., reduce) the number of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of B cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number of antigen-specific B cells in an individual. For example, in some cases, an effective amount of an immunomodulatory composition of the present disclosure is an amount that is effective, when administered in a single dose or in multiple doses, to reduce the number of antigen-specific B cells in an individual by at least 10%, at least 15%, at least 20%, at least 25%, at least 30%, at least 35%, at least 40%, at least 45%, at least 50%, at least 75%, or more than 75%, compared to the number of antigen-specific B cells in the individual in the absence of treatment with the immunomodulatory composition. For example, in some cases, an effective amount of an immunomodulatory composition of the present disclosure is an amount that is effective, when administered in a single dose or in multiple doses, to reduce the number of autoantigen-specific B cells in an individual by at least 10%, at least 15%, at least 20%, at least 25%, at least 30%, at least 35%, at least 40%, at least 45%, at least 50%, at least 75%, or more than 75%, compared to the number of autoantigen-specific B cells in the individual in the absence of treatment with the immunomodulatory composition. For example, in some cases, an effective amount of an immunomodulatory composition of the present disclosure is an amount that is effective, when administered in a single dose or in multiple doses, to reduce the number of allergen-specific B cells in an individual by at least 10%, at least 15%, at least 20%, at least 25%, at least 30%, at least 35%, at least 40%, at least 45%, at least 50%, at least 75%, or more than 75%, compared to the number of allergen-specific B cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) activity of B cells in an individual. For example, in some cases, an effective amount of an immunomodulatory composition of the present disclosure is an amount that is effective, when administered in a single dose or in multiple doses, to modulate (e.g., reduce) activation of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, at least 25-fold, at least 50-fold, at least 100-fold, or more than 100-fold, compared to the activation level of B cells in the individual in the absence of treatment with the immunomodulatory composition. For example, in some cases, an effective amount of an immunomodulatory composition of the present disclosure is an amount that is effective, when administered in a single dose or in multiple doses, to reduce the activation of B cells in an individual by at least 10%, at least 15%, at least 20%, at least 25%, at least 30%, at least 35%, at least 40%, at least 45%, at least 50%, at least 75%, or more than 75%, compared to the activation level of B cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the amount of antibody specific to a given antigen in the individual. For example, in some cases, an effective amount of an immunomodulatory composition of the present disclosure is an amount that is effective, when administered in a single dose or in multiple doses, to modulate (e.g., reduce) the amount of antibody specific to a given antigen in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of antibody specific to the antigen in the individual in the absence of treatment with the immunomodulatory composition. For example, in some cases, an effective amount of an immunomodulatory composition of the present disclosure is an amount that is effective, when administered in a single dose or in multiple doses, to reduce the amount of antibody specific to a given antigen in an individual by at least 10%, at least 15%, at least 20%, at least 25%, at least 30%, at least 35%, at least 40%, at least 45%, at least 50%, at least 75%, or more than 75%, compared to the amount of antibody specific to the antigen in the individual in the absence of treatment with the immunomodulatory composition. For example, in some cases, an effective amount of an immunomodulatory composition of the present disclosure is an amount that is effective, when administered in a single dose or in multiple doses, to reduce the amount of autoantigen-specific antibody in an individual by at least 10%, at least 15%, at least 20%, at least 25%, at least 30%, at least 35%, at least 40%, at least 45%, at least 50%, at least 75%, or more than 75%, compared to the amount of autoantigen-specific antibody in the individual in the absence of treatment with the immunomodulatory composition. For example, in some cases, an effective amount of an immunomodulatory composition of the present disclosure is an amount that is effective, when administered in a single dose or in multiple doses, to reduce the amount of allergen-specific antibody in an individual by at least 10%, at least 15%, at least 20%, at least 25%, at least 30%, at least 35%, at least 40%, at least 45%, at least 50%, at least 75%, or more than 75%, compared to the amount of allergen-specific antibody in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) production of one or more cytokines in the individual. For example, in some cases, an effective amount of an immunomodulatory composition of the present disclosure is an amount that is effective, when administered in a single dose or in multiple doses, to modulate (e.g., reduce) production of one or more cytokines in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of the cytokine in the individual in the absence of treatment with the immunomodulatory composition. For example, in some cases, an effective amount of an immunomodulatory composition of the present disclosure is an amount that is effective, when administered in a single dose or in multiple doses, to reduce the production of one or more cytokines in an individual by at least 10%, at least 15%, at least 20%, at least 25%, at least 30%, at least 35%, at least 40%, at least 45%, at least 50%, at least 75%, or more than 75%, compared to the production of one or more cytokines in the individual in the absence of treatment with the immunomodulatory composition. In other cases, an effective amount of an immunomodulatory composition of the present disclosure is an amount that is effective, when administered in a single dose or in multiple doses, to modulate (e.g., reduce) production of GM-CSF in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of GM-CSF in the individual in the absence of treatment with the immunomodulatory composition. For example, in some cases, an effective amount of an immunomodulatory composition of the present disclosure is an amount that is effective, when administered in a single dose or in multiple doses, to reduce the production of GM-CSF in an individual by at least 10%, at least 15%, at least 20%, at least 25%, at least 30%, at least 35%, at least 40%, at least 45%, at least 50%, at least 75%, or more than 75%, compared to the amount of GM-CSF in the individual in the absence of treatment with the immunomodulatory composition. For example, in some cases, an effective amount of an immunomodulatory composition of the present disclosure is an amount that is effective, when administered in a single dose or in multiple doses, to modulate (e.g., reduce) production of IL-22 in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-22 in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-22 in an individual by at least 10%, at least 15%, at least 20%, at least 25%, at least 30%, at least 35%, at least 40%, at least 45%, at least 50%, at least 75%, or more than 75%, compared to the amount of IL-22 in the individual in the absence of treatment with the immunomodulatory composition. In other, an effective amount of an immunomodulatory composition of the present disclosure is an amount that is effective, when administered in a single dose or in multiple doses, to modulate (e.g., reduce) production of interferon (IFN)-α and/or IFN-β and/or IFN-γ in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IFN-α or IFN-β or IFN-γ in the individual in the absence of treatment with the immunomodulatory composition. For example, in some cases, an effective amount of an immunomodulatory composition of the present disclosure is an amount that is effective, when administered in a single dose or in multiple doses, to reduce the production of interferon (IFN)-α and/or IFN-β and/or IFN-γ in an individual by at least 10%, at least 15%, at least 20%, at least 25%, at least 30%, at least 35%, at least 40%, at least 45%, at least 50%, at least 75%, or more than 75%, compared to the amount of interferon (IFN)-α and/or IFN-β and/or IFN-γ in the individual in the absence of treatment with the immunomodulatory composition. For example, in some cases, an effective amount of an immunomodulatory composition of the present disclosure is an amount that is effective, when administered in a single dose or in multiple doses, to reduce the production of IFN-γ in an individual by at least 10%, at least 15%, at least 20%, at least 25%, at least 30%, at least 35%, at least 40%, at least 45%, at least 50%, at least 75%, or more than 75%, compared to the amount of IFN-γ in the individual in the absence of treatment with the immunomodulatory composition.

As another example, in some cases, an effective amount of an immunomodulatory composition of the present disclosure is an amount that is effective, when administered in a single dose or in multiple doses, to modulate (e.g., reduce) production of one or more of IL-1β, IL-17A, IL-2, IL-10, IL-6 and TNF-α in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-1β, IL-17A, IL-2, IL-10, IL-6, or TNF-α in the individual in the absence of treatment with the immunomodulatory composition. In some cases, an effective amount of an immunomodulatory composition of the present disclosure is an amount that is effective, when administered in a single dose or in multiple doses, to increase the level of IL-10 in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-10 in the individual in the absence of treatment with the immunomodulatory composition. In some cases, an effective amount of an immunomodulatory composition of the present disclosure is an amount that is effective, when administered in a single dose or in multiple doses, to increase the number of IL-10-producing CD4$^+$ and/or CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of IL-10-producing CD4$^+$ and/or CD8$^+$ T cells in the individual in the absence of treatment with the immunomodulatory composition. As another example, in some cases, an effective amount of an immunomodulatory composition of the present disclosure is an amount that is effective, when administered in a single dose or in multiple doses, to reduce the production of one or more of IL-1β, IL-17A, IL-2, IL-6 and TNF-α in an individual by at least 10%, at least 15%, at least 20%, at least 25%, at least 30%, at least 35%, at least 40%, at least 45%, at least 50%, at least 75%, or more than 75%, compared to the amount of one or more of IL-1 β, IL-17A, IL-2, IL-6 and TNF-α in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-17 in an individual by at least 10%, at least 15%, at least 20%, at least 25%, at least 30%, at least 35%, at least 40%, at least 45%, at least 50%, at least 75%, or more than 75%, compared to the amount of IL-17 in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-2 in an individual by at least 10%, at least 15%, at least 20%, at least 25%, at least 30%, at least 35%, at least 40%, at least 45%, at least 50%, at least 75%, or more than 75%, compared to the amount of IL-2 the individual in the absence of treatment with the immunomodulatory composition. For example, in some cases, an effective amount of an immunomodulatory composition of the present disclosure is an amount that is effective, when administered in a single dose or in multiple doses, to reduce the production of TNF-α in an individual by at least 10%, at least 15%, at least 20%, at least 25%, at least 30%, at least 35%, at least 40%, at least 45%, at least 50%, at least 75%, or more than 75%, compared to the amount of TNF-α in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-6 in an individual by at least 10%, at least 15%, at least 20%, at least 25%, at least 30%, at least 35%, at least 40%, at least 45%, at least 50%, at least 75%, or more than 75%, compared to the amount of IL-6 in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-1β in an individual by at least 10%, at least 15%, at least 20%, at least 25%, at least 30%, at least 35%, at least 40%, at least 45%, at least 50%, at least 75%, or more than 75%, compared to the amount of IL-1β in the individual in the absence of treatment with the immunomodulatory composition. In some cases, an effective amount of an immunomodulatory composition of the present disclosure is an amount that is effective, when administered in a single dose or in multiple doses, to increase the level of TGF-β in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of TGF-β in the individual in the absence of treatment with the immunomodulatory composition.

In some cases, an effective amount of an immunomodulatory composition of the present disclosure is an amount that is effective, when administered in a single dose or in multiple doses, to modulate (e.g., increase, reduce or balance) production of one or more cytokines, chemokines or lymphotoxins such as but not limited to GM-CSF, IL-2, IL-22, Interferons, IL-1β, TGF-β, IL-17A, IL-2, IL-10, IL-6, IL-5, IL-13, TNF-α, IL-9, IL-28, KC/IL-8, MIP-1α, LTα4 etc. in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of cytokines, chemokines or lymphotoxins such as but not limited to GM-CSF, IL-2, IL-22, Interferons, IL-1β, TGF-β, IL-17A, IL-2, IL-10, IL-6, IL-5, IL-13, TNF-α, IL-9, IL-28, KC/IL-8, MIP-1α, LTα4 etc. in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) a Th1 response in an individual. For example, in some cases, an effective amount of an immunomodulatory composition of the present disclosure is an amount that is effective, when administered in a single dose or in multiple doses, to modulate (e.g., reduce) a Th1 response in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the level of the Th1 response in the individual in the absence of treatment with the immunomodulatory composition. For example, in some cases, an effective amount of an immunomodulatory composition of the present disclosure is an amount that is effective, when administered in a single dose or in multiple doses, to reduce a Th1 response in an individual by at least 10%, at least 15%, at least 20%, at least 25%, at least 30%, at least 35%, at least 40%, at least 45%, at least 50%, at least 75%, or more than 75%, compared to the Th1 response in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of CD4$^+$ T cells in an individual. For example, in some cases, an effective amount of an immunomodulatory composition of the present disclosure is an amount that is effective, when administered in a single dose or in multiple doses, to modulate (e.g., reduce) the number and/or activity of CD4$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD4$^+$ T cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific CD4$^+$ T cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific CD4$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD4$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of CD4$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of CD4$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific CD4$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific CD4$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of autoantigen-specific CD4$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of autoantigen-specific CD4$^+$ T cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of CD8$^+$ T cells in an individual. For example, in some cases, an effective amount of an immunomodulatory composition of the present disclosure is an amount that is effective, when administered in a single dose or in multiple doses, to modulate (e.g., reduce) the number and/or activity of CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD8$^+$ T cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific CD8$^+$ T cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD8$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of CD8$^+$ T in an individual by at least 10%, at least 15%, at least 20%, at least 25%, at least 30%, at least 35%, at least 40%, at least 45%, at least 50%, at least 75%, or more than 75%, compared to the number and/or activity of CD8$^+$ T in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific CD8$^+$ T in an individual by at least 10%, at least 15%, at least 20%, at least 25%, at least 30%, at least 35%, at least 40%, at least 45%, at least 50%, at least 75%, or more than 75%, compared to the number and/or activity of antigen-specific CD8$^+$ T in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of autoantigen-specific CD8$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of autoantigen-specific CD8$^+$ T cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of cytolytic T cells in an individual. For example, in some cases, an effective amount of an immunomodulatory composition of the present disclosure is an amount that is effective, when administered in a single dose or in multiple doses, to modulate (e.g., reduce) the number and/or activity of cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of cytolytic T cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific cytolytic T cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific cytolytic T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of cytolytic T cells in an individual by at least 10%, at least 15%, at least 20%, at least 25%, at least 30%, at least 35%, at least 40%, at least 45%, at least 50%, at least 75%, or more than 75%, compared to the number and/or activity of cytolytic T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific cytolytic T cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific cytolytic T cells in the individual in the absence of treatment with the immunomodulatory composition.

In some cases, an effective amount of an immunomodulatory composition of the present disclosure is an amount that is effective, when administered in a single dose or in multiple doses, to modulate the number and/or activity of one or more of natural killer (NK) cells, NKT cells, γδ T cells, innate lymphoid cells (ILCs), macrophages, and dendritic cells (DCs) in an individual. For example, in some cases, an effective amount of an immunomodulatory composition of the present disclosure is an amount that is effective, when administered in a single dose or in multiple doses, to modulate the number and/or activity of one or more of NK cells, NKT cells, γδ T cells, ILCs, macrophages, and DCs in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of NK cells, NKT cells, γδ T cells, ILCs, macrophages, and DCs in the individual in the absence of treatment with the immunomodulatory composition. For example, in some cases, an effective amount of an immunomodulatory composition of the present disclosure is an amount that is effective, when administered in a single dose or in multiple doses, to modulate the number and/or activity of one or more of NK cells, NKT cells, γδ T cells, ILCs, macrophages, and DCs in an individual by at least 10%, at least 15%, at least 20%, at least 25%, at least 30%, at least 35%, at least 40%, at least 45%, at least 50%, at least 75%, or more than 75%, compared to the number and/or activity of NK cells, NKT cells, γδ T cells, ILCs, macrophages, and DCs in the individual in the absence of treatment with the immunomodulatory composition.

In some cases, an effective amount of an immunomodulatory composition of the present disclosure is an amount that is effective, when administered in a single dose or in multiple doses, to modulate the number and/or activity of regulatory cells in an individual. Regulatory T cells (Tregs) are CD4$^+$ or CD8$^+$, and may also be FoxP3$^+$. Tregs may also be defined by other markers such as PD-1, CTLA-4 etc. Regulatory cells can also be comprised of other innate cells such as NK, NKT, γδ T cells, ILCs and DCs, and B lymphocytes. NK and NKT can also be FoxP3$^+$ and may also be defined by other markers such as PD-1. "Modulate the number and/or activity" of regulatory cells, as used herein, refers to increasing, decreasing, or balancing the number and/or activity of regulatory cells. For example, in some cases, an effective amount of an immunomodulatory composition of the present disclosure is an amount that is effective, when administered in a single dose or in multiple doses, to modulate the number and/or activity of regulatory cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared number and/or activity of regulatory cells in the individual in the absence of treatment with the immunomodulatory composition. For example, in some cases, an effective amount of an immunomodulatory composition of the present disclosure is an amount that is effective, when administered in a single dose or in multiple doses, to increase the number of regulatory cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of regulatory cells in the individual in the absence of treatment with the immunomodulatory composition. As one example, in some cases, an effective amount of an immunomodulatory composition of the present disclosure is an amount that is effective, when administered in a single dose or in multiple doses, to increase the number of $CD8^+$ regulatory cells (e.g., $CD8^+/CD25^+/FoxP3^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of $CD8^+$ regulatory cells (e.g., $CD8^+/CD25^+/FoxP3^+$ cells) in the individual in the absence of treatment with the immunomodulatory composition. As another example, in some cases, an effective amount of an immunomodulatory composition of the present disclosure is an amount that is effective, when administered in a single dose or in multiple doses, to increase the number of $CD8^+$ regulatory cells (e.g., $CD8^+/FoxP3^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of $CD8^+$ regulatory cells (e.g., $CD8^+/FoxP3^+$ cells) in the individual in the absence of treatment with the immunomodulatory composition As another example, in some cases, an effective amount of an immunomodulatory composition of the present disclosure is an amount that is effective, when administered in a single dose or in multiple doses, to increase the number of NKT cells (e.g., $NKT^+/FoxP3^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of NKT cells (e.g., $NKT^+/FoxP3^+$ cells) in the individual in the absence of treatment with the immunomodulatory composition. As another example, in some cases, an effective amount of an immunomodulatory composition of the present disclosure is an amount that is effective, when administered in a single dose or in multiple doses, to increase the number of NKT cells (e.g., $NKT^+/PD-1^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of NKT cells (e.g., $NKT^+/PD-1^+$ cells) in the individual in the absence of treatment with the immunomodulatory composition. As another example, in some cases, an effective amount of an immunomodulatory composition of the present disclosure is an amount that is effective, when administered in a single dose or in multiple doses, to increase the number of NK cells (e.g., $NK^+/FoxP3^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of NK cells (e.g., $NK^+/FoxP3^+$ cells) in the individual in the absence of treatment with the immunomodulatory composition. As another example, in some cases, an effective amount of an immunomodulatory composition of the present disclosure is an amount that is effective, when administered in a single dose or in multiple doses, to increase the number of NK cells (e.g., $NK^+/PD-1^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of NK cells (e.g., $NK^+/PD-1^+$ cells) in the individual in the absence of treatment with the immunomodulatory composition. As another example, in some cases, an effective amount of an immunomodulatory composition of the present disclosure is an amount that is effective, when administered in a single dose or in multiple doses, to increase the number of CD4 regulatory cells (e.g., $CD4^+/FoxP3^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of CD4 regulatory cells (e.g., $CD4^+/FoxP3^+$ cells) in the individual in the absence of treatment with the immunomodulatory composition. As another example, in some cases, an effective amount of an immunomodulatory composition of the present disclosure is an amount that is effective, when administered in a single dose or in multiple doses, to increase the number of CD4 regulatory cells (e.g., $CD4^+/CD25^+/FoxP3^+$ cells) in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of $CD4^+$ regulatory cells (e.g., $CD4^+/CD25^+/FoxP3^+$ cells) in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of Th17 cells in an individual. For example, in some cases, an effective amount of an immunomodulatory composition of the present disclosure is an amount that is effective, when administered in a single dose or in multiple doses, to modulate (e.g., reduce) the number and/or activity of Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th17 cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific Th17 cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th17 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of Th17 cells in an individual by at least 10%, at least 15%, at least 20%, at least 25%, at least 30%, at least 35%, at least 40%, at least 45%, at least 50%, at least 75%, or more than 75%, compared to the number and/or activity of Th17 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific Th17 cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific Th17 cells in the individual in the absence of treatment with the immunomodulatory composition.

In some cases, an effective amount of an immunomodulatory composition of the present disclosure is an amount that is effective, when administered in a single dose or in multiple doses, to normalize the level of one or more serum markers of pathological immune responses. For example, in some cases, an effective amount of an immunomodulatory composition of the present disclosure is an amount that is effective, when administered in a single dose or in multiple doses, in normalizing the level of one or more of the serum markers (these markers include, but are not restricted to, cholesterol (CHOL), glucose (GLU), globulin (GLOB), alanine aminotransferases (ALT), aspartate aminotransferases (AST), total phosphates (TP), total bilirubin (TBIL), phosphate (PHOS), triglycerides (TRIG), uric acid (URIC), creatine kinase (CK) and urea) in an individual by at least 10%, at least 15%, at least 20%, at least 25%, at least 30%, at least 35%, at least 40%, at least 45%, at least 50%, at least 75%, or more than 75%, compared with the level of CH, GLU, GLOB, ALT, AST, TP, PHOS, TRIG, URIC, CK, TBIL or urea in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of Th22 cells in an individual. For example, in some cases, an effective amount of an immunomodulatory composition of the present disclosure is an amount that is effective, when administered in a single dose or in multiple doses, to modulate (e.g., reduce) the number and/or activity of Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th22 cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific Th22 cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th22 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of Th22 cells in an individual by at least 10%, at least 15%, at least 20%, at least 25%, at least 30%, at least 35%, at least 40%, at least 45%, at least 50%, at least 75%, or more than 75%, compared to the number and/or activity of Th22 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific Th22 cells in an individual by at least 10%, at least 15%, at least 20%, at least 25%, at least 30%, at least 35%, at least 40%, at least 45%, at least 50%, at least 75%, or more than 75%, compared to the the number and/or activity of antigen-specific Th22 cells in the individual in the absence of treatment with the immunomodulatory composition.

In some cases, an effective amount of an immunomodulatory composition of the present disclosure is an amount that is effective, when administered in a single dose or in multiple doses, to modulate the number and/or activity of TH9 cells in an individual. "Modulate the number and/or activity" of TH9 cells, as used herein, refers to increasing, decreasing, or balancing the number and/or activity of TH9 cells. For example, in some cases, an effective amount of an immunomodulatory composition of the present disclosure is an amount that is effective, when administered in a single dose or in multiple doses, to modulate the number and/or activity of TH9 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared number and/or activity of TH9 cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) and/or regulate innate and/or adaptive (including both cellular and humoral) immune responses in an individual. For example, in some cases, an effective amount of an immunomodulatory composition of the present disclosure is an amount that is effective, when administered in a single dose or in multiple doses, to modulate (e.g., reduce) the number and/or activity of innate and/or adaptive immune cells and/or their effector functions in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of innate or adaptive immune cells and/or their effector functions in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of innate and/or adaptive immune cells and/or their effector functions in an individual by at least 10%, at least 15%, at least 20%, at least 25%, at least 30%, at least 35%, at least 40%, at least 45%, at least 50%, at least 75%, or more than 75%, compared to the number and/or activity of innate and/or adaptive immune cells and/or their effector functions in the individual in the absence of treatment with the immunomodulatory composition.

In some cases, an effective amount of an immunomodulatory composition of the present disclosure is an amount that is effective, when administered in a single dose or in multiple doses, to induce and/or increase apoptosis in innate and/or adaptive immune cells in an individual to protect from undesirable inflammation. For example, in some cases, an effective amount of an immunomodulatory composition of the present disclosure is an amount that is effective, when administered in a single dose or in multiple doses, to induce and/or increase apoptosis in innate and/or adaptive immune cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of one or more of innate or adaptive immune cells in the individual in the absence of treatment with the immunomodulatory composition.

In some cases, an effective amount of an immunomodulatory composition of the present disclosure is an amount that is effective, when administered in a single dose or in multiple doses, to induce proliferation and/or differentiation of hematopoietic stem cells, and restore homeostasis. For example, in some cases, an effective amount of an immunomodulatory composition of the present disclosure is an amount that is effective, when administered in a single dose or in multiple doses, to induce proliferation and/or differentiation of hematopoietic stem cells, and restore homeostasis in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the individual in the absence of treatment with the immunomodulatory composition.

In some cases, an immunomodulatory composition of the present disclosure comprises CC and an antigen. Where an immunomodulatory composition of the present disclosure comprises CC and an antigen, in some cases, an effective amount of an immunomodulatory composition of the present disclosure is an amount that is effective, when administered in a single dose or in multiple doses, to modulate (e.g., reduce) an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. For example, where the antigen is an antigen associated with or derived from an autoantigen or an allergen, an effective amount of an immunomodulatory composition of the present disclosure is an amount that is effective, when administered in a single dose or in multiple doses, to modulate (e.g., reduce) an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. For example, where the immunomodulatory composition comprises CC, an antigen, an autoantigen or an allergen, alone or in combination with each other, in some cases, an effective amount of an immunomodulatory composition of the present disclosure is an amount that is effective, when administered in a single dose or in multiple doses, to reduce the immune response to the antigen in an individual by at least 10%, at least 15%, at least 20%, at least 25%, at least 30%, at least 35%, at least 40%, at least 45%, at least 50%, at least 75%, or more than 75%, compared to the immune response to the antigen in the individual in the absence of treatment with the immunomodulatory composition.

The immune response can be a humoral immune response, e.g., a B cell or antibody immune response. Thus, e.g., in some cases, where the antigen is an antigen associated with or derived from an autoantigen or an allergen, an effective amount of an immunomodulatory composition of the present disclosure is an amount that is effective, when administered in a single dose or in multiple doses, to modulate (e.g., reduce) a B cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the B cell response to the antigen in the absence of treatment with the immunomodulatory composition. For example, in some cases, an effective amount of an immunomodulatory composition of the present disclosure is an amount that is effective, when administered in a single dose or in multiple doses, to reduce the B cell response to the antigen in an individual by at least 10%, at least 15%, at least 20%, at least 25%, at least 30%, at least 35%, at least 40%, at least 45%, at least 50%, at least 75%, or more than 75%, compared to the B cell response to the antigen in the individual in the absence of treatment with the immunomodulatory composition. For example, in some cases, where the antigen is an antigen associated with or derived from an autoantigen or an allergen, an effective amount of an immunomodulatory composition of the present disclosure is an amount that is effective, when administered in a single dose or in multiple doses, to modulate (e.g., reduce) the amount of antibody specific to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the amount of antibody specific to the antigen in the absence of treatment with the immunomodulatory composition. For example, in some cases, an effective amount of an immunomodulatory composition of the present disclosure is an amount that is effective, when administered in a single dose or in multiple doses, to reduce the amount of antibody specific to the antigen in an individual by at least 10%, at least 15%, at least 20%, at least 25%, at least 30%, at least 35%, at least 40%, at least 45%, at least 50%, at least 75%, or more than 75%, compared to the amount of antibody specific to the antigen in the individual in the absence of treatment with the immunomodulatory composition.

The immune response can be a cellular immune response, e.g., a T cell response. Thus, e.g., in some cases, where the antigen is an antigen associated with or derived from an autoantigen or an allergen, an effective amount of an immunomodulatory composition of the present disclosure is an amount that is effective, when administered in a single dose or in multiple doses, to modulate a (e.g., reduce) T cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the T cell response to the antigen in the absence of treatment with the immunomodulatory composition. For example, in some cases, an effective amount of an immunomodulatory composition of the present disclosure is an amount that is effective, when administered in a single dose or in multiple doses, to reduce the T cell response to the antigen in an individual by at least 10%, at least 15%, at least 20%, at least 25%, at least 30%, at least 35%, at least 40%, at least 45%, at least 50%, at least 75%, or more than 75%, compared to the T cell response to the antigen in the individual in the absence of treatment with the immunomodulatory composition. In some cases, the immune response is a humoral immune response and a cellular immune response.

An immunomodulatory composition of the present disclosure can comprise CC in an amount of from about $10^3$ CC per ml to about $10^{12}$ CC per ml. For example, an immunomodulatory composition of the present disclosure can comprise CC in an amount of from about $10^3$ CC per ml to about $10^4$ CC per ml, from about $10^4$ CC per ml to about $10^5$ CC per ml, from about $10^5$ CC per ml to about $10^6$ CC per ml, from about $10^6$ CC per ml to about $10^7$ CC per ml, from about $10^8$ CC per ml to about $10^9$ CC per ml, from about $10^9$ CC per ml to about $10^{10}$ CC per ml, from about $10^{10}$ CC per ml to about $10^{11}$ CC per ml, or from about $10^{11}$ CC per ml to about $10^{12}$ CC per ml.

An immunomodulatory composition of the present disclosure can comprise CC in an amount of from about $10^3$ CC per mg to about $10^{12}$ CC per mg. For example, an immunomodulatory composition of the present disclosure can comprise CC in an amount of from about $10^3$ CC per mg to about $10^4$ CC per mg, from about $10^4$ CC per mg to about $10^5$ CC per mg, from about $10^5$ CC per mg to about $10^6$ CC per mg, from about $10^6$ CC per mg to about $10^7$ CC per mg, from about $10^8$ CC per mg to about $10^9$ CC per mg, from about $10^9$ CC per mg to about $10^{10}$ CC per mg, from about $10^{10}$ CC per mg to about $10^{11}$ CC per mg, or from about $10^{11}$ CC per mg to about $10^{12}$ CC per mg.

An immunomodulatory composition of the present disclosure can comprise CC in an amount of from about $10^3$ CC per gram to about $10^{15}$ CC per gram. For example, an immunomodulatory composition of the present disclosure can comprise CC in an amount of from about $10^3$ CC per gram to about $10^4$ CC per gram, from about $10^4$ CC per gram to about $10^5$ CC per gram, from about $10^5$ CC per gram to about $10^6$ CC per gram, from about $10^6$ CC per gram to about $10^7$ CC per gram, from about $10^8$ CC per gram to about $10^9$ CC per gram, from about $10^9$ CC per gram to about $10^{10}$ CC per gram, from about $10^{10}$ CC per gram to about $10^{11}$ CC per gram, from about $10^{11}$ CC per gram to about $10^{12}$ CC per gram, from about $10^{12}$ CC per gram to about $10^{13}$ CC per gram, from about $10^{13}$ CC per gram to about $10^{14}$ CC per gram, or from about $10^{14}$ CC per gram to about $10^{15}$ CC per gram.

An immunomodulatory composition of the present disclosure can comprise CC in an amount of from about $10^2$ to about $10^{20}$ colony forming units (cfu) per unit dosage form; for example, an immunomodulatory composition of the present disclosure can comprise CC in an amount of from about $10^2$ to about $10^3$ from about $10^3$ to about $10^5$, from about $10^5$ to about $10^7$, from about $10^7$ to about $10^9$, from about $10^9$ to about $10^{11}$, from about $10^{11}$ to about $10^{13}$, from about $10^{13}$ to about $10^{15}$, from about $10^{15}$ to about $10^{18}$, or from about $10^{18}$ to about $10^{20}$, cfu per unit dosage form. A unit dosage form can be an amount that is administered in a single dose; for example, a unit dosage form can be 0.5 ml, 1.0 ml, or other volume suitable for administration in a single dose.

CC can be prepared by exposing *Caulobacter crescentus* to a temperature of from about 0° C. to about 37° C. (e.g., from about 0° C. to 15° C.; from about 10° C. to 20° C.; from about 20° C. to 25° C.; from about 23° C. to 25° C.; from about 23° C. to 37° C.; or from about 30° C. to 35° C.) for a time period of from about 1 hour to extended periods of time (e.g., at least 1 hour; at least 2 hours; at least 4 hours; overnight; at least 24 hours; at least 48 hours; at least 100 hours, or more than 100 hours). CC can also be stored in saline, phosphate-buffered saline (PBS), or any other buffer, at temperatures from about 36° C. to −170° C. (e.g., from about 0° C. to 36° C.; from about 0° C. to 4° C.; from about 10° C. to 15° C.; from about 0° C. to −20° C.; from about −10° C. and below), or in conditions known to those skilled in the art. CC can be 0.0000001 to 100% viable. For example, CC can be 0.0000001 to 0.000001% viable, 0.000001 to 0.00001% viable, 0.00001 to 0.0001% viable, 0.0001% to 0.001% viable, 0.001% to 0.01% viable, 0.01% to 0.1% viable, 0.1% to 1% viable, 1% to 10% viable, from 10% to 100% viable, from 25% to 100 viable, from 50% to 100% viable, from 75% to 100% viable, or from 90% to 100% viable.

An immunomodulatory composition of the present disclosure can comprise CC grown in culture at various optical density units (ODs) from about 0.1 OD to 30.0 ODs. For example, the OD of the CC culture grown can be 0.1, 0.2, 0.3, 0.4, 0.5, 0.6, 0.7, 0.8, 0.9 etc.

*Caulobacter crescentus*

An immunomodulatory composition of the present disclosure comprises *Caulobacter*, where the *Caulobacter* is non-pathogenic. The non-pathogenic *Caulobacter* genus includes 19 different species, including two species of Asticcacaulis (*C. vibroides, C. henricii, C. intermedius, C. robiginosus, C. rutilis, C. subvibriodes, C. fusiformis, C. rossii, A. excentricus, A. biprosthecum* etc.). See, e.g., JS Poindexter, The Caulobacters: Ubiquitous Unusual Bacteria, Microbiol Rev 45, 123-179, 1981). Several of the *Caulobacter* sp. are available from the American Type Culture Collection (ATCC), such as CB35, CB26, CB28, KA5, CB66, FC4 etc. All of these species of *Caulobacter* in live, non-denatured, mutated or attenuated forms can be used as immunomodulatory agents described herein. In addition, *Caulobacter* bacteria can be in non-motile prosthecate, motile swarmer, stubby flagellin and flagellin positive, flagellin negative, dividing and/or non-dividing forms. *Caulobacter* sp. can be grown at temperatures ranging from 18°-42° C., and pH ranging from 5-9, but optimally at a temperature in a range of 23-25° C. and pH 7 in PYE medium. Mutated or genetically modified forms of *Caulobacter* sp. can be produced by modifying the nutrients, chemicals, pH, temperature, ultraviolet or infrared light, radiation etc. of the culture conditions, or genetically modifying various enzymes, metabolic pathways, surface molecules, nucleic acids, plasmids, cellular and cell wall components, smooth and rough LPS in live bacteria (JS Poindexter, The Caulobacters: Ubiquitous Unusual Bacteria, Microbiol Rev 45, 123-179, 1981).

*Caulobacter crescentus* can act as a carrier and/or delivery vehicle to deliver antigens. As a non genetic modification (GM), such as electrostatic and hydrophobic interactions, binding of antigens to the *Caulobacter crescentus* surface may enable the *Caulobacter crescentus* to act as an antigen carrier and/or delivery vehicle. Further, due to bioadhesion/mucoadhesion, *Caulobacter crescentus* may facilitate antigen uptake by M cell transport, delivery to and subsequent modulation of DCs/APCs, modulation of NK, NKT, B and T cell responses at mucosal surfaces.

Although the discussion below focuses on *Caulobacter crescentus*, any of a variety of non-pathogenic *Caulobacter* species can be included in an immunomodulatory composition of the present disclosure.

In some cases, an immunomodulatory composition of the present disclosure comprises *Caulobacter crescentus* (CC). In some cases, the *Caulobacter crescentus* is wild-type. In some cases, the *Caulobacter crescentus* is a lipopolysaccharide-negative strain. In some cases, the *Caulobacter crescentus* is an S-layer-negative strain. In some cases, the CC is mutated attenuated, or contains suicidal mutations. In some cases, *Caulobacter crescentus* is with or without a drug resistant plasmid such as chloramphenicol, penicillin resistant plasmids. In some cases, *Caulobacter crescentus* can be grown in other medium than PYE medium.

In some cases, the *Caulobacter crescentus* is genetically modified to produce one or more heterologous polypeptides. The polypeptides can be of a wide range of sizes. Suitable heterologous polypeptides include, but are not limited to, PD1, PDL, CTLA-4, GITR, VISTA; a co-inhibitory protein found on antigen-presenting cells (APCs) or T cells; a cytokine (e.g., IL-10; or any of the above-listed cytokines); a chemokine; an antigen (e.g., an autoantigen or allergen as described herein above); an antibody against an antigen (e.g., an autoantigen; as described herein above), a signalling molecule, a receptor, a cytokine, a pro-apoptotic protein; a fusion protein (e.g., an antigen and a cytokine, an antigen and a carrier protein) etc.

In some cases, *Caulobacter crescentus* is modified by labeling or coupling the bacterium with fluorescent, radioactive isotope, light tags etc.

In some cases, *Caulobacter crescentus* is genetically modified. In some cases, *Caulobacter crescentus* is genetically modified so that microbe is attenuated. In some cases, the nucleic acid of the *Caulobacter crescentus* is modified so that the microbe is attenuated for proliferation.

In some cases, an immunomodulatory composition of the present disclosure comprises whole CC. In some cases, an immunomodulatory composition of the present disclosure comprises CC that are live or non-denatured. In some cases, an immunomodulatory composition of the present disclosure comprises individual or multiple components, byproducts and/or metabolites of CC, which can be isolated, synthesized, or genetically manufactured in other synthetic or natural bacterial cell as synthetic biotics. The components of CC can comprise, but are not limited to, effector molecules e.g., polysaccharides, glycosylceramides, peptidoglycans, nucleic acids, structural proteins, short chain fatty acids, fatty acid metabolites, hydroxyl fatty acids etc. Fractions, components, by-products and/or metabolites of *Caulobacter crescentus* can be obtained by filtering culture supernatants, treatment with various organic solvents, enzymes such as glycosidases, lipase, DNAse, RNAse, protease, lysozyme etc. In some cases, an immunomodulatory composition of the present disclosure comprises individual or multiple components of CC, which can be fused with antigens using physicochemical or genetic methods and used as synthetic bacteria.

In some cases, *Caulobacter crescentus* is bioengineered in its outer membrane vesicle to package and deliver chemotherapeutics and/or immunotherapeutics and synthetic, genetic material from other bacteria. In some cases, *Caulobacter crescentus* is bioengineered and constructed into a genetic circuit as a synthetic therapeutic bacteria, "synthetic biotics".

In some cases, an immunomodulatory composition of the present disclosure comprises S-layer of CC. In some cases, an immunomodulatory composition of the present disclosure comprises S-layer of CC that is genetically modified to display one or more heterologous polypeptides, chemotherapeutics and/or immunotherapeutics. In some cases, an immunomodulatory composition of the present disclosure comprises components of S-layer.

Antigens

An immunomodulatory composition of the present disclosure can comprise, in addition to CC, one or more (e.g., 1, 2, 3, 4, 5, 6, 7, 8, 9, 10, or more than 10) antigens. Suitable antigens include, but are not limited to, an antigen derived from an autoantigen; and an allergen.

In some embodiments, *Caulobacter crescentus* is genetically modified to produce an antigen; and the genetically modified *Caulobacter crescentus* is live, to produce an immunomodulatory composition of the present disclosure. Methods of genetically modifying bacteria are known in the art.

In other embodiments, CC is admixed with an antigen in an immunomodulatory composition of the present disclosure. *Caulobacter crescentus* can act as a carrier and/or delivery vehicle to deliver antigens. As a non genetic modification (GM), such as electrostatic and hydrophobic interactions, binding of antigens to the *Caulobacter crescentus* surface may enable the *Caulobacter crescentus* to act as an antigen carrier and/or delivery vehicle. Further, due to bioadhesion/mucoadhesion, *Caulobacter crescentus* may facilitate antigen uptake by M cell transport, delivery to and subsequent modulation of DCs/APCs, modulation of NK, NKT, B and T cell responses at mucosal surfaces.

An antigen, for use in certain embodiments of the herein described immunomodulatory compositions and methods employing CC, may be any target epitope, molecule, molecular complex, cell or tissue against which modulation of immunogenicity in a subject is desired.

An immunomodulatory composition of the present disclosure can include one or more antigens or antigenic compositions capable of modulating an immune response against a human or animal autoantigen or allergen. The antigen may be associated with autoimmune disease, allergy, asthma, prion disease or any other conditions where modulation of an antigen-specific response would be desirable or beneficial.

A suitable antigen can be any type of antigen known in the art. Antigens can be produced in any of a variety of sources such as plants, animals, prokaryotes, in vitro cell culture, etc. Antigens can be in variety of forms as described below.

Suitable antigens include, e.g., peptides, modified peptides, peptide mimotopes, conformationally-constrained synthetic peptides, multi-epitope peptides from one or more antigens, branched peptides, lipopeptides, monolipopeptides, dilipopeptides, peptides conjugated or fused to proteins, peptides conjugated or fused to T cell or B cell epitopes. See, e.g., U.S. Pat. No. 8,198,400. Suitable antigens include, e.g., full-length antigens, truncated antigens, mutated antigens, and inactivated or combined forms. Suitable antigens include, e.g., proteins, purified or recombinant proteins, recombinant fusion proteins, proteins and peptides conjugated to toll-like receptor (TLR) agonists/antagonists, proteins and peptides conjugated to bacterial toxins, proteins and peptides conjugated to antibodies, proteins and peptides conjugated to cytokines and chemokines, glycoproteins, glycolipoproteins and derivatives thereof. Suitable antigens include, e.g., polysaccharides, polysaccharide conjugates, oligosaccharides, lipids, glycolipids, carbohydrates and derivatives thereof. An antigen can be modified to modulate antigen presentation and/or co-inhibition, or increase co-inhibitory signals.

An antigen or antigenic composition can be obtained from autoantigens, allergens, etc.

An antigen can be a whole cell extract, a cell lysates, a whole cell, a whole live cell, a whole inactivated cell, a whole irradiated cell, etc. Antigens may be crude, purified, or recombinant form. In some cases, an antigen is at least 50% pure, at least 60% pure, at least 70% pure, at least 80% pure, at least 90% pure, at least 95% pure, at least 98% pure, or at least 99% pure, or more than 99% pure.

An antigen can be chemically, enzymatically, or genetically coupled to CC. In some cases, an antigen is present in an immunomodulatory composition of the present disclosure in admixture with CC.

An immunomodulatory composition of the present disclosure can comprise a single type of antigen. An immunomodulatory composition of the present disclosure can include 2 or more different antigens. An immunomodulatory composition of the present disclosure can include 2, 3, 4, 5, 6, or more than 6, different antigens. Where an immunomodulatory composition of the present disclosure includes more than one antigen, the more than one antigen can be from the same cell or allergen. Where an immunomodulatory composition of the present disclosure includes more than one antigen, the more than one antigen can be from two or more cells, or allergens.

An antigen can be in the form of a protein, a lipopolysaccharide, a lipoprotein, a proteoglycan, glycoproteins, glycosaminoglycans, an oligosaccharide, etc.

An antigen can be in the form of a nucleic acid comprising a nucleotide sequence encoding an antigen, e.g., a polypeptide antigen. For example, an antigen can be provided in the form of DNA (e.g., plasmid DNA, naked DNA etc.), RNA, and/or a wild-type, attenuated and/or recombinant vector-based nucleic acid. The nucleic acid coding for the antigen can be either "naked" or contained in a delivery system, such as liposomes.

A recombinant vector-encoded antigen can be at least one recombinant expression construct which comprises a promoter operably linked to a nucleotide sequence encoding an antigen in recombinant viral vectors (such as adenovirus (e.g. Ad2, Ad4, Ad5, Ad35, Ad35K5 etc.), adeno-associated virus, lentivirus, herpes virus, poxvirus, vesicular stomatitis virus, alpha virus, measles virus, *papaya* mosaic virus, cytomegalovoirus, modified vaccinia Ankara virus MVA, polio virus, Marba virus etc.), bacterial vector vaccines (such as *Salmonella, Shigella, E. coli, Lactococcus lactis, Listeria* sp., *Lactobacillus* sp.), fungal vectors (such as heat killed recombinant *Saccharomyces* yeast), plant viruses, virus-like particles (VLPs), virosomes, synthetic vaccine particles, synthetic biomimetic supramolecular biovectors, depathogenized viral/bacterial strains (such as NIBRG14 from H5N1). The vector could be in the form of live wild-type, non-replicative, mutated, modified, defective or attenuated. The vectors could be from human, animal, plant or prokaryote origin and in any effective amount.

In treating or preventing autoimmune diseases or allergy, antigen can be given at the same or different times, at the same or different site than the immunomodulatory composition of the present disclosure.

Autoantigens

In some cases, an immunomodulatory composition of the present disclosure comprises, in addition to CC, an autoantigen. In some cases, an immunomodulatory composition of the present disclosure comprises, in addition to CC, one or more autoantigens, e.g., 1, 2, 3, 4, 5, or more antigens, from one or more self tissues.

For example, where the autoimmune disease is type 1 diabetes, an antigen can be pancreatic islet beta cell associated antigen, proinsulin, glutamic acid decarboxylase, chromogranin A, islet amyloid polypeptide, HSP60; for systemic lupus erythematosus, an antigen can be snRNP; for Grave's disease, an antigen can be thyroglobulin, thyrotropin receptor or a thyroid epithelial cell; for thrombocytopenic purpura, an antigen can be a platelet, GPIIB/IIIa; for multiple sclerosis, an antigen can be myelin basic protein, MOG, PLP; for celiac disease, an antigen can be transglutaminidase.

A suitable autoantigen can be an autoantigen involved in the initiation and/or propagation of an autoimmune disease, the pathology of which can be due to the presence of antibodies specific for a molecule expressed by the relevant target organ, tissue, or cells, e.g., systemic lupus erythematosus (SLE) or myasthenia gravis (MG). In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens that can be included in a subject immunomodulatory composition include, without limitation: (a) with respect to SLE, the Smith protein, RNP ribonucleoprotein, and the SS-A and SS-B proteins; and (b) with respect to MG, the acetylcholine receptor. Examples of other antigens involved in one or more types of autoimmune response include, e.g., endogenous hormones such as luteinizing hormone, follicular stimulating hormone, testosterone, growth hormone, prolactin, and other hormones.

Other examples of suitable autoantigens include antigens associated with neurological diseases such as schizophrenia, Alzheimer's disease, depression, hypopituitarism, and cardiovascular diseases such as atherosclerosis (e.g., an antigen for atherosclerosis can be cholesteryl ester transfer protein, oxidized LDL, apoB210, apoB100) etc.

Those of skill in the art will recognize that other suitable autoantigens include those that are associated with juvenile rheumatoid arthritis and Marie-Strumpell ankylosing spondylitis, that can lead to anterior uveitis and subsequent glaucoma. Other suitable autoantigens include those that are associated with Huntington's disease, and Parkinson's disease.

Examples of autoantigens include those that are associated with cell or organ-specific autoimmunity. Such autoantigens include the acetylcholine receptor, associated with Myasthenia gravis; actin, associated with chronic active hepatitis and primary biliary cirrhosis; adenine nucleotide translocator (ANT), associated with dilated cardiomyopathy and myocarditis; β-adrenoreceptor, associated with dilated cardiomyopathy; aromatic L-amino acid decarboxylase, associated with autoimmune polyendocrine syndrome type I (APS-I); asialoglycoprotein receptor, associated with autoimmune hepatisis; bactericidal/permeability-increasing protein (Bpi), associated with cystic fibrosis vasculitides; calcium-sensing receptor, associated with acquired hypoparathryoidism; cholesterol side-chain cleavage enzyme (CYPIIa), associated with APS-I; collagen type IV $\alpha_3$-chain; associated with Goodpasture syndrome; cytochrome P450 2D6 (CYP2D6), associated with autoimmune hepatisis; desmin, associated with Crohn disease and coronary artery disease; desmoglein 1, associated with pemphigus foliaceus; desmoglein 3, associated with pemphigus vulgaris; F-actin, associated with autoimmune hepatitis; GM gangliosides, associated with Guillain-Barré syndrome; glutamate decarboxylase (GAD65), associated with type 1 diabetes and stiff man syndrome; glutamate receptor (GLUR), associated with Rasmussen encephalitis; H/K ATPase, associated with autoimmune gastritis; 17-α-hydroxylase (CYP17), associated with APS-I; 21-hydroxylast (CYP21), associated with Addison disease; IA-2 (ICA512), associated with type 1 diabetes; insulin, associated with type 1 diabetes and insulin hypoglycemic syndrome (Hirata disease); insulin receptor, associated with type B insulin resistance, acanthosis and systemic lupus erythematosus (SLE); intrinsic factor type 1, associated with pernicious anemia, leukocyte function-associated antigen (LFA-1), associated with treatment-resistant Lyme arthritis; myelin-associated glycoprotein (MAG), associated with polyneuropathy; myelin basic protein, associated with multiple sclerosis and demyelinating diseases; myelin oligodendrocyte glycoprotein (MOG), associated with multiple sclerosis; myosis, associated with rheumatic fever; p-80-coilin, associated with atopic dermatitis; pyruvate dehydrogenase complex-E2 (PDC-E2), associated with primary biliary cirrhosis; sodium iodid symporter (NIS), associated with Graves disease and autoimmune hypothyroidism; SOX-10, associated with vitiligo; thyroid and eye muscle shared protein, associated with thyroid associated ophthalmopathy; thyroglobulin, associated with autoimmune thyroiditis; thyroid peroxidase, associated with autoimmune Hashimoto thyroiditis; thyrotropin receptor, associated with Graves disease; tissue transglutaminase, associated with coeliac disease; transcription coactivator p75, associated with atopic dermatitis; tryptophan hydroxylase, associated with APS-I; tyrosinase, associated with vitiligo and metastatic melanoma; and tyrosine hydroxylase, associated with APS-I.

Examples of autoantigens include those that are associated with systemic autoimmunity. Such autoantigens include ACTH, associated with ACTH deficiency; aminoacyl-tRNA histidyl synthetase, associated with myotitis and dermatomyositis; aminoacyl-tRNA synthetase (several), associated with polymyositis and dermatomyositis; cardiolipin, associated with SLE; carbonic anhydrase II, associated with SLE, Sjögren syndrome and systemic sclerosis; collagen (multiple types), associated with rheumatoid arthritis (RA), SLE and progressive systemic sclerosis; centromere-associated proteins, associated with systemic sclerosis; DNA-dependent nucleosome-stimulated ATPase, associated with dermatomyositis; fibrillarin, associated with scleroderma; fibronectin, associated with SLE, RA and morphea; glucose-6-phosphate isomerase, associated with RA; β2-glycoprotein I (β2-GPI), associated with primary antiphospholipid syndrome; golgin (95, 97, 160, 180), associated with Sjögren syndrome, SLE and RA; heat shock protein, associated with various immune-related disorders; hemidesmosomal protein 180, associated with bullous pemphigoid, herpes gestationis and cicatricial pemphigoid; histone H2A-H2B-DNA, associated with SLE; IgE receptor, associated with chronic idiopathic urticaria; keratin, associated with RA; Ku-DNA-protein kinase, associated with SLE; Ku-nucleoprotein, associated with connective tissue syndromes; La phosphoprotein (La 55-B), associated with Sjögren syndrome; myeloperoxidase, associated with necrotizing and crescentic glomerulonephritis and systemic vasculitis; proteinase 3 (PR3), associated with Wegener granulomatosis and Churg-Strauss syndrome; RNA polymerase I-III (RNP), associated with systemic sclerosis and SLE; signal recognition protein (SRP54), associated with polymyositis; topoisomerase-I (Scl-70), associated with scleroderma and Raynaud syndrome; tubulin, associated with chronic liver disease and visceral leishmaniasis; and vimentin, associated with systemic autoimmune disease.

Other examples of autoantigens include those that are associated with plasma protein and cytokine autoimmunity. Such autoantigens include C1 inhibitor, associated with autoimmune C1 deficiency; C1q, associated with SLE and membrane proliferative glomerulonephritis (MPGN); cytokines (IL-1α, IL-1β, IL-6, IL-10, LIF), associated with RA and systemic sclerosis; factor II, factor V, factor VII, factor VIII, factor IX, factor X, factor XI, factor XII, thrombin, vWF, associated with prolonged coagulation time; glycoprotein IIb/IIIg and 1B/IX, associated with autoimmune thrombocytopenia purpura; IgA, associated with immunodeficiency; and oxidized LDL (OxLDL), associated with artherosclerosis.

Yet more examples of autoantigens include those that are associated with cancer and paraneoplastic autoimmunity.

Such autoantigens include amphiphysin, associated with neuronopathy and small lung cell cancer; cyclin B1, associated with hepatocellular carcinoma; DNA topoisomerase II, associated with liver cancer; desmoplakin, associated with paraneoplastic pemphigus; gephyrin, associated with paraneoplastic stiff man syndrome; Hu proteins, associated with paraneoplastic encephalomyelitis; neuronal nicotinic acetylcholine receptor, associated with subacute autonomic neuropathy and cancer; p53, associated with cancer and SLE; p62 (IGF-II mRNA-binding protein), associated with hepatocellular carcinoma (China); recoverin, associated with cancer-associated retinopathy; Ri protein, associated with paraneoplastic opsoclonus myoclonus ataxia; β IV spectrin, associated with lower motor neuron syndrome; synaptotagmin, associated with Lambert-Eaton myasthenic syndrome; voltage-gated calcium channels, associated with Lamber-Eaton myasthenic syndrome; and Yo protein, associated with paraneoplastic cerebellar degeneration.

Allergens

In some cases, an immunomodulatory composition of the present disclosure comprises, in addition to CC, an allergen. Suitable allergens can be obtained and/or produced using known methods. Classes of suitable allergens include, but are not limited to, pollens, animal dander other than cat dander, grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; epidermal allergens can be obtained from house or organic dusts (typically fungal in origin), from arthropods such as house mites (*Dermatophagoides pteronyssinus*), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major and cryptic epitopes of the Der p I allergen (Hoyne et al. (1994) Immunology 83190-195), bee venom phospholipase A2 (PLA) (Akdis et al. (1996) J. Clin. Invest. 98:1676-1683), birch pollen allergen Bet v 1 (Bauer et al. (1997) Clin. Exp. Immunol. 107:536-541), and the multi-epitopic recombinant grass allergen rKBG8.3 (Cao et al. (1997) Immunology 90:46-51). These and other suitable allergens are commercially available and/or can be readily prepared as extracts following known techniques.

Suitable allergens include tree pollen allergens, weed pollen allergens, herb pollen allergens, grass pollen allergens, mite allergens, insect allergens, venom allergens, animal hair allergens, dander allergens and food allergens.

In some cases, the allergen is in the form of an extract, a purified allergen, a modified allergen or a recombinant allergen or a mutant of a recombinant allergen or any combination thereof. In some cases, the allergen is selected from the group consisting of grass pollen allergen, dust mite allergen, ragweed allergen, cat allergen and birch allergen.

An allergen can be present in an immunomodulatory composition of the present disclosure in an amount of from about 2.5 μg to about 75 μg per unit dosage form. For example, an allergen can be present in an immunomodulatory composition of the present disclosure in an amount of from about 2.5 μg to about 5 μg, from about 5 μg to about 10 μg, from about 10 μg to about 15 μg, from about 15 μg to about 20 μg, from about 20 μg to about 25 μg, from about 25 μg to about 50 μg, or from about 50 μg to about 75 μg, or more than 75 μg, per unit dosage form.

In some cases, a dose of an immunomodulatory composition of the present disclosure that comprises an allergen has a potency of about 65 to about 17,600 Biological Allergen Units (BAU). In some cases, a dose of an immunomodulatory composition of the present disclosure that comprises an allergen comprises from about 650 BAU to about 6,000 BAU.

Antibodies

In some cases, an immunomodulatory composition of the present disclosure comprises, in addition to CC, an antibody against a cancer antigen, an autoantigen, an allergen or a pathogenic antigen (e.g., a therapeutic antibody, monoclonal antibodies, bispecific antibodies, chemoimmuno conjugated antibodies, radioimmunoconjugated antibodies, antibody-cytokine fusion proteins, antibody-antigen fusion proteins, antibody-immunotoxin fusion protein etc.).

Antibodies that can be included in an immunomodulatory composition of the present disclosure include, without limitation, antibodies directed against co-stimulatory or co-inhibitory molecules (CD28, CD40, C7LA-4, PD-1, PDL-1, GITR, VISTA, LAG-3, ICOS, CD137, OX40, CD137, CD227, CTLA-4, KIRs, TCR, TIM3 etc.); and other therapeutic antibodies.

Non-limiting examples of suitable antibodies include, but are not limited to, adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumornab, pertuzumab, ranibizumab, rituximab, rovelizumab, tocilizumab, tositumomab, trastuzumab, ustekinumab, vedolizomab, zalutumumab, and zanolimumab.

Non-limiting examples of therapeutic and prophylactic antibodies that can be used in combination with an immunomodulatory composition of the present disclosure include MDX-O10 (Medarex, NJ.) which is a humanized anti-CTLA-4 antibody for the treatment of prostate cancer; SYNAGIS™ (MedImmune, Md.) which is a humanized anti-respiratory syncytial virus (RSV) monoclonal antibody for the treatment of RSV infection; and HERCEPTIN™ (Trastuzumab) (Genentech, Calif.) which is a humanized anti-HER2 monoclonal antibody for the treatment of metastatic breast cancer. Other examples are humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti-Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti-CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Scbering); SB-240563 and SB-240683 are humanized anti-IL-5 and IL-4 antibodies, respectively, (SmithKline Beecham); rhuMab-E25 is a humanized anti-IgE IgG1 antibody (Genentech/NorvartisfTanox Biosystems); ABX-CBL is a murine anti CD-147 IgM antibody (Abgenix); BTI-322 is a rat anti-CD2 IgG antibody (MedImmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor). The above-listed immunoreactive reagents, as well as any other immunoreactive reagents, may be administered according to any regimen known to those of skill in the art, including the regimens recommended by the suppliers of the immunoreactive reagents.

Other examples of therapeutic and prophylactic antibodies that can be used in combination with an immunomodulatory composition of the present disclosure include Humira and Remicade; ACTEMRA™ (Genentech) which is a recombinant monoclonal IgG1 anti-human interleukin 6-receptor antibody for the treatment of anti-TNF resistant rheumatoid arthritis (RA) and juvenile idiopathic arthritis (JIA); ARZERRA™ (GlaxoSmithKline/Novartis) which is a chimeric human monoclonal antibody directed against membrane proximal epitope on the CD20 molecule for the treatment of RA; BENLYSTA™ (GlaxoSmithKline) which is a human monoclonal IgG1 gamma that binds to and inhibits the soluble form of the B-lymphocyte stimulator (BLyS) protein for the treatment of SLE; ORENCIA™ (Bristol-Myers Squibb) which is a CTLA-4 IgG1 binding to CD80/86 on antigen-presenting cells inhibiting the co-stimulation of CD28 on the T cells for the treatment of RA, JIA and SLE; SIMPONI (Janssen) which is a IgG1 monoclonal antibody acting on both soluble and membrane-bound TNF-α for the treatment of RA, psoriatic arthritis (PsA) and ankylosing spondylitis (AS); CIMZIA™ (UCB Group) which is a pegylated humanized antibody Fab' fragment of the TNF-α monoclonal antibody for the treatment of RA; Sifalimumab (MedImmune) which is an anti-IFN-α monoclonal antibody designed for the treatment of SLE, dematomyositis and polymyositis; various intravenous immunoglobulin products which are pools of immunoglobulins from healthy individuals for the treatment of SLE, systemic sclerosis and vasculitis; KINERE™ (Swedish Oprhan Biovitrum AB), ILARIS™ (Novartis) and ARCALYST™ (Regeneron) which are interleukin-1 blockers for the treatment of RA and cryopyrin-associated periodic syndrome (CAPS).

In some cases, an immunomodulatory composition of the present disclosure comprises, in addition to CC, a cytokine. Cytokines that can be included in an immunomodulatory composition of the present disclosure include, without limitation, interleukins, transforming growth factors (TGFs), fibroblast growth factors (FGFs), platelet derived growth factors (PDGFs), epidermal growth factors (EGFs), colony stimulating factors (CSFs), connective tissue activated peptides (CTAPs), osteogenic factors, and biologically active analogs, fragments, and derivatives of such growth factors. Suitable cytokines include BIT-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, 1L4, IL5, IL6, IL7, IL8, IL9, IL10, IL11, IL12, IL13, IL14, IL15, IL16, IL17, IL18, IL22, etc., leptin, myostatin, macrophage stimulating protein, platelet-derived growth factor, tumor necrosis factor (TNF)-alpha (TNF-α), TNF-β, nerve growth factor (NGF), CD40L, CD137L/4-1BBL, human lymphotoxin-β, G-CSF, M-CSF, GM-CSF, platelet-derived growth factor (PDGF), IL-1α, IL1-β, IP-10, PF4, GRO, 9E3, erythropoietin, endostatin, angiostatin, vascular endothelial growth factor (VEGF) or any fragments or combinations thereof. Other cytokines include members of the transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); hematopoietic growth factors (Flt3); pituitary growth hormones or derivatives; growth hormones, neuroactive hormones, Inhibins (for example, Inhibin A, Inhibin B); differentiation factors (for example, GDF-1); and Activins (for example, Activin A, Activin B, Activin AB). In some cases, an immunomodulatory composition of the present disclosure comprises, in addition to CC, a compound or agent modulating cytokines.

Adjuvants

An immunomodulatory composition of the present disclosure can comprise, in addition to CC, one or more adjuvants.

Exemplary adjuvants include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12, IL-15, IL-28, etc.) (WO99/44636), etc.), interferons (e.g. gamma interferon), macrophage colony stimulating factor (M-CSF), tumor necrosis factor (TNF), colony-stimulating factors (e.g., GM-CSF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; WO 96/02555, WO 98/16247, WO 98/18810, WO 98/40100, WO 98/55495, WO 98/37919 and WO 98/52581), i.e., oligonucleotides containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+ 3dMPL+IM2 (optionally including a sterol) e.g. WO 98/57659; (14) alphaGalCer and its derivatives; (16) toll-like receptor (TLR) agonists, NOD-like receptor (NLR) agonists, RIG-I agonists, agonists for C-type lectin receptors and other pathogen recognition receptor (PRR) agonists e.g., CpG ODNs, ISS-ODNs, rinatolimod, polyI:C and its derivatives, flagellin, ampligen, imidazoquinalines (e.g., imiquimod, resiquimod), muramyl dipeptides; (17) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human included in some cases.

Further exemplary adjuvants include, but are not limited to: cholera toxin B subunit, BCG, *Pseudomonas aeruginosa* exoprotein A, tocopherol, HBV core, *E. coli* heat labile toxins (such as LT-A, LT-B), Pertussis toxin, Diphtheria toxoid, tetanus toxoid, Cholera toxin derived (CTA1-DD, CT), mutant LT and CT, Aluminium salt-based adjuvants (such as Alum, Aluminum phosphate, Aluminum sulphate, Alhydrogel), Calcium phosphate, kaolin, monophosphoryl lipid A (MPLR) and its derivatives, glucoppyranosyl lipid A, synthetic lipid A, Lipid A mimetics, Vitamin E, Depovaxn™, Saponins (Quil-A, AS01, AS02 (squalene+ MPL+QS-21)), AS03, AS04 (alum+MPL®), Tomatin, Protolin, RC-529, Pluronic™, Monatides, Matrix-M, OM-174, Lipovac, IC-31, bacterial/mycobacterial peptides (such as KLK, cationic (poly)peptides, anti-bacterial microbial peptides, defensins, tuftsin, cathelicidin), dipeptides (such as pidotimod), Bestatin, Hepon (tetradecapeptide), SCV-07 (gamma-D-glutamyl-L-tryptophan), Thymosin-a, Immunofan, Thymogen, Indolicidin and its derivatives, polyphosphagene and its derivatives, Gellan, nucleotides (mononucleotides, dinucleotides, polynucleotides, cyclic nucleotides), Eurocine etc.

An immunomodulatory composition of the present disclosure can comprise, in addition to CC, one or more mucoadhesives such as sodium alginate, starch, lectins, thiolated polymers, GelVac™, sodium carboxymethylcellulose, hydroxylpropyl methylcellulose, carbomers, cetyl trimethyl ammonium bromide.

An immunomodulatory composition of the present disclosure can comprise, in addition to CC, one or more adjuvant formulations such as oil-in-water emulsions, water-in-oil emulsions, nanoemulsions, particulate delivery systems, liposomes, microspheres, biodegradable microspheres, patches virosomes, proteoliposomes, proteasomes, Immunostimulatory complexes (ISCOMs, ISCOMATRIX), microparticles, nanoparticles, biodegradable nanoparticles, silicon nanoparticles, polymeric micro/nano particles, polymeric lamellar substrate particles (PLSP), microparticle resins, nanolipogels, synthetic/biodegradable and biocompatible semisynthetic or natural polymers or dendrimers (such as PLG, PLGA, PLA, polycaprolactone, silicone polymer, polyesters, poly-dimethyl siloxane, sodium polystyrene sulphonate, polystyrene benzyl trimethyl ammonium chloride, polystyrene divinyl benzene resin, polyphosphazene, poly-[di-(carboxylactophenoxy)phosphazene] (PCPP), poly-(methylmethacrylate), dextran, polyvinylpyrrolidone, hyaluronic acid and derivatives, chitosan and its derivatives, polysaccharides, Delta inulin polysaccharide, glycolipids (synthetic or natural), lipopolysaccharides, polycationic compound(s) (such as Poly-amino acids, poly-(γ-glutamic acid), poly-arginine-HCl, poly-L-lysine, polypeptides, biopolymers), cationic dimethyldioctadecyl ammonium (DDA), alpha-galactosyl ceramide and its derivatives, archaeal lipids and derivatives, lactanes, gallen, glycerolipids, phospholipids, cochleates, etc. or mixtures thereof.

An immunomodulatory composition of the present disclosure can comprise, in addition to CC, one or more adjuvant formulations such as oil-in-water emulsions or water-in-oil emulsions including edible oils (such as olive oil, mustard oil, vegetable oil, soybean oil, mineral oil etc.).

An immunomodulatory composition of the present disclosure can comprise, in addition to CC, one or more surfactants and detergents (e.g., non-ionic detergents or niosomes) (such as Tween-80, Polysorbate 80, Span 85, Stearyl tyrosine etc.). An immunomodulatory composition of the present disclosure can comprise, in addition to CC, an component or adjuvant mentioned above which provides a depot effect.

Probiotic

An immunomodulatory composition of the present disclosure can comprise, in addition to CC, one or more probiotics. "Probiotic" refers to a composition containing one species (i.e., a single isolate) or a combination of pure bacteria (i.e., co-culture of desired bacteria), and may also include any additional carriers, excipients, and/or therapeutic agents that can be administered to a mammal for restoring microbiota and/or providing health benefits. Examples of probiotics include but are not limited to, *Lactobacillus* sp., *Bifidobacteria* sp., *Saccharomyces boulardii, Streptococcus* sp., *Enterococcus faecium, Bacillus coagulans, Faecalibacterium* sp., etc.

Prebiotic

An immunomodulatory composition of the present disclosure can comprise, in addition to CC, one or more prebiotic. As used herein the term "prebiotic" refers to nutritional supplements that are not digested by the mammal that ingests them, but which are a substrate for the growth or activity of the microbiota, particularly the gut microbiota. Many prebiotics are carbohydrates, e.g. polysaccharides and oligosaccharides, but the definition does not preclude non-carbohydrates. The most prevalent forms of prebiotics are nutritionally classed as soluble fiber. Prebiotics may provide for changes in the composition and/or activity of the gastrointestinal microbiota. "Prebiotic" also refers to compositions containing non-viable food components that are specifically metabolized in the body by indigenous bacteria thought to be of positive value such as *Bifidobacteria, Lactobacillus*, etc. Examples of prebiotics include but are not limited to fructose, xylose, soya, glucose, mannose etc.

Microbiota

The term "microbiota", "microbiome", "symbiotic" or "commensal" used interchangeably, refers to microbial population (bacteria, viruses, fungi, parasites) in an individual at various places such as gut, skin, saliva, colon, vagina, lungs etc. A dysbalance in microbiota is related to the etiology or onset of several autoimmune and inflammatory diseases. An immunomodulatory composition of the present disclosure can comprise, in addition to CC, members of microbiota of an individual such as *Bacteroidetes, Proteobacteria, Firmicutes, Verrucomicrobia, Bacteriodales, Enterobacteriales, Clostridium*, etc. Other examples of members of microbiota are known, or will be apparent, to those skilled in the art. See, US Patent Application No. 2014/0010844. See, Howarth and Wang, *Nutrients*. 2013, 5(1):58-81 for a description of the role of endogenous microbiota, probiotics and their biological products. Thus a composition of the invention can be used to establish, modulate, regulate or maintain a balanced microbiota. Members of the microbiome can be of autologous, allogeneic and xenogeneic origin, wild-type, viable, inactivated, heat-killed, mutated, attenuated and/or genetically engineered.

Therapeutic Pathogens

An immunomodulatory composition of the present disclosure can comprise, in addition to CC, therapeutic pathogenic bacteria, virus, fungus etc. such as *Listeria, Saccharomyces, Escherichia, Salmonella, Staphylococcus, Klebsiella*, poxviruses, adenoviruses, oncolytic viruses. Other examples of therapeutic microbial pathogens are known, or will be apparent, to those skilled in the art. See, US Patent Application No. 2014/0010844. Therapeutic pathogen can be wild-type, viable, inactivated, heat-killed, mutated, attenuated and/or genetically engineered.

Therapeutic Agents

An immunomodulatory composition of the present disclosure can comprise, in addition to CC, one or more therapeutic agents. Examples of therapeutic agents are known, or will be apparent, to those skilled in the art. Non-limiting examples of the therapeutic agents are provided herein the "Methods" section, which include anti-inflammatory agents, anti-proliferative agents, immunosuppressive agents, anti-histamines, immunoregulatory agents, immunomodulatory agents, antimetabolic agents, anti-allergic agents, cytotoxic agents, anti-helminth agents, anti-angiogenic agents, antimicrobial agents (such as antiviral agents, antibacterial agents, anti-parasitic agents, antimalarial agents, anti-protozoal agents), therapeutic peptides etc.

Methods

The present disclosure provides methods of modulating an immune response in an individual, the method comprising administering to the individual an effective amount of an immunomodulatory composition of the present disclosure. The present disclosure provides methods of reducing an undesired immune response in an individual, the method comprising administering to the individual an effective amount of an immunomodulatory composition of the present disclosure. The present disclosure provides methods of reducing inflammation in an individual, the method comprising administering to the individual an effective amount of an immunomodulatory composition of the present disclosure. The present disclosure provides methods of treating an autoimmune disorder in an individual, the method comprising administering to the individual an effective amount of an immunomodulatory composition of the present disclosure. The present disclosure provides methods of treating an allergy (allergic disease) in an individual, the method comprising administering to the individual an effective amount of an immunomodulatory composition of the present disclosure. The present disclosure provides methods of treating a metabolic disease in an individual, the method comprising administering to the individual an effective amount of an immunomodulatory composition of the present disclosure. The present disclosure provides methods of treating a neurological disorder in an individual, the method comprising administering to the individual an effective amount of an immunomodulatory composition of the present disclosure. The present disclosure provides methods of enhancing the efficacy and/or reducing the toxicity of therapeutic treatment in an individual, the method comprising administering to the individual an effective amount of an immunomodulatory composition of the present disclosure. The present disclosure provides methods of treating, restoring or correcting disease- or medical condition-related to imbalances in the microbiome of an individual, the method comprising administering to the individual an effective amount of an immunomodulatory composition of the present disclosure. The present disclosure provides methods of treating, restoring or correcting dysbiosis of an individual, the method comprising administering to the individual an effective amount of an immunomodulatory composition of the present disclosure.

The present disclosure also provides a method of modulating dendritic cells, the method comprising: a) contacting dendritic cells (DCs) obtained from an individual with a composition comprising: i) *Caulobacter crescentus*; and/or ii) an antigen; the contacting step is in vitro, and modulates antigen presentation of the antigen on the DCs, thereby generating a population of modulated DCs. The population of modulated DCs can then be administered to the individual from whom the DCs were obtained.

In some cases, various immune cells can be obtained from lymphoid tissues, peripheral blood, organs and tissues, and/or can be differentiated from stem cells obtained from bone marrow or various organs.

The present disclosure also provides a method of inducing proliferation, differentiation and/or modulation of stem cells, the method comprising contacting stem cells obtained from an individual with a composition comprising *Caulobacter crescentus*. Contacting the stem cells with the CC leads to proliferation, differentiation and/or modulation of the stem cells, thereby generating a population of expanded, differentiated and/or modulated cells. The population of expanded, differentiated and/or modulated cells can then be administered to the individual from whom the stem cells were obtained.

The present disclosure further provides a method of generating regulatory lymphocytes such as NK, NKT, γδ T cells, ILCs, T cells, and B cells, the method comprising: a) contacting lymphocytes (NK, NKT, γδ T cells, ILCs, T cells, B cells) obtained from an individual with a composition comprising: i) *Caulobacter crescentus*; and/or ii) an antigen in the presence or absence of antigen presenting cells. Contacting the lymphocytes with the CC generates regulatory lymphocytes, thereby generating a population of regulatory lymphocytes. The population of regulatory lymphocytes can then be administered to the individual from whom the lymphocytes were obtained.

Methods of Modulating an Immune Response

The present disclosure provides methods of modulating an immune response in an individual, the method comprising administering to the individual an effective amount of an immunomodulatory composition of the present disclosure. The present disclosure provides methods of reducing an undesired immune response in an individual, the method comprising administering to the individual an effective amount of an immunomodulatory composition of the present disclosure. The present disclosure provides methods of reducing inflammation in an individual, the method comprising administering to the individual an effective amount of an immunomodulatory composition of the present disclosure. The present disclosure provides methods of treating an autoimmune disorder in an individual, the method comprising administering to the individual an effective amount of an immunomodulatory composition of the present disclosure. The present disclosure provides methods of treating an allergy (allergic disease) in an individual, the method comprising administering to the individual an effective amount of an immunomodulatory composition of the present disclosure.

In some cases, the immune response is a humoral immune response. In some cases, the present disclosure provides methods of modulating a humoral immune response in an individual, the method comprising administering to the individual an effective amount of an immunomodulatory composition of the present disclosure. In some cases, the immunomodulatory composition does not include any additional antigens (other than antigens present on CC). In some cases, the immunomodulatory composition comprises an antigen (e.g., an antigen other than antigens present on CC). As described above, suitable antigens include autoantigens, and allergens.

In some cases, the immune response is a cellular immune response. In some cases, the present disclosure provides methods of modulating a cellular immune response in an individual, the method comprising administering to the individual an effective amount of an immunomodulatory composition of the present disclosure. In some cases, the immunomodulatory composition does not include any additional antigens (other than antigens present on CC). In some cases, the immunomodulatory composition comprises an antigen (e.g., an antigen other than antigens present on CC). As described above, suitable antigens include autoantigens and allergens.

In some cases, the immune response comprises a modulation in the number of B cells. In some cases, a subject method comprising administering to an individual in need thereof an effective amount of an immunomodulatory composition, where an effective amount of an immunomodulatory composition is an amount that, when administered to the individual in a single dose or in multiple doses, is effective to modulate (e.g., reduce) the number of B cells in an individual. For example, in some cases, an effective amount of an immunomodulatory composition of the present disclosure is an amount that is effective, when administered in a single dose or in multiple doses, to modulate (e.g., reduce) the number of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of B cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number of antigen-specific B cells in an individual. For example, in some cases, an effective amount of an immunomodulatory composition of the present disclosure is an amount that is effective, when administered in a single dose or in multiple doses, to modulate (e.g., reduce) the number of antigen-specific B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the number of antigen-specific B cells in the individual in the absence of treatment with the immunomodulatory composition. For example, in some cases, an effective amount of an immunomodulatory composition of the present disclosure is an amount that is effective, when administered in a single dose or in multiple doses, to reduce the number of antigen-specific B cells in an individual by at least 10%, at least 15%, at least 20%, at least 25%, at least 30%, at least 35%, at least 40%, at least 45%, at least 50%, at least 75%, or more than 75%, compared to the number of antigen-specific B cells in the individual in the absence of treatment with the immunomodulatory composition. For example, in some cases, an effective amount of an immunomodulatory composition of the present disclosure is an amount that is effective, when administered in a single dose or in multiple doses, to reduce the number of autoantigen-specific B cells in an individual by at least 10%, at least 15%, at least 20%, at least 25%, at least 30%, at least 35%, at least 40%, at least 45%, at least 50%, at least 75%, or more than 75%, compared to the number of autoantigen-specific B cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) activation of B cells in an individual. For example, in some cases, an effective amount of an immunomodulatory composition of the present disclosure is an amount that is effective, when administered in a single dose or in multiple doses, to modulate (e.g., reduce) activation of B cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, at least 25-fold, at least 50-fold, at least 100-fold, or more than 100-fold, compared to the activation level of B cells in the individual in the absence of treatment with the immunomodulatory composition. For example, in some cases, an effective amount of an immunomodulatory composition of the present disclosure is an amount that is effective, when administered in a single dose or in multiple doses, to reduce the activation of B cells in an individual by at least 10%, at least 15%, at least 20%, at least 25%, at least 30%, at least 35%, at least 40%, at least 45%, at least 50%, at least 75%, or more than 75%, compared to the activation level of B cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the amount of antibody specific to a given antigen in the individual. For example, in some cases, an effective amount of an immunomodulatory composition of the present disclosure is an amount that is effective, when administered in a single dose or in multiple doses, to modulate (e.g., reduce) the amount of antibody specific to a given antigen in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of antibody specific to the antigen in the individual in the absence of treatment with the immunomodulatory composition. For example, in some cases, an effective amount of an immunomodulatory composition of the present disclosure is an amount that is effective, when administered in a single dose or in multiple doses, to reduce the amount of antibody specific to a given antigen in an individual by at least 10%, at least 15%, at least 20%, at least 25%, at least 30%, at least 35%, at least 40%, at least 45%, at least 50%, at least 75%, or more than 75%, compared to the amount of antibody specific to the antigen in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) production of one or more cytokines in the individual. For example, in some cases, an effective amount of an immunomodulatory composition of the present disclosure is an amount that is effective, when administered in a single dose or in multiple doses, to modulate (e.g., reduce) production of one or more cytokines in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of the cytokine in the individual in the absence of treatment with the immunomodulatory composition. For example, in some cases, an effective amount of an immunomodulatory composition of the present disclosure is an amount that is effective, when administered in a single dose or in multiple doses, to reduce the production of one or more cytokines in an individual by at least 10%, at least 15%, at least 20%, at least 25%, at least 30%, at least 35%, at least 40%, at least 45%, at least 50%, at least 75%, or more than 75%, compared to the production of one or more cytokines in the individual in the absence of treatment with the immunomodulatory composition. In other cases, an effective amount of an immunomodulatory composition of the present disclosure is an amount that is effective, when administered in a single dose or in multiple doses, to modulate (e.g., reduce) production of GM-CSF in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of GM-CSF in the individual in the absence of treatment with the immunomodulatory composition. For example, in some cases, an effective amount of an immunomodulatory composition of the present disclosure is an amount that is effective, when administered in a single dose or in multiple doses, to reduce the production of GM-CSF in an individual by at least 10%, at least 15%, at least 20%, at least 25%, at least 30%, at least 35%, at least 40%, at least 45%, at least 50%, at least 75%, or more than 75%, compared to the amount of GM-CSF in the individual in the absence of treatment with the immunomodulatory composition. For example, in some cases, an effective amount of an immunomodulatory composition of the present disclosure is an amount that is effective, when administered in a single dose or in multiple doses, to modulate (e.g., reduce) production of IL-22 in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-22 in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-22 in an individual by at least 10%, at least 15%, at least 20%, at least 25%, at least 30%, at least 35%, at least 40%, at least 45%, at least 50%, at least 75%, or more than 75%, compared to the amount of IL-22 in the individual in the absence of treatment with the immunomodulatory composition. For example, in some cases, an effective amount of an immunomodulatory composition of the present disclosure is an amount that is effective, when administered in a single dose or in multiple doses, to modulate (e.g., reduce) production of interferon (IFN)-α and/or IFN-β and/or IFN-γ in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IFN-α or IFN-β or IFN-γ in the individual in the absence of treatment with the immunomodulatory composition. For example, in some cases, an effective amount of an immunomodulatory composition of the present disclosure is an amount that is effective, when administered in a single dose or in multiple doses, to reduce the production of interferon (IFN)-α and/or IFN-β and/or IFN-γ in an individual by at least 10%, at least 15%, at least 20%, at least 25%, at least 30%, at least 35%, at least 40%, at least 45%, at least 50%, at least 75%, or more than 75%, compared to the amount of interferon (IFN)-α and/or IFN-β and/or IFN-γ in the individual in the absence of treatment with the immunomodulatory composition. For example, in some cases, an effective amount of an immunomodulatory composition of the present disclosure is an amount that is effective, when administered in a single dose or in multiple doses, to modulate (e.g., reduce) production of one or more of IL-17A, IL-2, IL-10, IL-6 and/or TNF-α in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of IL-17A, IL-2, IL-10, IL-6, or TNF-α in the individual in the absence of treatment with the immunomodulatory composition. For example, in some cases, an effective amount of an immunomodulatory composition of the present disclosure is an amount that is effective, when administered in a single dose or in multiple doses, to reduce the production of one or more of IL-17A, IL-2, IL-10, IL-6 and TNF-α in an individual by at least 10%, at least 15%, at least 20%, at least 25%, at least 30%, at least 35%, at least 40%, at least 45%, at least 50%, at least 75%, or more than 75%, compared to the amount of IL-17A, IL-2, IL-10, IL-6 and TNF-α in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-6 in an individual by at least 10%, at least 15%, at least 20%, at least 25%, at least 30%, at least 35%, at least 40%, at least 45%, at least 50%, at least 75%, or more than 75%, compared to the amount of IL-6 in the individual in the absence of treatment with the immunomodulatory composition. For example, in some cases, an effective amount of an immunomodulatory composition of the present disclosure is an amount that is effective, when administered in a single dose or in multiple doses, to reduce the production of IL-1β in an individual by at least 10%, at least 15%, at least 20%, at least 25%, at least 30%, at least 35%, at least 40%, at least 45%, at least 50%, at least 75%, or more than 75%, compared to the amount of IL-1β in the individual in the absence of treatment with the immunomodulatory composition. In some cases, an effective amount of an immunomodulatory composition of the present disclosure is an amount that is effective, when administered in a single dose or in multiple doses, to increase the level of TGF-β in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of TGF-β in the individual in the absence of treatment with the immunomodulatory composition.

In some cases, an effective amount of an immunomodulatory composition of the present disclosure is an amount that is effective, when administered in a single dose or in multiple doses, to modulate (e.g., increase, reduce or balance) production of one or more cytokines, chemokines or lymphotoxins such as but not limited to GM-CSF, IL-2, IL-22, Interferons, IL-1β, TGF-β, IL-17A, IL-2, IL-10, IL-6, IL-5, IL-13, TNF-α, IL-9, IL-28 KC/IL-8, MIP-1α, LTα4, etc. in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, or more than 10-fold, compared to the amount of cytokines, chemokines or lymphotoxins such as but not limited to GM-CSF, IL-2, IL-22, Interferons, IL-1β, TGF-β, IL-17A, IL-2, IL-1β, IL-6, IL-5, IL-13, TNF-α, IL-9, IL-28, KC/IL-8, MIP-1α, LTα4, etc., in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) a Th1 response in an individual. For example, in some cases, an effective amount of an immunomodulatory composition of the present disclosure is an amount that is effective, when administered in a single dose or in multiple doses, to modulate (e.g., reduce) a Th1 response in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the level of the Th1 response in the individual in the absence of treatment with the immunomodulatory composition. For example, in some cases, an effective amount of an immunomodulatory composition of the present disclosure is an amount that is effective, when administered in a single dose or in multiple doses, to reduce the Th1 response in an individual by at least 10%, at least 15%, at least 20%, at least 25%, at least 30%, at least 35%, at least 40%, at least 45%, at least 50%, at least 75%, or more than 75%, compared to the Th1 response in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of CD4+ T cells in an individual. For example, in some cases, an effective amount of an immunomodulatory composition of the present disclosure is an amount that is effective, when administered in a single dose or in multiple doses, to modulate (e.g., reduce) the number and/or activity of CD4+ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD4+ T cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific CD4+ T cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific CD4+ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD4$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of CD4$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of CD4$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific CD4$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific CD4$^+$ T cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of CD8$^+$ T cells in an individual. For example, in some cases, an effective amount of an immunomodulatory composition of the present disclosure is an amount that is effective, when administered in a single dose or in multiple doses, to modulate (e.g., reduce) the number and/or activity of CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of CD8$^+$ T cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific CD8$^+$ T cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific CD8$^+$ T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific CD8$^+$ T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of CD8$^+$ T in an individual by at least 10%, at least 15%, at least 20%, at least 25%, at least 30%, at least 35%, at least 40%, at least 45%, at least 50%, at least 75%, or more than 75%, compared to the number and/or activity of CD8$^+$ T in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific CD8$^+$ T in an individual by at least 10%, at least 15%, at least 20%, at least 25%, at least 30%, at least 35%, at least 40%, at least 45%, at least 50%, at least 75%, or more than 75%, compared to the number and/or activity of antigen-specific CD8$^+$ T in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of autoantigen-specific CD8$^+$ T cells in an individual by at least 10%, at least 15%, at least 20%, at least 25%, at least 30%, at least 35%, at least 40%, at least 45%, at least 50%, at least 75%, or more than 75%, compared to the number and/or activity of autoantigen-specific CD8$^+$ T cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of cytolytic T cells in an individual. For example, in some cases, an effective amount of an immunomodulatory composition of the present disclosure is an amount that is effective, when administered in a single dose or in multiple doses, to modulate (e.g., reduce) the number and/or activity of cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of cytolytic T cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific cytolytic T cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific cytolytic T cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific cytolytic T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of cytolytic T cells in an individual by at least 10%, at least 15%, at least 20%, at least 25%, at least 30%, at least 35%, at least 40%, at least 45%, at least 50%, at least 75%, or more than 75%, compared to the number and/or activity of cytolytic T cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific cytolytic T cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific cytolytic T cells in the individual in the absence of treatment with the immunomodulatory composition.

In some cases, an effective amount of an immunomodulatory composition of the present disclosure is an amount that is effective, when administered in a single dose or in multiple doses, to modulate the number and/or activity of one or more of natural killer (NK) cells, NKT cells, γδ T cells, ILCs, macrophages, and dendritic cells (DCs) in an individual. For example, in some cases, an effective amount of an immunomodulatory composition of the present disclosure is an amount that is effective, when administered in a single dose or in multiple doses, to modulate the number and/or activity of one or more of NK cells, NKT cells, γδ T cells, ILCs, macrophages, and DCs in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of NK cells, NKT cells, γδ T cells, ILCs, macrophages, and DCs in the individual in the absence of treatment with the immunomodulatory composition. For example, in some cases, an effective amount of an immunomodulatory composition of the present disclosure is an amount that is effective, when administered in a single dose or in multiple doses, to modulate the number and/or activity of one or more of NK cells, NKT cells, γδ T cells, ILCs, macrophages, and DCs in an individual by at least 10%, at least 15%, at least 20%, at least 25%, at least 30%, at least 35%, at least 40%, at least 45%, at least 50%, at least 75%, or more than 75%, compared to the number and/or activity of NK cells, NKT cells, γδ T cells, ILCs, macrophages, and DCs in the individual in the absence of treatment with the immunomodulatory composition.

In some cases, an effective amount of an immunomodulatory composition of the present disclosure is an amount that is effective, when administered in a single dose or in multiple doses, to increase, decrease or balance the number and/or function of regulatory cells in an individual. Tregs (regulatory T cells) are CD4 or CD8$^+$, and may also be FoxP3$^+$. Tregs may also be defined by other markers such as PD-1, CTLA-4 etc. Regulatory cells may also be comprised of other innate cells such as NK, NKT, γδ T cells, ILCs, and DCs, and B lymphocytes. NK and NKT can also be FoxP3$^+$ and may also be defined by other markers such as PD-1. For example, in some cases, an effective amount of an immunomodulatory composition of the present disclosure is an amount that is effective, when administered in a single dose or in multiple doses, to modulate the number of regulatory cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared number and/or activity of regulatory cells in the individual in the absence of treatment with the immunomodulatory composition. For example, in some cases, an effective amount of an immunomodulatory composition of the present disclosure is an amount that is effective, when administered in a single dose or in multiple doses, to increase the number of regulatory cells in an individual by at least 10%, at least 15%, at least 20%, at least 25%, at least 30%, at least 35%, at least 40%, at least 45%, at least 50%, at least 75%, or more than 75%, compared to the number of regulatory cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of Th17 cells in an individual. For example, in some cases, an effective amount of an immunomodulatory composition of the present disclosure is an amount that is effective, when administered in a single dose or in multiple doses, to modulate (e.g., reduce) the number and/or activity of Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th17 cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific Th17 cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific Th17 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th17 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of Th17 cells in an individual by at least 10%, at least 15%, at least 20%, at least 25%, at least 30%, at least 35%, at least 40%, at least 45%, at least 50%, at least 75%, or more than 75%, compared to the number and/or activity of Th17 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific Th17 cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific Th17 cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) the number and/or activity of Th22 cells in an individual. For example, in some cases, an effective amount of an immunomodulatory composition of the present disclosure is an amount that is effective, when administered in a single dose or in multiple doses, to modulate (e.g., reduce) the number and/or activity of Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of Th22 cells in the individual in the absence of treatment with the immunomodulatory composition. In some cases, an effective amount of an immunomodulatory composition of the present disclosure is an amount that is effective, when administered in a single dose or in multiple doses, to modulate (e.g., reduce) the number and/or activity of antigen-specific Th22 cells in an individual. For example, in some cases, an effective amount of an immunomodulatory composition of the present disclosure is an amount that is effective, when administered in a single dose or in multiple doses, to modulate (e.g., reduce) the number and/or activity of antigen-specific Th22 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of antigen-specific Th22 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of Th22 cells in an individual by at least 10%, at least 15%, at least 20%, at least 25%, at least 30%, at least 35%, at least 40%, at least 45%, at least 50%, at least 75%, or more than 75%, compared to the number and/or activity of Th22 cells in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of antigen-specific Th22 cells in an individual by at least 10%, at least 15%, at least 20%, at least 25%, at least 30%, at least 35%, at least 40%, at least 45%, at least 50%, at least 75%, or more than 75%, compared to the number and/or activity of antigen-specific Th22 cells in the individual in the absence of treatment with the immunomodulatory composition.

In some cases, an effective amount of an immunomodulatory composition of the present disclosure is an amount that is effective, when administered in a single dose or in multiple doses, to modulate the number and/or activity of TH9 cells in an individual. "Modulate the number and/or activity" of TH9 cells, as used herein, refers to increasing, decreasing, or balancing the number and/or activity of TH9 cells. For example, in some cases, an effective amount of an immunomodulatory composition of the present disclosure is an amount that is effective, when administered in a single dose or in multiple doses, to modulate the number and/or activity of TH9 cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared number and/or activity of TH9 cells in the individual in the absence of treatment with the immunomodulatory composition.

In some cases, an effective amount of an immunomodulatory composition of the present disclosure is an amount that is effective, when administered in a single dose or in multiple doses, to modulate (e.g., reduce) innate and/or adaptive (including both cellular and humoral) immune responses in an individual. For example, in some cases, an effective amount of an immunomodulatory composition of the present disclosure is an amount that is effective, when administered in a single dose or in multiple doses, to modulate (e.g., reduce) the number and/or activity of innate and/or adaptive immune cells and/or their effector functions in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number and/or activity of one or more of innate or adaptive immune cells and/or their effector functions in the individual in the absence of treatment with the immunomodulatory composition. For example, in some cases, an effective amount of an immunomodulatory composition of the present disclosure is an amount that is effective, when administered in a single dose or in multiple doses, to reduce the number and/or activity of innate and/or adaptive immune cells and/or their effector functions in an individual by at least 10%, at least 15%, at least 20%, at least 25%, at least 30%, at least 35%, at least 40%, at least 45%, at least 50%, at least 75%, or more than 75%, compared to the number and/or activity of innate and/or adaptive immune cells and/or their effector functions in the individual in the absence of treatment with the immunomodulatory composition.

In some cases, an effective amount of an immunomodulatory composition of the present disclosure is an amount that is effective, when administered in a single dose or in multiple doses, to induce and/or augment apoptosis in innate and/or adaptive immune cells in an individual to protect from undesirable inflammation. For example, in some cases, an effective amount of an immunomodulatory composition of the present disclosure is an amount that is effective, when administered in a single dose or in multiple doses, to induce and/or augment apoptosis in innate and/or adaptive immune cells in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the number of one or more of innate or adaptive immune cells in the individual in the absence of treatment with the immunomodulatory composition.

In some cases, an immunomodulatory composition of the present disclosure comprises CC and an antigen. Where an immunomodulatory composition of the present disclosure comprises CC and an antigen, in some cases, an effective amount of an immunomodulatory composition of the present disclosure is an amount that is effective, when administered in a single dose or in multiple doses, to modulate (e.g., reduce) an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. For example, where the antigen is an antigen associated with or derived from an autoantigen or an allergen, an effective amount of an immunomodulatory composition of the present disclosure is an amount that is effective, when administered in a single dose or in multiple doses, to modulate (e.g., reduce) an immune response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the immune response to the antigen in the absence of treatment with the immunomodulatory composition. For example, where the immunomodulatory composition comprises CC, an antigen, an autoantigen or an allergen, alone or in combination with each other, in some cases, an effective amount of an immunomodulatory composition of the present disclosure is an amount that is effective, when administered in a single dose or in multiple doses, to reduce the immune response to the antigen in an individual by at least 10%, at least 15%, at least 20%, at least 25%, at least 30%, at least 35%, at least 40%, at least 45%, at least 50%, at least 75%, or more than 75%, compared to the immune response to the antigen in the individual in the absence of treatment with the immunomodulatory composition.

The immune response can be a humoral immune response, e.g., a B cell or antibody immune response. Thus, e.g., in some cases, where the antigen is an antigen associated with or derived an autoantigen or an allergen, an effective amount of an immunomodulatory composition of the present disclosure is an amount that is effective, when administered in a single dose or in multiple doses, to modulate (e.g., reduce) a B cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the B cell response to the antigen in the absence of treatment with the immunomodulatory composition. For example, in some cases, an effective amount of an immunomodulatory composition of the present disclosure is an amount that is effective, when administered in a single dose or in multiple doses, to reduce the B cell response to the antigen in an individual by at least 10%, at least 15%, at least 20%, at least 25%, at least 30%, at least 35%, at least 40%, at least 45%, at least 50%, at least 75%, or more than 75%, compared to the B cell response to the antigen in the individual in the absence of treatment with the immunomodulatory composition. For example, in some cases, where the antigen is an antigen associated with or derived from an autoantigen or an allergen, an effective amount of an immunomodulatory composition of the present disclosure is an amount that is effective, when administered in a single dose or in multiple doses, to modulate (e.g., reduce) the amount of antibody specific to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the amount of antibody specific to the antigen in the absence of treatment with the immunomodulatory composition. For example, in some cases, an effective amount of an immunomodulatory composition of the present disclosure is an amount that is effective, when administered in a single dose or in multiple doses, to reduce the amount of antibody specific to the antigen in an individual by at least 10%, at least 15%, at least 20%, at least 25%, at least 30%, at least 35%, at least 40%, at least 45%, at least 50%, at least 75%, or more than 75%, compared to the amount of antibody specific to the antigen in the individual in the absence of treatment with the immunomodulatory composition.

The immune response can be a cellular immune response, e.g., a T cell immune response. Thus, e.g., in some cases, where the antigen is an antigen associated with or derived from an autoantigen or an allergen, an effective amount of an immunomodulatory composition of the present disclosure is an amount that is effective, when administered in a single dose or in multiple doses, to modulate (e.g., reduce) a T cell response to the antigen by at least about 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the T cell response to the antigen in the absence of treatment with the immunomodulatory composition. For example, in some cases, an effective amount of an immunomodulatory composition of the present disclosure is an amount that is effective, when administered in a single dose or in multiple doses, to reduce the T cell response to the antigen in an individual by at least 10%, at least 15%, at least 20%, at least 25%, at least 30%, at least 35%, at least 40%, at least 45%, at least 50%, at least 75%, or more than 75%, compared to the T cell response to the antigen in the individual in the absence of treatment with the immunomodulatory composition. In some cases, the immune response is a humoral immune response and a cellular immune response.

In some cases, an effective amount of an immunomodulatory composition of the present disclosure is an amount that is effective, when administered in a single dose or in multiple doses, to normalize the level of one or more serum markers of pathological immune responses. For example, in some cases, an effective amount of an immunomodulatory composition of the present disclosure is an amount that is effective, when administered in a single dose or in multiple doses, in normalizing the level of one or more of the serum markers (these markers include, but are not restricted to, cholesterol (CHOL), glucose (GLU), globulin (GLOB), alanine aminotransferases (ALT), aspartate aminotransferases (AST), total phosphates (TP), total bilirubin (TBIL), phosphate (PHOS), triglycerides (TRIG), uric acid (URIC), creatine kinase (CK) and urea) in an individual by at least 10%, at least 15%, at least 20%, at least 25%, at least 30%, at least 35%, at least 40%, at least 45%, at least 50%, at least 75%, or more than 75%, compared with the level of CHOL, GLU, GLOB, ALT, AST, TP, PHOS, TRIG, URIC, CK, TBIL or urea in the individual in the absence of treatment with the immunomodulatory composition.

Adjuvants

In some embodiments, a subject method involves administration of a subject immunomodulatory composition, where the immunomodulatory composition comprises CC and one or more adjuvants.

Exemplary adjuvants include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12, IL-15, IL-28, etc.) (WO99/44636), etc.), interferons (e.g. gamma interferon), macrophage colony stimulating factor (M-CSF), tumor necrosis factor (TNF), colony-stimulating factors (e.g., GM-CSF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; WO 96/02555, WO 98/16247, WO 98/18810, WO 98/40100, WO 98/55495, WO 98/37919 and WO 98/52581), i.e., oligonucleotides containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally including a sterol) e.g. WO 98/57659; (14) alphaGalCer and its derivatives; (16) toll-like receptor (TLR) agonists, NOD-like receptor (NLR) agonists, RIG-I agonists, agonists for C-type lectin receptors and other pathogen recognition receptor (PRR) agonists e.g., CpG ODNs, ISS-ODNs, rinatolimod, polyI:C and its derivatives, flagellin, ampligen, imidazoquinalines (e.g., imiquimod, resiquimod), muramyl dipeptides; (17) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human included in some cases.

Further exemplary adjuvants include, but are not limited to: cholera toxin B subunit, BCG, Pseudomonas aeruginosa exoprotein A, tocopherol, HBV core, E. coli heat labile toxins (such as LT-A, LT-B), Pertussis toxin, Diphtheria toxoid, tetanus toxoid, Cholera toxin derived (CTA1-DD, CT), mutant LT and CT, Aluminium salt-based adjuvants (such as Alum, Aluminum phosphate, Aluminum sulphate, Alhydrogel), Calcium phosphate, kaolin, monophosphoryl lipid A (MPLR) and its derivatives, glucoppyranosyl lipid A, synthetic lipid A, Lipid A mimetics, Vitamin E, Depovaxn™, Saponins (Quil-A, AS01, AS02 (squalene+MPL+QS-21)), AS03, AS04 (alum+MPL®), Tomatin, Protolin, RC-529, Pluronic™, Monatides, Matrix-M, OM-174, Lipovac, IC-31, bacterial/mycobacterial peptides (such as KLK, cationic (poly)peptides, anti-bacterial microbial peptides, defensins, tuftsin, cathelicidin), dipeptides (such as pidotimod), Bestatin, Hepon (tetradecapeptide), SCV-07 (gamma-D-glutamyl-L-tryptophan), Thymosin-a, Immunofan, Thymogen, Indolicidin and its derivatives, polyphosphagene and its derivatives, Gellan, nucleotides (mononucleotides, dinucleotides, polynucleotides, cyclic nucleotides), Eurocine etc.

Combination Therapy

In some embodiments, a subject method involves administration of a subject immunomodulatory composition as monotherapy, e.g., administration of a subject immunomodulatory composition only, without co-administration of any other therapeutic agent. In other embodiments, a subject treatment method is a combination therapy involving administration of: a) a subject immunomodulatory composition; and b) at least one additional therapeutic agent (or a pharmaceutically acceptable salt, prodrugs, salts of prodrugs, stereoisomers, tautomers etc. of the therapeutic agent), where the immunomodulatory composition and the at least one additional therapeutic agent are administered in combined amounts that are effective to modulate an immune response. Suitable additional therapeutic agents are described below.

A subject combination therapy can involve: a) administration of an immunomodulatory composition and at least one additional therapeutic agent at the same time, in the same formulation or in separate formulations; b) administration of at least one additional therapeutic agent within about 5 minutes to about 4 weeks of administration of an immunomodulatory composition, e.g., administration of at least one additional therapeutic agent within about 5 minutes to about 15 minutes, within about 15 minutes to about 30 minutes, within about 30 minutes to about 60 minutes, within about 1 hour to about 2 hours, within about 2 hours to about 4 hours, within about 4 hours to about 8 hours, within about 8 hours to about 12 hours, within about 12 hours to about 24 hours, within about 24 hours to about 2 days, within about 2 days to about 4 days, within about 4 days to about 7 days, within about 1 week to about 2 weeks, or within about 2 weeks to about 4 weeks of administration of an immunomodulatory composition.

In some embodiments, the at least one additional therapeutic agent is co-formulated with the immunomodulatory composition. In other embodiments, the at least one additional therapeutic agent and the immunomodulatory composition are separately formulated.

In some embodiments, an effective amount of an immunomodulatory composition and an at least one additional therapeutic agent are synergistic amounts. As used herein, a "synergistic combination" or a "synergistic amount" of a subject immunomodulatory composition and an additional (e.g., a second) therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the immunomodulatory composition when administered at that same dosage as a monotherapy and (ii) the therapeutic or prophylactic benefit of the additional therapeutic agent when administered at the same dosage as a monotherapy.

A subject combination therapy can involve: administration of an immunomodulatory composition and at least one additional form of therapy such as radiation therapy (comprising radioisotopes such as $^{12}$I, strontium-89, $^{32}$P, alpha-emitting isotopes, beta-emitting isotopes etc.), photodynamic therapy, laser therapy, natural product therapy, nutraceutical therapy, cellular therapy, prebiotic therapy, probiotic therapy, symbiotic therapy, paraprobiotic therapy etc., given at the same or different times.

A subject combination therapy can involve: administration of an immunomodulatory composition and at least one additional form of therapy such as one or more members of microbiota of an individual such as *Bacteroidetes, Proteobacteria, Firmicutes, Verrucomicrobia, Bacteroidales, Enterobacteriales, Clostridium*, VSL #3 etc. given at the same or different times. Thus, the present invention can be used to establish, modulate, regulate or maintain a balanced microbiota. Members of the microbiome can be wild-type, viable, inactivated, heat-killed, mutated, attenuated and/or genetically engineered.

A subject combination therapy can involve: administration of an immunomodulatory composition and at least one additional form of therapy such as one or more members of probiotics.

A subject combination therapy can involve: administration of an immunomodulatory composition and at least one additional form of therapy such as one or more members of therapeutic pathogenic bacteria, virus, fungus etc. such as *Listeria, Saccharomyces, Escherichia, Salmonella, Staphylococcus, Klebsiella*, poxviruses, adenoviruses, oncolytic viruses. Therapeutic pathogen can be wild-type, mutated, attenuated and/or genetically engineered. Members of the therapeutic pathogens can be wild-type, viable, inactivated, heat-killed, mutated, attenuated and/or genetically engineered.

In some embodiments, an effective amount of an immunomodulatory composition can be administered in a heterologous or homologous prime-boost vaccine, immunotherapy and/or chemotherapy regimen(s).

A subject combination therapy can involve: administration of an immunomodulatory composition and a therapeutic vaccine.

A subject combination therapy can involve: administration of an immunomodulatory composition and a therapeutic antibody. For example, in some embodiments, a subject method involves: a) administration of an immunomodulatory composition of the present disclosure; and b) administration of at least one antibody. The CC and the antibody can be in the same formulation or in separate formulations. The CC and the antibody can be administered simultaneously, or at different times. Suitable antibodies include an antibody against a cancer antigen or a pathogenic antigen (e.g., a therapeutic antibody, monoclonal antibodies, bispecific antibodies, chemoimmuno conjugated antibodies, radioimmunoconjugated antibodies, antibody-cytokine fusion proteins, antibody-antigen fusion proteins, antibody-immunotoxin fusion protein etc.). Suitable antibodies include, without limitation, antibodies directed against co-stimulatory or co-inhibitory molecules (CD28, CD40, ICOS, CD137, OX40, CD137, CD227, CTLA-4, PD-1, KIRs, TCR, PDL1, LAG3, TIM3, VISTA etc.); and other therapeutic antibodies. Non-limiting examples of suitable antibodies include, but are not limited to, adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumornab, pertuzumab, ranibizumab, rituximab, rovelizumab, tocilizumab, tositumomab, trastuzumab, ustekinumab, vedolizomab, zalutumumab, and zanolimumab.

Non-limiting examples of therapeutic and prophylactic antibodies that can be used in combination therapy with an immunomodulatory composition of the present disclosure include MDX-O00 (Medarex, NJ.) which is a humanized anti-CTLA-4 antibody for the treatment of prostate cancer, SYNAGIS™ (MedImmune, Md.) which is a humanized anti-respiratory syncytial virus (RSV) monoclonal antibody for the treatment of RSV infection; and HERCEPTIN™ (Trastuzumab) (Genentech, Calif.) which is a humanized anti-HER2 monoclonal antibody for the treatment of metastatic breast cancer. Other examples are humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti-Hepatitis B virus antibody (Protein Design Lab/Novartis); PROTOVIR™ which is a humanized anti-CMV IgGI antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti-CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/NorvartisfTanox Biosystems); ABX-CBL is a murine anti CD-147 IgM antibody (Abgenix); BTI-322 is a rat anti-CD2 IgG antibody (MedImmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab').sub.2 (Pasteur-Merieux/Immunotech); CAT-152 is a human anti-TGF-β$_2$ antibody (Cambridge Ab Tech); and Corsevin M is a chimeric anti-Factor VII antibody (Centocor). The above-listed immunoreactive reagents, as well as any other immunoreactive reagents, may be administered according to any regimen known to those of skill in the art, including the regimens recommended by the suppliers of the immunoreactive reagents.

Other examples of therapeutic and prophylactic antibodies that can be used in combination with an immunomodulatory composition of the present disclosure include Humira and Remicade; ACTEMRA™ (Genentech) which is a recombinant monoclonal IgG1 anti-human interleukin 6-receptor antibody for the treatment of anti-TNF resistant RA and juvenile idiopathic arthritis (JIA); ARZERRA™ (GlaxoSmithKline/Novartis) which is a chimeric human monoclonal antibody directed against membrane proximal epitope on the CD20 molecule for the treatment of RA; BENLYSTA™ (GlaxoSmithKline) which is a human monoclonal IgG1 gamma that binds to and inhibits the soluble form of the B-lymphocyte stimulator (BLyS) protein for the treatment of SLE; ORENCIA™ (Bristol-Myers Squibb) which is a CTLA-4 IgG1 binding to CD80/86 on antigen-presenting cells inhibiting the co-stimulation of CD28 on the T cells for the treatment of RA, JIA and SLE; SIMPONI (Janssen) which is a IgG1 monoclonal antibody acting on both soluble and membrane-bound TNF-α for the treatment of RA, psoriatic arthritis (PsA) and ankylosing spondylitis (AS); CIMZIA™ (UCB Group) which is a pegylated humanized antibody Fab' fragment of the TNF-α monoclonal antibody for the treatment of RA; Sifalimumab (MedImmune) which is an anti-IFN-α monoclonal antibody designed for the treatment of SLE, dematomyositis and polymyositis; various intravenous immunoglobulin products which are pools of immunoglobulins from healthy individuals for the treatment of SLE, systemic sclerosis and vasculitis; KINERE™ (Swedish Oprhan Biovitrum AB), ILARIS™ (Novartis) and ARCALYST™ (Regeneron) which are interleukin-1 blockers for the treatment of RA and cryopyrin-associated periodic syndrome (CAPS).

A subject combination therapy can involve: administration of an immunomodulatory composition of the present disclosure and one or more cytokines. For example, in some embodiments, a subject method involves: a) administration of an immunomodulatory composition of the present disclosure; and b) administration of one or more cytokines. The CC and the one or more cytokines can be in the same formulation or in separate formulations. The CC and the one or more cytokines can be administered simultaneously, or at different times. Suitable cytokines include, without limitation, interleukins, transforming growth factors (TGFs), fibroblast growth factors (FGFs), platelet derived growth factors (PDGFs), epidermal growth factors (EGFs), colony stimulating factors (CSFs), connective tissue activated peptides (CTAPs), osteogenic factors, and biologically active analogs, fragments, and derivatives of such growth factors. Suitable cytokines include BIT-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, 1L4, IL5, IL6, IL7, IL8, IL9, IL10, IL11, IL12, IL13, IL14, IL15, IL16, IL17, IL18, IL22, etc., leptin, myostatin, macrophage stimulating protein, platelet-derived growth factor, tumor necrosis factor (TNF)-alpha (TNF-α), TNF-β, nerve growth factor (NGF), CD40L, CD137L/4-1BBL, human lymphotoxin-β, G-CSF, M-CSF, GM-CSF, platelet-derived growth factor (PDGF), IL-1α, IL1-β, IP-10, PF4, GRO, 9E3, erythropoietin, endostatin, angiostatin, vascular endothelial growth factor (VEGF) or any fragments or combinations thereof. Other cytokines include members of the transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); hematopoietic growth factors (Flt3); pituitary growth hormones or derivatives; growth hormones, neuroactive hormones, Inhibins (for example, Inhibin A, Inhibin B); differentiation factors (for example, GDF-1); and Activins (for example, Activin A, Activin B, Activin AB).

A subject combination therapy can involve: administration of an immunomodulatory composition of the present disclosure and one or more therapeutic agents such as anti-angiogenic agents (e.g., in methods for the treatment of solid tumors and for the treatment and prevention of metastases) and anti-hormonal agents (particularly in methods for the treatment of hormone-dependent cancers such as breast cancer and prostate cancer).

In one embodiment, an immunomodulatory composition of the present disclosure is administered in combination with one or more anti-angiogenic agents. Such agents include, without limitation, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122:497-511), a 19 amino acid peptide corresponding to a fragment of Thrombospondin I (Tolsma et al., 1993, J. Cell Biol. 122: 497-511), a 20-amino acid peptide corresponding to a fragment of SPARC (Sage et al., 1995, J. Cell. Biochem. 57:1329-1334), or any fragments, family members, or variants thereof, including pharmaceutically acceptable salts thereof.

Other peptides that inhibit angiogenesis and correspond to fragments of laminin, fibronectin, procollagen, and EGF have also been described (see, e.g., Cao, 1998, Prog Mol Subcell Biol. 20:161-176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569-571; Hammes et al., 1996, Nature Medicine 2:529-533). Moreover, inhibition of the urokinase plasminogen activator receptor by receptor antagonists inhibits angiogenesis, tumor growth and metastasis (Min et al., 1996, Cancer Res. 56: 2428-33; Crowley et al., 1993, Proc Natl Acad Sci. 90:5021-25).

In another embodiment, a combination therapy of the present disclosure comprises administering an immunomodulatory composition of the present disclosure together with a hormonal treatment modality. Such treatment modalities include the administration of hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), and antiandrogens (e.g., cyproterone acetate).

In another embodiment, an immunomodulatory composition of the present disclosure is used in association with a treatment modality that utilizes polynucleotide compounds, such as antisense polynucleotides, ribozymes, RNA interference molecules, triple helix polynucleotides and the like.

In certain embodiments, an immunomodulatory composition of the present disclosure is administered in combination with an immunoregulatory agent. In some embodiments, the immunomodulatory composition is formulated with the immunoregulatory agent. An "immunoregulatory agent" is a substance that suppresses, masks, or enhances the immune system of the subject to whom it is administered. Exemplary agents are those that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or α antibodies; anti-tumor necrosis factor-a antibodies; anti-tumor necrosis factor-.beta. antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain; IDO inhibitors; streptokinase; TGF-β; streptodomase; FK506; RS-61443; deoxyspergualin; and rapamycin. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), glucagon, thyroid stimulating hormone (TSH), and luteinizing hormone (LH); hepatic growth factor, fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor, transforming growth factors (TGFs) such as TGF-α and TGF-β; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines. Other examples of immunoregulatory agents include mesalazine, mesalamine, sulfasalazine, sulfasalazine derivatives, anti-histamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies.

In certain embodiments, an immunomodulatory composition of the present disclosure is administered in combination therapy with one or more immunomodulatory agents, e.g., a cytokine. Suitable cytokines include, but are not limited to, interleukin-1 (IL-1), IL-2, IL-3, IL-12, IL-15, IL-18, G-CSF, GM-CSF, thrombopoietin, and γ interferon.

Methods of Modulating an Anti-Bacterial Immune Response

The present disclosure provides methods of modulating an immune response to a bacterium or a substance produced by a bacterium, the method comprising administering to an individual in need thereof an effective amount of an immunomodulatory composition of the present disclosure.

In some cases, a method of the present disclosure of modulating an immune response to a bacterium, or a substance produced by a bacterium, is effective to reduce the number of bacteria (e.g., pathogenic bacteria) in the individual by at least about 25%, at least about 50%, at least about 75%, or at least about 99%, compared to a pre-treatment number of pathogenic bacteria in the individual, or to an extent that the pathogenic bacterium cannot be detected in the individual (e.g., in a biological sample obtained from the individual).

In some cases, a method of the present disclosure of modulating an immune response to a bacterium, or a substance produced by a bacterium (such as endotoxins, toxins, LPS etc.), is effective to regulate an immune response to a pathogenic bacterium. Pathogenic bacteria include, e.g., Gram positive bacteria, Gram negative bacteria, mycobacteria, etc. Non-limiting examples of pathogenic bacteria include Mycobacteria, *Streptococcus, Staphylococcus, Pseudomonas, Salmonella, Neisseria,* and *Listeria*. In some cases, the bacteria is *Neisseria gonorrhea, M. tuberculosis,*

*M. leprae, Listeria monocytogenes, Streptococcus pneumoniae, S. pyogenes, S. agalactiae, S. viridans, S. faecalis, S. aureus. S. epidermis*, or *S. bovis*.

Other examples of pathogenic bacteria contemplated include, but are not limited to, Gram positive bacteria (e.g., *Listeria, Bacillus* such as *Bacillus anthracis*, Erysipelothrix species), Gram negative bacteria (e.g., *Bartonella, Brucella, Burkholderia, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, *Neisseria* species.

Additional non-limiting examples of specific infectious bacteria include *Citrobacter, Chlamydia* spp., *Helicobacter pyloris, Borelia burgdorferi, Legionella pneumophila, Mycobacteria avium, M. intracellulare, M. kansaii, M. gordonae, M. africanum, Staphylococcus aureus, Neisseria meningitidis, Haemophilus influenzae, Bacillus anthracis, Yersinia pestis, Corynebacterium diphtheriae, Erysipelothrix rhusiopathiae, Clostridium perfringens, Clostridium tetani, Enterobacter aerogenes, Klebsiella pneumoniae, Pasteurella multocida, Fusobacterium nucleatum, Streptobacillus moniliformis, Treponema pallidium, Treponema pertenue*, Leptospira, *Rickettsia, Porphyromonas gingivalis*, and *Actinomyces israelli*.

The pathogenic bacteria can be wild-type, viable, inactivated, heat-killed, mutated, attenuated and/or genetically modified.

In some cases, a method of the present disclosure of modulating an immune response to a bacterium, or a substance produced by a bacterium, comprises administering an immunomodulatory composition to an individual in need thereof, and further comprising administering to the individual an effective amount of an anti-bacterial or an anti-mycobacterial agent. Anti-bacterial and anti-mycobacterial agents are known in the art and include, e.g., beta-lactam antibiotics, tetracyclines, streptomycin, chloramphenicol, neomycin, gramicidin, bacitracin, sulfonamides, nitrofurazone, nalidixic acid, rifampicin, fluoroquinolones, isoniazid, pyrazinamide, vancomycin, methicillin etc.

Suitable anti-bacterial agents include, e.g., Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin; Ansamycins such as Rifamide, Rifampin, Rifamycin and Rifaximin; β-lactams such as Carbapenems such as Imipenem; Cephalosporins such as Cefactor, Cefadroxil, Cefamandole, Cefatrizine, Cefazedone, Cefazolin, Cefixime, Cefinenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin; Cephamycins such as Cefbuperazone, Cefmetazole, Cefminox, Cefetan and Cefoxitin; Monobactams such as Aztreonam, Carumonam and Tigemonam; Oxacephems such as Flomoxef and Moxolactam; Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin; Lincosamides such as Clindamycin and Lincomycin; Macrolides such as Azithromycin, Carbomycin, Clarithromycin, Erythromycin, Erythromycin Acistrate, Erythromycin Estolate, Erythromycin Glucobeptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin; Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin; Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; Cycloserine; Mupirocin; and Tuberin. Suitable anti-bacterial agents include antibodies specific for a bacterium.

Methods of Modulating an Anti-Viral Immune Response

The present disclosure provides methods of modulating an immune response to a virus, the method comprising administering to an individual in need thereof an effective amount of an immunomodulatory composition of the present disclosure.

In some cases, a method of the present disclosure of modulating an immune response to a virus is effective to reduce the number of viruses (e.g., pathogenic viruses) in the individual by at least about 25%, at least about 50%, at least about 75%, or at least about 99%, or to an extent that the pathogenic virus cannot be detected in the individual (e.g., in a biological sample obtained from the individual).

For example, in some cases, a method of the present disclosure of modulating an immune response to a virus is effective to reduce the viral load in the individual by at least about 25%, at least about 50%, at least about 75%, or at least about 99%, or to an extent that the pathogenic virus cannot be detected in the individual (e.g., in a biological sample obtained from the individual). In some cases, a method of the present disclosure of modulating an immune response to a virus is effective to reduce the number of genome copies of the virus in the individual by at least about 25%, at least about 50%, at least about 75%, or at least about 99%, compared to a pre-treatment number of genome copies of the virus in the individual, or to an extent that no genome copies of the virus can be detected in the individual (e.g., in a biological sample obtained from the individual).

In some cases, a method of the present disclosure of modulating an immune response to a virus regulates an immune response to a pathogenic virus. Pathogenic viruses include, but are not limited to, herpes viruses (HSV-1, HSV-2, VZV, EBV, CMV, HHV-6, HHV-8), influenza viruses (Flu A, B), hepatitis viruses (HepA, HepB, HepC, HepD, HepE), human immunodeficiency viruses (HIV-1, HIV-2), respiratory syncytial viruses, measles viruses, rhinoviruses, adenoviruses, SARS viruses, papillomaviruses, orthopoxviruses, West Nile viruses, and a dengue viruses. Pathogenic viruses include members of the Flaviviridae family of viruses. Pathogenic viruses include a flavivirus selected from the group consisting of dengue, Kunjin, Japanese encephalitits, West Nile, and yellow fever virus. Pathogenic viruses include lymphocytic choriomenignitis virus, hepatitis B virus, Epstein Barr virus, and human immunodeficiency virus. Pathogenic viruses include, but are not limited to: Retroviridae (e.g. human immunodeficiency viruses, such as HIV-1, also referred to as LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola-like viruses; Marburg virus); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (e.g., adenoviruses); Herpesviridae (herpes simplex virus (HSV) 1 and 2), varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis, thought to be a defective satellite of hepatitis B virus), the agents of non-A, non-B hepatitis (class 1, internally transmitted; class 2, parenterally transmitted, i.e., Hepatitis C Virus); Norwalk and related viruses, and astroviruses.

In some cases, a method of the present disclosure of modulating an immune response to a virus, comprises administering an immunomodulatory composition to an individual in need thereof, and further comprising administering to the individual an effective amount of at least one additional therapeutic agent, e.g., an anti-viral agent.

Anti-viral agents are known in the art and include, e.g., an anti-HCV agent such as ribavirin and its analogues; glycosidase inhibitors; glucosidase inhibitors; IRES (internal ribosomal entry site), p7, entry, fusion, helicase, assembly, egress, NS2, NS3, NS4, NS5a and NS5B inhibitors; inosine monophosphate dehydrogenase inhibitors; cyclophilin inhibitors; metalloprotease inhibitors; anti-HCV nucleos(t)ide and non-nucleoside RNA polymerase inhibitors etc.; an anti-HIV agent; anti-HBV agent; and the like.

In some embodiments, the at least one additional therapeutic agent is an interferon (e.g., interferon-alpha, interferon-beta, interferon-gamma, interferon-lambda, interferon-tau, interferon-omega, etc.). In some embodiments, the at least one additional therapeutic agent is IFN-α. In some embodiments, the at least one additional therapeutic agent is IFN-β.

Suitable additional anti-viral agents for treating an HCV infection include, but are not limited to, ribavirin and its prodrugs such as viramidine, telaprevir, sofosbuvir, boceprevir, ciluprevir, simeprevir, danoprevir, vaniprevir, MK-5172, MK-0608, 2'-C-methyl-7-deaza adenosine, 2'-C-methyl-adenosines, BI201335, narlaprevir, asunaprevir, GS-9256, GS-9451, ABT-450, IDX-320, ACH-1625, Valopicitabine, mericitabine, R1626, PSI-938, INX-189, BILN1941, BI-207127, VCH222, VX-135, ANA598, ANA773, ABT-072, ABT-333, HCV-796, GS-9190, Daclatasavir, BMS-824393, BMS-791325, PPI-461, GS-5885, alisporivir (Debio-025), NIM-811, SCY-635, nitazoxanide, clemizole, miravirasen, celgosivir, BCX-5191, GSK-2336805, anti-PD-1 antibodies (CT-011), bavituximab (anti-phosphatidyl serine Mab), therapeutic vaccine (GI-5005, IC-41, TG-4040) prophylactic vaccine (such as HCV E1/E2/MF-59), and the prodrugs thereof. Suitable additional therapeutic agents include, e.g., therapeutic agents for the treatment of an hepatitis B virus infection include, but are not limited to lamivudine, adefovir, entecavir, telbuvudine, tenofovir and the prodrugs thereof.

For example, suitable additional anti-viral agents for treating an HCV infection include weekly injections of pegylated IFN-α combined with twice-daily oral doses of ribavirin (1-β-D-ribofuranosyl-1H-1,2,4-triazole-3-carboxamide).

Suitable additional therapeutic agents include, e.g., therapeutic agents for the treatment of an immunodeficiency virus infection, or for the treatment of a disorder that may accompany an immunodeficiency virus infection (e.g., a bacterial infection, a fungal infection, and the like). Suitable additional therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), cyanovirin-N, microvirin, fuzeon, anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, viral entry inhibitors, fusion inhibitors, integrase inhibitors, adriamycin, fluorouracil, methotrexate, asparaginase and combinations thereof. Additional suitable therapeutic agents for HIV include integrase and fusion inhibitors such as Raltegravir, Elvitegravir, Enfuvirtide, Maraviroc etc.

In some embodiments, the at least one additional therapeutic agent is a neuraminidase inhibitor, e.g., where the influenza virus is influenza A or influenza B. Suitable neuraminidase inhibitors include, e.g., oseltamivir (ethyl (3R,4R,5S)-5-amino-4-acetamido-3-(pentan-3-yloxy)cyclohex-1-ene-1-carboxylate; Tamiflu™), zanamivir (2R,3R, 4S)-4-[(diaminomethylidene)amino]-3-acetamido-2-[(1R, 2R)-1,2,3-trihydroxypropyl]-3,4-dihydro-2H-pyran-6-carboxylic acid; Relenza™), and peramivir (1S,2S,3S,4R)-

3-[(1S)-1-acetamido-2-ethyl-butyl]-4-(diaminomethylideneamino)-2-hydroxy-cyclopentane-1-carboxylic acid). In some embodiments, the at least one additional therapeutic agent is an M2 blocker, e.g., blocks a viral ion channel (M2 protein). The antiviral drugs amantadine and rimantadine are M2 blockers, and can be used in subject method.

Suitable additional therapeutic agents, e.g., for the treatment of an HSV-1 or an HSV-2 infection include, but are not limited to, acyclovir (Zovirax), valganciclovir, famciclovir, valacyclovir (Valtrex), ganciclovir (Cytovene), cidofovir (Vistide), antisense oligonucleotide fomivirsen (Vitravene), foscarnet (Foscavir), penciclovir, idoxuridine, vidarabine, and trifluridine.

In some embodiments, the one or more different therapeutic agent is selected antiviral agents that target two or more different viruses; e.g., an HIV inhibitor, HBV inhibitor, HCV inhibitor, herpes virus inhibitor, influenza virus inhibitor, RNA inhibitor, interfering RNA (RNAi) inhibitor, natural products etc. In some cases, a method of the present disclosure of treating a viral infection comprises administering an immunomodulatory composition to an individual in need thereof, and further comprising administering to the individual an effective amount of at least one additional therapeutic agent, e.g., a monoclonal antibody or antibody products directed against viral antigens, where suitable monoclonal antibodies include but are not limited to HBIg, antibodies against influenza virus strains, anti-hepatitis A virus antibody, SYNAGIS (anti-RSV Mab), anti-rabies antibody, ostavir (anti-HBV Mab), Pro542 (anti-HIV gp120), Potovir (anti-CMV Mab), anti-PD-1 antibodies (CT-011), bavituximab (anti-phosphatidyl serine Mab) etc.

Methods of Modulating an Immune Response to a Parasitic Infection

The present disclosure provides methods of modulating an immune response to a microbial parasite (e.g., a pathogenic protozoan; a helminth; etc.), the method comprising administering to an individual in need thereof an effective amount of an immunomodulatory composition of the present disclosure.

In some cases, a method of the present disclosure of modulating an immune response to a microbial parasite is effective to reduce the number of microbial parasites (e.g., pathogenic protozoa; pathogenic helminths) in the individual by at least about 25%, at least about 50%, at least about 75%, or at least about 99%, compared to a pre-treatment number of microbial parasite in the individual, or to an extent that the microbial parasite cannot be detected in the individual (e.g., in a biological sample obtained from the individual).

In some cases, a method of the present disclosure of modulating an immune response to a microbial parasite comprises administering an immunomodulatory composition to an individual in need thereof, and further comprising administering to the individual an effective amount of a least one additional therapeutic agent. Anti-parasitic agents are known in the art and include, e.g., chloroquine, etc. For example, anti-malarial agents include, e.g., quinine, chloroquine, atovaquone, proguanil, primaquine, amodiaquine, mefloquine, piperaquine, artemisinin, methylene blue, pyrimethamine, sulfadoxine, artemether-lumefantrine, dapsone-chlorproguanil, artesunate, quinidine, clopidol, pyridine/pyridinol analogs, 4(1H)-quinolone analogs, dihydroartemisinin, a mixture of atovaquone and proguanil, an endoperoxide, and an acridone. Anti-parasitic agents include antibodies specific for the parasite.

In some cases, a method of the present disclosure of modulating (e.g., reducing) an immune response to a microbial parasite modulates an immune response to a microbial parasite such as *Plasmodium* spp., *Toxoplasma gondii*, *Babesia* spp., *Trichinella spiralis*, *Entamoeba histolytica*, *Giardia lamblia*, *Enterocytozoon bieneusi*, *Naegleria*, *Acanthamoeba*, *Trypanosoma rhodesiense* and *Trypanosoma gambiense*, *Isospora* spp., *Cryptosporidium* spp, *Eimeria* spp., *Neospora* spp., *Sarcocystis* spp., and *Schistosoma* spp.

In some cases, a method of the present disclosure of modulating (e.g., reducing) an immune response to a protozoan parasite modulates an immune response to a protozoan parasite such as Giardia; a *plasmodium* species (e.g., *Plasmodium falciparum*); *Toxoplasma gondii*; a *cryptosporidium*; a *Trichomonas* species; a trypanosome (e.g., *Trypanosoma cruzi*); or *Leishmania*.

Methods of Modulating an Immune Response to a Pathogenic Fungus

The present disclosure provides methods of modulating an immune response to a pathogenic fungus, the method comprising administering to an individual in need thereof an effective amount of an immunomodulatory composition of the present disclosure.

In some cases, a method of the present disclosure of modulating an immune response to a pathogenic fungus is effective to reduce the number of fungal bodies in the individual by at least about 25%, at least about 50%, at least about 75%, or at least about 99%, compared to a pre-treatment number of fungal bodies in the individual, or to an extent that the pathogenic fungus cannot be detected in the individual (e.g., in a biological sample obtained from the individual).

In some cases, a method of the present disclosure of modulating (e.g., reducing) an immune response to a pathogenic fungus induces or modulates an immune response to a fungus such as *Candida* spp. including *C. albicans*, *Aspergillus* spp., *Cryptococcus* spp. including *C. neoformans*, *Blastomyces* sp., *Pneumocytes* spp., or *Coccidioides* spp.

In some cases, a method of the present disclosure of modulating an immune response to a pathogenic fungus comprises administering an immunomodulatory composition to an individual in need thereof, and further comprising administering to the individual an effective amount of a least one additional therapeutic agent. Anti-fungal agents are known in the art and include, e.g., flucanazole, 5-fluorocytosine, etc.

Suitable anti-fungal agents include, e.g., Polyenes such as Amphotericin-B (including various formulations of Amphotericin-B), Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, Pyrrolnitrin, Siccanin, Tubercidin and Viridin; Allylamines such as Naftifine and Terbinafine; Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole; Triazoles such as Fluconazole, Itraconazole and Terconazole; and other others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.

Methods of Treading an Allergic Disease

The present disclosure provides methods of treating an allergic disease such as asthma, allergic rhinitis, conjunctivitis, atopic dermatitis in an individual, the method comprising administering to the individual an effective amount of an immunomodulatory composition of the present disclosure. In some cases, a method of the present disclosure of treating an allergic disease comprises administering to an individual in need thereof an effective amount of an immunomodulatory composition of the present disclosure, where the immunomodulatory composition comprises an allergen. Suitable allergens are described above.

In some cases, a subject a method of the present disclosure of treating an allergic disease is effective to regulate an immune response. In some cases, a subject a method of the present disclosure of treating an allergic disease is effective to decrease one or more of: a) the level of IgE in an individual; b) the level of allergen-specific IgE in an individual; c) the number of mast cells in the individual; d) the level of histamine in the individual; and e) the level of IL-4 in the individual, compared to a pre-treatment level.

In some cases, a method of the present disclosure of treating an allergic disease comprises administering an immunomodulatory composition to an individual in need thereof, and further comprising administering to the individual an effective amount of at least one additional therapeutic agent. Suitable additional therapeutic agents include, e.g., anti-histamines, steroids (e.g., corticosteroids), prostaglandin inducers, anti-inflammatory agents, leukotriene antagonists, IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and downregulators of IgE. Suitable steroids include, but are not limited to, beclomethasone, fluticasone, tramcinolone, budesonide, corticosteroids and budesonide.

Methods of Treating an Autoimmune Disorder

The present disclosure provides methods of treating an autoimmune disorder in an individual, the method comprising administering to the individual an effective amount of an immunomodulatory composition of the present disclosure. Autoimmune conditions account for many autoimmune disorders such as rheumatoid arthritis, asthma, type 1 diabetes, multiple sclerosis, systemic lupus erythrymatosus (SLE), Sjorgen's syndrome, atherosclerosis, autoimmune hepatitis, autoimmune pancreatitis, celiac disease, autoimmune hemolytic anemia, ankylosing spondylitis, autoimmune disease associated cancers, autoimmune disease associated fibrosis, etc. By modulating innate and adaptive immune mechanisms through the immunomodulatory composition of the present disclosure, autoimmune disorders can be treated. In some cases, a method of the present disclosure of treating an autoimmune disorder comprises administering to an individual in need thereof an effective amount of an immunomodulatory composition of the present disclosure, where the immunomodulatory composition comprises an autoantigen. Suitable autoantigens are described above.

In some cases, a subject a method of the present disclosure of treating an autoimmune disorder is effective to reduce the number and/or activity of self-reactive T cells in an individual by at least about 25%, at least about 50%, at least about 75%, or at least about 99% compared to a pre-treatment number and/or activity of self-reactive T cells, or to an extent that self-reactive T cells cannot be detected in the individual (e.g., in a biological sample obtained from the individual).

In some cases, a subject a method of the present disclosure of treating an autoimmune disorder is effective to reduce the level of autoantibodies in an individual by at least about 25%, at least about 50%, at least about 75%, or at least about 99% compared to a pre-treatment level of autoantibodies, or to an extent that autoantibodies cannot be detected in the individual (e.g., in a biological sample obtained from the individual).

In some cases, a subject a method of the present disclosure of treating an autoimmune disorder is effective to modulate the level of cytokines in an individual by at least about 25%, at least about 50%, at least about 75%, or at least about 99% compared to a pre-treatment level of cytokines, or to an extent that cytokines cannot be detected in the individual (e.g., in a biological sample obtained from the individual).

In some cases, a method of the present disclosure of treating an autoimmune disorder comprises administering an immunomodulatory composition to an individual in need thereof, and further comprising administering to the individual an effective amount of a least one additional therapeutic agent. Examples of therapeutic agents that can be used to treat autoimmune disorders include, but are not limited to, anti-inflammatory agents; immunosuppressive agents (e.g., corticosteroids (e.g., prednisone, cortisol, methylprednisolone, etc.)), cyclosporin A); cytotoxic agents (e.g., 6-mercaptopurine, azathioprine, methotrexate, alkylating agents anti-metabolite agents); plant alkaloids; natural products; steroid hormones; hypoxic agents; anti-proliferative agents; anticancer agents; danazol; colchisine; levamisole; biological response modifiers and the like.

Examples of therapeutic agents that can also be used to treat autoimmune disorders include agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, gemcitabine, cyclocytidine, guanazole, inosine glycodialdehyde, EICAR, ribavirin, tiazofurin, defroxamine and pyrazoloimidazole.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, camptothecin etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; antivascular flavonoids; and the like. Other agents include minerals, nutrients, vitamins, supplements, anti-oxidants, herbs, spices (ginger, oregano, clove etc), natural health products (green tea, fish oil etc) and anti-inflammatory treatments and modalities.

Other anti-proliferative cytotoxic agents are navelbene, CPT-11, anastrazole, letrazole, capecitabine, reloxafine, cyclophosphamide, folic acid, retinoic acid, ifosamide, and droloxafine. Other suitable anti-proliferative agents include siRNA, interfering RNA (RNAi), and anti-sense RNA.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore, compounds that bind to the estrogen receptor are used to block this activity. Corticosteroids may inhibit T cell proliferation.

Other cytotoxic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor, e.g., irinotecan, etopside phosphate, mitoxantrone; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; (10) antagonists of tumor necrosis factor; and (11) BRAF inhibitors.

Methods of Treating Diseases Comprising an Immune Dysregulation

The present disclosure provides methods of modulating, restoring and/or regulating an immune dysfunction in an individual, the method comprising administering to the individual an effective amount of an immunomodulatory composition of the present disclosure. Immune dysfunction conditions account for many diseases such as rheumatoid arthritis (RA) and related diseases, diabetes, psoriasis, systemic lupus erythematosus (SLE) and related diseases, graft-versus-host disease (GVHD), ulcerative colitis, bacterial-induced colitis, Crohn's disease, Alopecia areata, asthma, allergic rhinitis, conjunctivitis, transplant rejection, Hashimoto's thyroiditis, inflammatory bowel diseases (IBD), short bowel syndrome and other gastrointestinal disorders (such as Crohn's disease, ulcerative colitis), cardiovascular diseases, obesity, wound healing, burn recovery, aging, weight gain, fat deposition, etc. Dysregulation of immune responses at the gut mucosal surface can cause systemic immune activation through increased translocation of microbes and microbial products from the intestinal tract. By modulating innate and adaptive immune mechanisms (including immune cells, cytokines, antibodies etc.) through the immunomodulatory composition of the present disclosure, immune dysregulation can be prevented and/or treated.

In some cases, a method of the present disclosure of treating an immune dysfunction disorder comprises administering an immunomodulatory composition to an individual in need thereof, and further comprising administering to the individual an effective amount of at least one additional therapeutic agent.

In some cases, the method comprising administering to an individual in need thereof an effective amount of an immunomodulatory composition of the present disclosure in a vaccine including an antigen that will modulate the dysfunctional immune response to a disease related antigen.

In some cases, the method comprising administering to an individual in need thereof, an effective amount of an immunomodulatory composition of the present disclosure in protecting, modulating, restoring or correcting disease- or medical condition-related imbalances in the patients' microbiome. Dysbalance in microbiota accounts for various disorders such as dermatological conditions, exuberant inflammatory responses, inflammation associated cancers, preterm birth, infertility, female contraception, urogenital infections, sexually transmitted diseases etc.

Another aspect of the invention includes method of treatment by substantially increasing or decreasing a relative abundance of miocrobiota of the subject.

In some cases, a method of the present disclosure of treating an immune dysregulation and restoring homeostasis comprises administering an immunomodulatory composition to an individual in need thereof, and further comprising administering to the individual an effective amount of one or more members of the microbiome or a probiotic.

Methods of Treading Diseases Comprising an Undesirable Inflammatory Activity

The present disclosure provides methods of modulating and/or regulating an undesirable inflammatory activity in an individual, the method comprising administering to the individual an effective amount of an immunomodulatory composition of the present disclosure. Undesirable inflammatory conditions account for many diseases such as diarrhoeal disease, mucositis due to chemotherapy or radiotherapy, gastroenteritis due to an infectious agent or an antibiotic agent, pouchitis, obesity related inflammation, appendicitis, organ (liver, kidney, lung, heart, islets etc.)

transplantation, bacterial infections, viral infections, fungal infections, cancer-associated inflammation, urogenital diseases, bacterial vaginosis, surgical associated trauma, sepsis, anorexia, hyperoxalurea, ulcers, wound healing, renal disease, hepatic diseases, liver fibrosis, alcoholic hepatitis, fibrotic diseases such as lung fibrosis, kidney fibrosis, idiopathic pulmonary fibrosis, acne, undesirable respiratory inflammatory activity, inflammation-associated cancers, inflammation-associated organ (lung, liver, kidney, heart, gastrointestinal tract, brain etc.) damage and injury, autoinflammatory diseases (such as TNF receptor associated periodic syndrome, Dubin Johnson syndrome, Behcet's disease, familial mediteranean fever etc.) etc. By modulating innate and adaptive immune mechanisms (including immune cells, cytokines, chemokines, antibodies etc.) through the immunomodulatory composition of the present disclosure, inflammatory disorders can be prevented and/or treated.

In one aspect of the invention, controlling undesirable inflammatory responses also include modulation in the levels of hormones, prostaglandins, reactive intermediates and leukotrienes.

In some cases, a method of the present disclosure of treating an inflammatory disorder comprises administering an immunomodulatory composition to an individual in need thereof, and further comprising administering to the individual an effective amount of at least one additional therapeutic agent, one or more members of the microbiome or a probiotic. Examples of therapeutic agents that can be used to treat inflammatory conditions include, but are not limited to, anti-inflammatory agents; immunosuppressive agents; cytotoxic agents and the like.

Other nonlimiting examples of therapeutic agents that can be used to treat inflammatory conditions include; calcineurin inhibitors (e.g., pimecrolimus, tacrolimus, etc.), methotrexate, cyclosporine and topical agents (e.g., tazarotene, anthralin, calciprotriene, corticosteroids, etc.).

In some cases, the method comprising administering to an individual in need thereof an effective amount of an immunomodulatory composition of the present disclosure in a vaccine including an antigen that will modulate the inflammatory immune response to a disease related antigen.

Other examples of autoimmune diseases, immune dysregulation, inflammation, allergic diseases, dermal diseases, infectious diseases, and organ transplantations for which the composition is useful for treatment include diseases such as, primary sclerosis polingitis, sprue, autoimmune arthritis, Lyme arthritis, psoriatic arthritis, reactive arthritis, spondyloarthropathy, dermatitis scleroderma, sarcoidosis, disseminated intravascular coagulation, Kawasaki's disease, nephrotic syndrome, chronic fatigue syndrome, fibromyalgia, Wegener's granulomatosis, Henoch-Schoenlejn purpurea, microscopic vasulitis of the kidneys, chronic active hepatitis, uveitis, septic shock, toxic shock syndrome, sepsis syndrome, cachexia, acquired immunodeficiency syndrome, acute transverse myelitis, Huntington's chorea, primary biliary cirrhosis, hemolytic anemia, polyglandular deficiency type I syndrome and polyglandular deficiency type II syndrome, Schmidt's syndrome, adult (acute) respiratory distress syndrome, seronegative arthopathy, arthropathy, Reiter's disease, psoriatic arthropathy, chlamydia, yersinia and salmonella associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, autoimmune encephalomyelitis, chronic mucocutaneous candidiasis, giant cell arteritis, nonalcoholic fatty liver disease, steatohepatitis, primary sclerosing hepatitis, cryptogenic autoimmune hepatitis, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, Sjogren's disease associated lung disease, ankylosing spondy litis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, atrophic autoimmune hypothyroidism, primary myxoedema, phacogenic uveitis, primary vasculitis, vitiligo, anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, eosinophilic gastroenteritis, periodontal diseases such as chronic gingivitis and periodontitis, genitourinary disorders (such as glomerulonephritis, polycystic kidney disease, hydronephrosis, kidney failure, urinary tract obstruction, hyperuricemia etc.), gynaecological disorders (such as vulvodynia, vaginitis, pelvic disorders etc.), reproductive diseases, urological diseases, mitochondria related disorders, pain, migrane, haematological diseases, psychiatric disorders, mouth diseases (such as foot and mouth disease), musculoskeletol diseases, ocular diseases, renal disorders (such as nephropathic cystinosis), intoxication (such as alcohol intoxication, chronic salicylate intoxication), skin-pruritus, skin-keratosis, skin diseases (such as erythematosquamous, hypertrophic skin disease, popular skin disease, rosacea, pigment disorder, purpura, acne, skin allergy, vitiligo, bullous skin disease, epidermolysis, scleroderma, eczema, cutaneous lymphoma) muscle wasting disease, muscle disorders, bronchus diseases, vascular diseases, uterine fibroids, hormonal imbalance (such as chronic fatigue syndrome), hair loss, osteoporosis, upper respiratory tract infections-associated inflammation, and Paget's disease.

Methods of Treating Metabolic Disorders

The present disclosure provides methods of treating metabolic disorders in an individual, the method comprising administering to the individual an effective amount of an immunomodulatory composition of the present disclosure. Metabolic disorders account for many diseases such as obesity related metabolic dysfunction, diabetes mellitus, insulin resistance, glucose metabolism disorders, hypoinsulinemia, atherosclerosis, hypercholesterolemia, ischemia, metabolic syndrome, oxidative stress, hypertension, endocrine disorders (Addison's disease, Cushing's disease, hyperthyroidism, hypothyroidism, hypopituitarism, polycystic ovary syndrome etc.), abnormal lipid metabolism, obesity related disorders (such as bone loss, weight gain etc.), pancreas related disorders, mitochondrial disease etc. By modulating innate and adaptive immune mechanisms (including immune cells, cytokines, antibodies etc.) through the immunomodulatory composition of the present disclosure, metabolic diseases can be prevented and/or treated.

In some cases, a method of the present disclosure of treating an inflammatory disorder comprises administering an immunomodulatory composition to an individual in need thereof, and further comprising administering to the individual an effective amount of at least one additional therapeutic agent, one or more members of microbiome or a probiotic. For example, therapeutic agents of interest include and are not limited to those that are anti-inflammatory agents for the treatment of cardiovascular disease. Such agents include amlodipine, used to lower blood pressure and prevent chest pain; enalapril, used in the treatment of hypertension, and some types of chronic heart failure; pravastatin, atorvastatin and rosuvastatin, used for the treatment of dyslipidemia and the prevention of cardiovascular disease; angiotensin-converting enzyme (ACE) inhibitors (e.g., benazepril, ramipiril, etc.); angiotensin II receptor blockers (ARBs) (e.g., candesartan, losartan, etc.); beta blockers (e.g., acebutolol, bisoprolol, sotalol, etc.); calcium channel blockers (e.g., amlodipine, verapamil, etc.) etc. Other examples of therapeutic agents of interest include and are not limited to those that are anti-inflammatory agents for the treatment of diabetes. Such agents include agents that target the IKK-NF-κB pathway; etanercept, infliximab, adalimumab, which target TNF-α; anakinra and canakinumab which target IL-1β; tocilizumab which targets IL-6; AMP-activated protein kinase activators; sirtuin-1 activators; mammalian target of rapamycin inhibitors; C-C motif chemokine receptor 2 antagonists, etc. In some cases, therapeutic agents of interest include and are not limited to those that are anti-inflammatory agents for the treatment of obesity. Such agents include lorcaserin; Qsymia™ (Vivus); liraglutide, bupropion, naltrexone, lorcaserin, orlistat, phentermine/topiramate etc.

In some cases, therapeutic agents of interest include and are not limited to those that are used to treat metabolic disorders such as diabetes include Insulin (e.g., short-, rapid, intermediate and long-acting insulin), amylinomimetic drugs (e.g., pramlinitide), alpha-glucosidase inhibitors (e.g., acarbose, miglitol, etc.), biguanides (e.g., metformin, etc.), sulfonylureas (e.g., glyburide, glipizide, etc.), meglitinides (e.g., repaglinide), D-phenylalanine derivatives (e.g., nateglinide), thiazolidinediones (e.g., rosiglitazone, pioglitazone, etc.), DPP-4 inhibitors (e.g. itagliptin, saxagliptin, linagliptin, etc.), glucagon-like receptor-1 (GLP-1) agonists (e.g., exenatide, liraglutide, etc.), sodium glucose transporter-2 (SGLT-2) inhibitors (e.g., canagliflozin, dapagliflozin, etc.) etc.

Methods of Treating Neurological Disorders

The present disclosure provides methods of modulating and/or regulating an inflammatory response, the method comprising administering to an individual in need thereof an effective amount of an immunomodulatory composition of the present disclosure. Inflammatory conditions account for many neurological disorders such as Alzheimer's, depression, attention deficit hyperactive disorder (ADHD), mood disorders, schizophrenia, multiple sclerosis, Parkinson's disease, autism, Amyotrophic Lateral Sclerosis (ALS), Cerebral malaria disorders, Huntington's disease, anxiety disorders, epilepsy, etc. By modulating innate and adaptive immune mechanisms (including immune cells, cytokines, antibodies etc.) through the immunomodulatory composition of the present disclosure, neurological disorders can be treated.

In some cases, a method of the present disclosure of treating a neurological disorder comprises administering an immunomodulatory composition to an individual in need thereof, and further comprising administering to the individual an effective amount of at least one additional therapeutic agent, one or more members of the microbiome or a probiotic. Non-limiting examples of disease modifying agents for neurological disorders of interest include, acetylcholinesterase inhibitors (e.g., donepezil, rivastigmine, etc.), N-methyl, D-aspartate receptor (NMDAR) antagonists (e.g., memantine, neramexane, etc.), dopaminergic (e.g., carbi-dopa/Levodopa), dopamine agonists (e.g. pramipexole, ropinirole, apomorphine, etc.), anticholinergics (e.g., trihexyphenidyl, benztropine mesylate, etc.), catechol-o-methyltransferase (COMT) inhibitors (e.g. entacapone, tolcapone, etc.), anti-convulsants (e.g. diazepam, baclofen, dantrolene, tizanidine, etc.), disease modifying agents; (e.g., teriflunomide, fingolimod, mitoxantrone, dimethyl fumarate, natalizumab, etc.).

In some cases, the method comprising administering to an individual in need thereof an effective amount of an immunomodulatory composition of the present disclosure in a vaccine including an antigen that will modulate an immune response to a disease related protein such as the amyloid plaques characteristics of Alzheimer or Creutzfeldt-Jacob disease (CJD).

Methods of Preventing or Treating Immunosuppression and Infections

The present disclosure provides methods of preventing or limiting immune defect/deficiency/suppression due to viral infections or due to infections following strokes and other brain injuries comprising administering an immunomodulatory composition of the present disclosure to an individual in need thereof. Various forms of viral (e.g., HIV) infections, brain trauma, including stroke, lead to long-term systemic immune suppression, resulting in higher infection and mortality rates. Further, hepatic invariant NKT cells have been shown to be important to ameliorate systemic immunosuppression. The present disclosure represents a strategy to prevent systemic immunosuppression and infections in these patients through modulation of NK, NKT and other immune cells.

In some cases, a method of the present disclosure of treating an immune suppression, stroke or brain trauma disorder comprises administering an immunomodulatory composition to an individual in need thereof, and further comprising administering to the individual an effective amount of at least one additional therapeutic agent.

Methods of Enhancing the Efficacy and/or Reducing the Toxicity of a Therapeutic Treatment The present disclosure also provides methods for enhancing the efficacy and/or reducing the toxicity of a therapeutic treatment, and/or preventing the drug-resistance and altering metabolism, preferably treatment with an anti-infective (such as antibacterial, antifungal or antiviral), anticancer agents, therapeutic antibodies, anti-inflammatory agents, metabolic disorder related drugs, immunostimulatory agents, immunomodulatory compounds, immunoregulatory agents, Si RNAs, therapeutic microbes including probiotics and microbiome (viable, inactivated, heat-killed, mutated, attenuated, genetically engineered) or a surgical treatment by administering an effective amount of an immunomodulatory composition of the present disclosure to an individual, cells or tissues preferably the amount needed to regulate an immune response.

In some cases, a method of the present disclosure of enhancing efficacy and reducing toxicity comprises administering an immunomodulatory composition to an individual in need thereof, and further comprising administering to the individual an effective amount of at least one additional therapeutic agent.

Non-limiting examples of the suitable therapeutic agents and antibodies are described herein above in methods sections.

Methods of Modulating Dendritic Cells

The present disclosure provides a method of modulating dendritic cells, the method comprising: a) contacting dendritic cells (DCs) obtained from an individual with a composition comprising: i) *Caulobacter crescentus*; and/or ii) an antigen. The DCs are contacted with the CC and the antigen is in vitro. Contacting DCs with the antigen and the CC modulates antigen presentation of the antigen on the DCs, thereby generating a population of modulated DCs. In some cases, the antigen can be contacted with DCs using methods such as diffusion, electroporation, active transport, liposome fusion, phagocytosis, sonication etc. In some cases, the method further comprises administering the antigen-presenting DCs to the individual from whom the DCs were obtained. In some cases, the method further comprises administering the antigen-presenting DCs combined with antibodies, chemotherapeutic agents, or cytokines to the individual from whom the DCs were obtained. Administering modulated DCs to an individual can treat a disease in the individual.

Suitable antigens are described above. In some cases, a composition comprising CC and antigen is contacted with DCs; and the CC-antigen-DC mixture is incubated for a period of time of from about 30 minutes to about 48 hours, thereby generating a population of antigen-presenting DCs. A subject method can modulate the proportion of DCs that are antigen-presenting DCs by at least about 25%, at least about 50%, at least about 75%, at least about 2-fold, at least about 5-fold, at least about 10-fold, at least about 25-fold, at least about 50-fold, at least about 100-fold, or more than 100-fold, compared to the proportion of DCs in the starting population that are antigen-presenting DCs.

Methods of Generating Regulatory Immune Cells

The present disclosure provides a method of generating regulatory lymphocytes such as NK, NKT, γδ T cells, ILCs, T cells, and B cells, the method comprising: a) contacting lymphocytes (NK, NKT, γδ T cells, ILCs, T cells, and/or B cells) obtained from an individual with a composition comprising: i) *Caulobacter crescentus*; and/or ii) an antigen in the presence or absence of antigen presenting cells. Contacting lymphocytes and the CC generates a population of regulatory lymphocytes. In some cases, the method comprises administering the regulatory lymphocytes to the individual from whom the cells were obtained, to prevent and/or treat a disease in a host. In some cases, the method further comprises administering the regulatory lymphocytes combined with antibodies, chemotherapeutic agents, or cytokines to the individual from whom the cells were obtained, to prevent and/or treat a disease in a host.

Methods of Treating an Infection with an Intracellular Pathogen

The present disclosure provides methods of preventing and/or treating infections with intracellular pathogens (e.g., viruses, mycobacteria, bacteria, parasites etc.) in an individual, the method comprising administering to the individual an effective amount of an immunomodulatory composition of the present disclosure.

In some cases, a method of the present disclosure of treating an intracellular pathogen comprises administering to an individual in need thereof, and further comprising administering to the individual an effective amount of at least one additional therapeutic agent.

Methods of Modulating Immune Responses in Animal Models or Cell Culture for Research, Diagnosis and/or Therapeutic Purposes The present disclosure provides a method of modulating immune responses in animal models for research purposes. The present disclosure further provides a method of modulating various TLRs, NLRs, DCs and/or effector lymphocytes such as NK, NKT, T and B cells, the method comprising: a) contacting effector cells (NK, NKT, T and B cells) obtained from an individual with a composition comprising: i) *Caulobacter crescentus*; and/or ii) an antigen in the presence or absence of antigen presenting cells. Contacting effector lymphocytes and the CC modulates their activation, thereby generating a population of regulated effector lymphocytes. In some cases, the method comprises of diagnosing a disease state by identifying and expanding specific antigen reactive T cells and/or B cells. In some cases, the method comprises of identifying and expanding specific antigen reactive T cells and/or B cells in vitro for research purposes. In some cases the method comprises of administering the activated effector lymphocytes to the individual from whom the cells were obtained, to prevent and/or treat a disease in a host. In some cases, the method comprises of activating TLRs or NLRs for research and/or diagnostic purposes.

Methods of Inducing Proliferation, Differentiation and/or Modulation of Stem Cells The present disclosure provides a method of inducing proliferation, differentiation and/or modulation of stem cells and restoration of homeostasis in an individual, the method comprising administering to the individual an effective amount of an immunomodulatory composition of the present disclosure. The present disclosure provides a method of modifying stem cells, the method comprising contacting the stem cells with a composition comprising *Caulobacter crescentus*, wherein said contacting generates a population of expanded, differentiated and/or modulated stem cells.

The present disclosure also provides a method of inducing proliferation, differentiation and/or moduation of stem cells, the method comprising contacting stem cells obtained from an individual with an immunomodulatory composition of the present disclosure, e.g., an immunomodulatory composition comprising *Caulobacter crescentus*. Contacting the stem cells with the CC leads to their proliferation and differentiation, thereby generating a population of expanded, differentiated and/or modulated cells. The population of expanded, differentiated and/or modulated cells can then be administered to the individual from whom the stem cells were obtained.

In some embodiments, a method of the present disclosure of inducing proliferation, differentiation and/or modulation of stem cells comprises: a) obtaining stem cells from an individual; b) contacting the stem cells in vitro with CC, thereby generating a population of expanded, differentiated and/or modulated cells; and c) administering the population of expanded, differentiated and/or modulated cells to the individual.

In some embodiments, a method of the present disclosure of inducing proliferation, differentiation and/or modulation of stem cells in an individual comprises administering to the individual an effective amount of an immunomodulatory composition of the present disclosure. In some cases, an effective amount of an immunomodulatory composition of the present disclosure is an amount that is effective, when administered in a single dose or in multiple doses, to induce proliferation, differentiation and/or modulation of hematpoietic stem cells, and restore homeostasis. For example, in some cases, an effective amount of an immunomodulatory composition of the present disclosure is an amount that is effective, when administered in a single dose or in multiple doses, to induce proliferation, differentiation and/or modulation of hematpoietic stem cells, and restore homeostasis in an individual by at least 10%, at least 15%, at least 20%, at least 25%, at least 30%, at least 35%, at least 40%, at least 45%, at least 50%, at least 75%, at least 100% (or 2-fold), at least 2.5-fold, at least 5-fold, at least 10-fold, more than 10-fold, at least 15-fold, at least 20-fold, at least 25-fold, at least 50-fold, at least 100-fold, or more than 100-fold, compared to the individual in the absence of treatment with the immunomodulatory composition.

Method of Delivering Therapeutic Molecules

The present disclosure provides a method of delivering therapeutic molecules such as a protein, peptide, siRNA, carbohydrate, macromolecules etc. where *Caulobacter crescentus* can act as a carrier and/or delivery vehicle to deliver the therapeutic molecule. As a non genetic modification (GM), such as electrostatic and hydrophobic interactions, binding of molecules to the *Caulobacter crescentus* surface may enable the *Caulobacter crescentus* to act as a carrier and/or delivery vehicle. Further, due to bioadhesion/mucoadhesion, *Caulobacter crescentus* may facilitate uptake of the delivered by M cell transport at mucosal surfaces.

Formulations, Dosages, and Routes of Administration

An immunomodulatory composition of the present disclosure can include one or more pharmaceutically acceptable excipients; and can be formulated in any of a variety of ways, that may depend, e.g., on the route of administration. Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins. Suitable excipient vehicles include, for example, water, saline, dextrose, glycerol, ethanol, inert proteins, hydrophillic polymers, amino acids, fatty acids, surfactants, non-ionic surfactants, carbohydrates, dextrins, polyols, chelating agents, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins.

An immunomodulatory composition can be incorporated into a variety of formulations for therapeutic administration. More particularly, an immunomodulatory composition can be formulated into pharmaceutical compositions by combination with appropriate, pharmaceutically acceptable carriers, salts, preservatives, buffering agents, or diluents, and may be formulated into preparations in solid, semi-solid, liquid, lyophilized, freeze-dried or gaseous forms, such as tablets, capsules, powders, granules, ointments, solutions, suppositories, injections, skin patches, inhalants and aerosols. In other embodiments, the formulation comprises a colloidal delivery system that includes e.g., liposomes, nano-particles, nano-emulsions, nano capsules, microspheres and polymers.

In pharmaceutical dosage forms, an immunomodulatory composition may be administered alone or in appropriate association, as well as in combination, with other pharmaceutically active compounds. An immunomodulatory composition, an antigen, adjuvant and/or therapeutic drug can be administered concurrently, simultaneously, sequentially or at different times, at the same or different sites, and via different routes. The following methods and excipients are merely exemplary and are in no way limiting.

For oral preparations, an immunomodulatory composition can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An immunomodulatory composition can be formulated into liquid preparations for administration by dissolving, suspending or emulsifying the composition in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An immunomodulatory composition can be utilized in aerosol formulation to be administered via inhalation. The immunomodulatory compositions of the present disclosure can be formulated into pressurized acceptable propellants such as dichlorodifluoromethane, propane, nitrogen and the like.

Furthermore, an immunomodulatory composition can be made into suppositories by mixing with a variety of bases such as emulsifying bases or water-soluble bases. An immunomodulatory composition can be administered rectally via a suppository. The suppository can include vehicles such as cocoa butter, carbowaxes and polyethylene glycols, which melt at body temperature, yet are solidified at room temperature.

An immunomodulatory composition of the present disclosure can also be administered in the form of liposomes or liposomal polymeric gels. Liposomes can be given by a variety of routes, oral, nasal, parenteral, trans-dermal, inhalation etc. As is known in the art, liposomes are derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to an immunomodulatory composition of the present disclosure, one or more of a stabilizer, a preservative, an excipients, and the like. Exemplary lipids are the phospholipids and the phosphatidylcholines (lecithins), both natural and synthetic.

Liposomes can be in a size range of from less than 100 nm to several microns. Methods to form liposomes are known in the art. for example, Prescott, Ed., *Methods in Cell Biology*, Volume XIV, Academic Press, New York, N.Y. (1976), p. 33 et seq.

Unit dosage forms for oral or rectal administration such as syrups, elixirs, emulsions, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise an immunomodulatory composition as a solution in sterile water, normal saline or another pharmaceutically acceptable carrier.

A subject immunomodulatory composition can be formulated for topical administration. Topical administration includes administration to the skin or mucosa, including surfaces of the lung eye, nose, and ear. Suitable topical preparations include, e.g., skin patch preparation, transdermal patch preparation, micro arrays, cream, lotion, gel preparations, powder, ointment, paste, intranasal drops or gels.

Ointments are semi-solid preparations, which are typically based on petrolatum or other petroleum derivatives. Suitable ointments include oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (WIO) emulsions or oil-in-water (OIW) emulsions, and include, for example, cetyl alcohol, glyceryl monostearate, lanolin and stearic acid. Exemplary water-soluble ointment bases are prepared from polyethylene glycols of varying molecular weight.

Lotions are preparations to be applied to the skin surface without friction, and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions can be used for treating large body areas, because of the ease of applying a more fluid composition. Lotions may contain suspending agents to produce better dispersions as well as compounds useful for localizing and holding the active agent in contact with the skin, e.g., methyl cellulose, sodium carboxymethyl-cellulose, or the like. An example of a lotion formulation for use in conjunction with the present invention contains propylene glycol mixed with a hydrophilic petrolatum such as that which may be obtained under the trademark Aquaphor® from Beiersdorf, Inc. (Norwalk, Coon.).

Suitable creams can be viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil so phase in volume, and generally contains a humectant. The emulsifier in a cream formulation, as explained in Remington, supra, is generally a nonionic, anionic, cationic or amphoteric surfactant.

Gels formulations can be used. Gels are semisolid, suspension-/type systems. Single-phase gels contain organic macromolecules distributed substantially uniformly throughout the carrier liquid, which can be aqueous, but may also contain an alcohol and, optionally, an oil.

A topical formulation may also be delivered to the skin using conventional "transdermal"-type patches, wherein the agent (immunomodulatory composition) is contained within a laminated structure that serves as a delivery device to be affixed to the skin. In such a structure, the immunomodulatory composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysioxanes, polyisobutylenes, polyacrylates, polyurethanes, and the like. The particular polymeric adhesive selected will depend on the particular immunomodulatory composition, vehicle, etc., i.e., the adhesive must be compatible with all components of the drug-containing composition. In an alternative embodiment, the immunomodulatory composition-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The term "unit dosage form," as used herein, refers to physically discrete units suitable as unitary dosages for human and animal subjects, each unit containing a predetermined quantity of an active agent (e.g., CC; antigen; etc.) calculated in an amount sufficient to produce the desired effect in association with a pharmaceutically acceptable diluent, carrier or vehicle. The specifications for the active agents depend on the particular compound employed and the effect to be achieved, and the pharmacodynamics associated with each compound in the host.

Other modes of administration will also find use. For instance, an immunomodulatory composition can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), or about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject proteins by the nasal mucosa.

An immunomodulatory composition can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, M, Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of an active agent (e.g., CC; antigen; etc.) adequate to achieve the desired state in the subject being treated.

The pharmaceutically acceptable excipients, such as vehicles, adjuvants, salts, carriers or diluents, are readily available to the public. Moreover, pharmaceutically acceptable auxiliary substances, such as pH adjusting and buffering agents, tonicity adjusting agents, stabilizers, emulsifying agents, surfactants, preservatives, amino acids, fatty acids, wetting agents and the like, are readily available to the public.

Oral Formulations

In some embodiments, an immunomodulatory composition is formulated for oral delivery to an individual in need of such an immunomodulatory composition.

For oral delivery, a subject formulation comprising an immunomodulatory composition will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

Suitable oral formulations also include an immunomodulatory composition, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an immunomodulatory composition formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrixrm (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoyl-carnitine, and sodium salts of fatty acids); toxins (e.g., zonula occludens toxin); and the like.

Suitable oral formulations also include an immunomodulatory composition, formulated as a food supplement (e.g. nutraceuticals, yogurt, frozen yogurt, milk powder, cheese, bars, drinks, prebiotics, symbiotics, paraprobiotics) etc.

Controlled Release Formulations

In some embodiments, an immunomodulatory composition is formulated in a controlled release formulation.

Controlled release can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems.* 1992 (Marcel Dekker, Inc.). Some of these formulations will now be discussed in more detail.

Enteric coatings are applied to tablets to prevent the release of active agents in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type.

Suitable enteric coating agents include, but are not limited to, hydroxypropylmethylcellulose phthalate, methacrylic acid-methacrylic acid ester copolymer, polyvinyl acetate-phthalate and cellulose acetate phthalate.

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method.

Examples of carriers useful in solid dispersions include, but are not limited to, water-soluble polymers such as polyethylene glycol, polyvinylpyraolidone, and hydroxypropylmethylcellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. An immunomodulatory composition can be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the drug of interest (e.g., an active agent) with ethyl cellulose and stearic acid in different ratios.

There are various methods commonly known for preparing solid dispersions. These include, but are not limited to, the melting method, the solvent method and the melting-solvent method.

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

An immunomodulatory composition of the present disclosure can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of an active agent and the release rates in a controlled release formulation, in order to optimize delivery of an active agent and its bioavailability.

Inhalational Formulations

An immunomodulatory composition of the present disclosure will in some embodiments be administered to a patient by means of a pharmaceutical delivery system for the inhalation route. The immunomodulatory composition may be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. A system that depends on the power of a compressed gas to expel the immunomodulatory composition from a container can also be used. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed, the aerosol contains the therapeutically active compound (e.g., active agent), which can be dissolved, suspended, or emulsified in a mixture of a fluid carrier and a propellant. The aerosol can be in the form of a solution, suspension, emulsion, powder, or semi-solid preparation. Aerosols can be used for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An immunomodulatory composition can also be formulated for delivery with a nebulizer, which is an instrument that generates very fine liquid particles of substantially uniform size in a gas. For example, a liquid containing the immunomodulatory composition is dispersed as droplets. The small droplets can be carried by a current of air through an outlet tube of the nebulizer. The resulting mist penetrates into the respiratory tract of the patient.

There are several different types of inhalation methodologies which can be employed in connection with an immunomodulatory composition of the present disclosure. An immunomodulatory composition can be formulated with low boiling point propellants. Such formulations are generally administered by conventional meter dose inhalers (MDIs). Alternatively, immunomodulatory composition can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166. An immunomodulatory composition can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

An immunomodulatory composition of the present disclosure will in some embodiments be formulated for vaginal delivery. A subject immunomodulatory composition for intravaginal administration can be formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject immunomodulatory composition will in some embodiments be formulated for rectal delivery. A subject formulation for intrarectal administration comprises a subject immunomodulatory composition formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel. An immunomodulatory composition of the present disclosure can be formulated with agents that improve adhesion to mucosal membranes such as mucoadhesives, bioadhesives, particles, microspheres or liposomes.

A subject immunomodulatory composition can include one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an immunomodulatory composition may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Dosages

The dosage of an immunomodulatory composition of the present disclosure can vary, depending on factors such as the clinical goals to be achieved, the age of the individual being treated, the physical status of the individual being treated, etc.

An immunomodulatory composition of the present disclosure can comprise CC in an amount of from about $10^3$ CC per unit dosage form to about $10^{20}$ CC per unit dosage form. For example, an immunomodulatory composition of the present disclosure can comprise CC in an amount of from about $10^3$ CC per unit dosage form to about $10^4$ CC per unit dosage form, from about $10^4$ CC per unit dosage form to about $10^5$ CC per unit dosage form, from about $10^5$ CC per unit dosage form to about $10^6$ CC per unit dosage form, from about $10^6$ CC per unit dosage form to about $10^7$ CC per ml, from about $10^8$ CC per unit dosage form to about $10^9$ CC per unit dosage form, from about $10^9$ CC per ml to about $10^{10}$ CC per unit dosage form, from about $10^{15}$ CC per unit dosage form to about $10^{20}$ CC per unit dosage form, or more than $10^{20}$ CC per unit dosage form.

For example, an immunomodulatory composition of the present disclosure can comprise CC in an amount of from about $10^3$ CC per ml to about $10^{20}$ CC per ml. For example, an immunomodulatory composition of the present disclosure can comprise CC in an amount of from about $10^3$ CC per ml to about $10^4$ CC per ml, from about $10^4$ CC per ml to about $10^5$ CC per ml, from about $10^5$ CC per ml to about $10^6$ CC per ml, from about $10^6$ CC per ml to about $10^7$ CC per ml, from about $10^8$ CC per ml to about $10^9$ CC per ml, from about $10^9$ CC per ml to about $10^{10}$ CC per ml, from about $10^{15}$ CC per ml to about $10^{20}$ CC per ml, or more than $10^{20}$ CC per ml.

An immunomodulatory composition of the present disclosure can comprise CC in an amount of from about $10^2$ to about $10^{20}$ colony forming units (cfu) per unit dosage form; for example, an immunomodulatory composition of the present disclosure can comprise CC in an amount of from about $10^2$ to about $10^3$ from about $10^3$ to about $10^5$, from about $10^5$ to about $10^7$, from about $10^7$ to about $10^9$, from about $10^9$ to about $10^{11}$, from about $10^{11}$ to about $10^{13}$, from about $10^{13}$ to about $10^{15}$, from about $10^{15}$ to about $10^{18}$, or from about $10^{18}$ to about $10^{20}$, cfu per unit dosage form. A unit dosage form can be an amount that is administered in a single dose; for example, a unit dosage form can be 0.5 ml, 1.0 ml, or other volume suitable for administration in a single dose.

An immunomodulatory composition of the present disclosure can comprise CC in an amount of from about $10^3$ CC per mg to about $10^{12}$ CC per mg. For example, an immunomodulatory composition of the present disclosure can comprise CC in an amount of from about $10^3$ CC per mg to about $10^4$ CC per mg, from about $10^4$ CC per mg to about $10^5$ CC per mg, from about $10^5$ CC per mg to about $10^6$ CC per mg, from about $10^6$ CC per mg to about $10^7$ CC per mg, from about $10^8$ CC per mg to about $10^9$ CC per mg, from about $10^9$ CC per mg to about $10^{10}$ CC per mg, from about $10^{10}$ CC per mg to about $10^{11}$ CC per mg, or from about $10^{11}$ CC per mg to about $10^{12}$ CC per mg.

An immunomodulatory composition of the present disclosure can comprise CC in an amount of from about $10^3$ CC per gram to about $10^{15}$ CC per gram. For example, an immunomodulatory composition of the present disclosure can comprise CC in an amount of from about $10^3$ CC per gram to about $10^4$ CC per gram, from about $10^4$ CC per gram to about $10^5$ CC per gram, from about $10^5$ CC per gram to about $10^6$ CC per gram, from about $10^6$ CC per gram to about $10^7$ CC per gram, from about $10^8$ CC per gram to about $10^9$ CC per gram, from about $10^9$ CC per gram to about $10^{10}$ CC per gram, from about $10^{10}$ CC per gram to about $10^{11}$ CC per gram, from about $10^{11}$ CC per gram to about $10^{12}$ CC per gram, from about $10^{12}$ CC per gram to about $10^{13}$ CC per gram, from about $10^{13}$ CC per gram to about $10^{14}$ CC per gram, or from about $10^{14}$ CC per gram to about $10^{15}$ CC per gram.

An immunomodulatory composition of the present disclosure can comprise CC in an amount of from about $10^2$ to about $10^{20}$ cfu per ml; for example, an immunomodulatory composition of the present disclosure can comprise CC in an amount of from about $10^2$ to about $10^3$, from about $10^3$ to about $10^5$, from about $10^5$ to about $10^7$, from about $10^7$ to about $10^9$, from about $10^9$ to about $10^{11}$, from about $10^{11}$ to about $10^{13}$, from about $10^{13}$ to about $10^{15}$, from about $10^{15}$ to about $10^{11}$, or from about $10^{18}$ to about $10^{20}$, cfu per ml.

In some embodiments, multiple doses of an immunomodulatory composition of the present disclosure are administered. The frequency of administration of an immunomodulatory composition of the present disclosure can vary depending on any of a variety of factors, e.g., severity of the symptoms, etc. For example, in some embodiments, an immunomodulatory composition of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an immunomodulatory composition of the present disclosure, e.g., the period of time over which an immunomodulatory composition of the present disclosure is administered, can vary, depending on any of a variety of factors, e.g., patient response, etc. For example, an immunomodulatory composition of the present disclosure can be administered over a period of time ranging from about one hour to one day, from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Where an immunomodulatory composition comprises an antigen, the dosage of antigen is selected as an amount which is effective and modulates an immune response without significant adverse side effects. Such amount can vary, depending, e.g., upon which specific antigen is employed, the route of administration, etc. Where an immunomodulatory composition comprises an antigen, the dosage of antigen can range from 1 ng per unit dosage form to about 100 mg per unit dosage form, e.g., from about 1 ng to about 25 ng, from about 25 ng to about 50 ng, from about 50 ng to about 100 ng, from about 100 ng to about 250 ng, from about 250 ng to about 500 ng, from about 500 ng to about 750 ng, from about 750 ng to about 1 µg, from about 1 µg to about 25 µg, from about 25 µg to about 50 µg, from about 50 µg to about 100 µg, from about 100 µg to about 250 µg, from about 250 µg to about 500 µg, from about 500 µg to about 750 µg, from about 750 µg to about 1 mg, from about 1 mg to about 25 mg, from about 25 mg to about 50 mg, or from about 50 mg to about 100 mg, per unit dosage form.

Routes of Administration

An immunomodulatory composition of the present disclosure is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, intranodal, percutaneous, transdermal, intratumoral, topical application, intravenous, intravesicular, rectal, nasal, oral and other enteral and parenteral routes of administration. Routes of administration may be combined, if desired, or adjusted depending upon the agent and/or the desired effect. The composition can be administered in a single dose or in multiple doses.

An immunomodulatory composition of the present disclosure can be administered to a host using any available conventional methods and routes suitable for delivery of conventional drugs, including systemic or localized routes. In general, routes of administration contemplated include, but are not necessarily limited to, enteral, parenteral, or inhalational routes.

Parenteral routes of administration other than inhalation administration include, but are not necessarily limited to, topical, transdermal, subcutaneous, intramuscular, intradermal, intralymphatic, intraorbital, intracapsular, intraspinal, intrasternal, intracranial, intravesicular, and intravenous routes, i.e., any route of administration other than through the alimentary canal. Parenteral administration can be carried to effect systemic or local delivery of the immunomodulatory composition. Where systemic delivery is desired, administration typically involves invasive or systemically absorbed topical or mucosal administration of pharmaceutical preparations.

An immunomodulatory composition of the present disclosure can also be delivered to the subject by enteral administration. Enteral routes of administration include, but are not necessarily limited to, oral and rectal (e.g., using a suppository) delivery.

An immunomodulatory composition of the present disclosure can also be delivered to the subject via a mucosal route of delivery. Mucosal routes of delivery include nasal, buccal, sublingual, vaginal, ocular, and rectal routes of administration.

In certain embodiments, an immunomodulatory composition of the present disclosure is administered to a subject via a combination of different routes in the order indicated below:

i. systemic, mucosal;
ii. systemic, systemic, mucosal, mucosal;
iii. systemic, mucosal, systemic;
iv. mucosal, mucosal, systemic, systemic;
v. mucosal, systemic, systemic;
vi. mucosal, systemic, mucosal, for example.

When an immunomodulatory composition of the present disclosure is administered systemically or mucosally more than once, the two or more systemic or mucosal administrations may be by the same systemic (for example, two intramuscular injections) or mucosal route (two IN/SL administrations) or different (for example, one intramuscular injection and one intravenous injection; one IN administration and one SL administration).

An immunomodulatory composition of the present disclosure is administered to an individual using any available method, delivery or device such as vaccine patches, needles, microneedles (hollow or solid), drop, syrup, tablets, capsules, pipette, dose-spray pumps, nasal dropper, inhalation devices, liquid or dry powder, suspensions or solutions, spray devices, Accuspray™, thermoresponsive gels, jet injectors, Nasovak™, Bespak™, ointment, lotions, suppositories, gels etc.

Suitable routes of administration are known in the art; any known route of administration can be employed in connection with administering an immunomodulatory composition of the present disclosure. See, e.g., Nursing Drug Guide: Nursing Drug Handbook (2015) $36^{th}$ ed, Lippincott.

Individuals Suitable for Treatment

Individuals suitable for treatment using a method of the present disclosure include humans; non-human mammals; fish; and birds. In any of the above embodiments discussed below, the individual being treated using a subject method can be a non-human mammal such as livestock (e.g., pigs, sheep, goats, cattles, equine, caprine, ovine, bovine, etc.); a mammalian pet (e.g., cats; dogs; horses; etc.); a bird such as chicken, hens, turkeys, geese, quail, ducks etc.; or other animals such as fish.

In any of the above embodiments discussed below, the individual being treated using a subject method is a human of from about one month to about 6 months, from about 6 months to about 1 year, or from about 1 year to about 5 years of age. In any of the above embodiments discussed below, the individual being treated using a subject method is a human of from about 5 years to about 12 years, from about 13 years to about 18 years, or from about 18 years to about 25 years of age. In any of the above embodiments discussed below, the individual being treated using a subject method is a human of from about 25 years to about 50 years, from about 50 years to about 75 years of age, or older than 75 years of age. In any of the above embodiments discussed below, the individual being treated using a subject method is a human who is immunocompromised.

In some embodiments, the individual has a viral disease, or is at risk of contracting a viral disease. In some cases, the disease is a viral disease selected from the group consisting of, but not limited to, viral disease caused by Zika virus, hepatitis B, hepatitis C, rotavirus, human immunodeficiency virus, human T-cell lymphotropic virus, DNA viruses such as parvoviruses, adeno viruses, papovaviruses (e.g., papilloma virus, polyoma viruses, and SV40), herpes viruses (e.g., herpes simplex type I (HSV-I), herpes simplex type II (HSV-II), and Epstein-Barr virus), poxviruses (e.g., variola (smallpox) and vaccinia virus); and RNA viruses, such as retroviruses [e.g. human immunodeficiency virus type I (HIV-I), human immunodeficiency virus type II (HIV-II), human T-cell lymphotropic virus type I (HTLV-I), human T-cell lymphotropic virus type II (HTLV-II)], orthomyxoviruses (e.g., influenza viruses), paramyxoviruses (e.g., measles virus, mumps virus, respiratory syncytial virus), rhabdoviruses (e.g., rabies virus), Sendai virus, picornaviruses (e.g., poliomyelitis virus, coxsackieviruses, rhinoviruses), reoviruses (e.g., rotavirus, colorado tick fever virus), togaviruses (e.g., rubella virus (German measles), Japanese encephalitis virus and Semliki forest virus), arboviruses, calciviruses (e.g., hepatitis E virus), flaviviruses (e.g., yellow fever virus, dengue virus), coronaviruses, filoviruses (e.g., Ebola and Marburg viruses) and Bunyaviruses (e.g., Hanta virus, California encephalitis virus).

In some embodiments, the individual has a bacterial infection, or is a risk of contracting a bacterial infection. In some embodiments, the individual has a mycobacterial infection, or is at risk of contracting a mycobacterial infection. In some embodiments, the individual is infected with, or is at risk of becoming infected with, a pathogenic bacterium. Pathogenic bacteria include, e.g., Gram positive bacteria, Gram negative bacteria, mycobacteria, etc. Non-limiting examples of pathogenic bacteria include Mycobacteria (e.g., *M. tuberculosis, M. avium* complex), nontuberculosis Mycobacteria, *Streptococcus, Staphylococcus, Pseudomonas, Salmonella, Neisseria,* and *Listeria*. In some cases, the bacteria is *Neisseria gonorrhea, M. tuberculosis, M. leprae, Listeria monocytogenes, Streptococcus pneumoniae, S. pyogenes, S. agalactiae, S. viridans, S. faecalis,* or *S. bovis*. Other examples of pathogenic bacteria contemplated include, but are not limited to, Gram positive bacteria (e.g., *Listeria, Bacillus* such as *Bacillus anthracis*, Erysipelothrix species), Gram negative bacteria (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio,* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, *Neisseria* species.

In some cases, the individual has, or is at risk of contracting, a parasitic disease. Parasitic diseases that can be treated or prevented by the methods of the present disclosure include, but are not limited to, amebiasis, malaria, leishmania, coccidia, giardiasis, cryptosporidiosis, toxoplasmosis, trypanosomiasis, schistosomiasis, and filariasis.

In some cases, the individual has, or is at risk of contracting, a fungal disease. Fungal diseases that can be treated or prevented by the methods of the present disclosure include, but are not limited to *Candida* spp. including *C. albicans, Aspergillus* spp., *Cryptococcus* spp. including *C. neoformans, Blastomyces* sp., *Pneumocytes* spp., yeast, mold, or *Coccidioides* spp.

In some cases, the individual has, or is at risk of contracting, a worm infection, a fluke infection, etc. Also encompassed are infections by various worms, such as but not limited to ascariasis, ancylostomiasis, trichuriasis, strongyloidiasis, toxoccariasis, trichinosis, onchocerciasis filaria, and dirofilariasis. Also encompassed are infections by various flukes, such as but not limited to schistosomiasis, paragonimiasis, and clonorchiasis.

In some embodiments, the individual has an autoimmune disorder, inflammatory disorder or an immune dysfunction, or is at risk of developing an autoimmune disorder, inflammatory disorder or an immune dysfunction. In some cases, the disease is selected from the group consisting of, but not limited to, allergy, rheumatoid arthritis, asthma, diabetes, systemic lupus erythematosus (SLE), Grave's disease, atherosclerosis, multiple sclerosis, schizophrenia, Alzheimer's, depression, hypopituitarism, neurodegenerative disorders, cardiovascular diseases, obesity, organ transplantation, sepsis, hepatic diseases, psoriasis, metabolic diseases, etc.

In some cases, the disease is selected from the group consisting of autoimmune and autoimmune-related diseases, including, but not limited to, acute disseminated encephalomyelitis, acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome, angioedema, aplastic anemia, dysautonomia, hepatitis, hyperlipidemia, immunodeficiency, inner ear disease, myocarditis, oophoritis, pancreatitis, retinopathy, thrombocytopenic purpura, thyroid disease, urticarial, axonal and neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy, chronic recurrent multifocal osteomyelitis, Churg-Strauss syndrome, cicatricial pemphigoid/benign mucosal pemphigoid, Crohn's disease, Cogans syndrome, cold allutinin disease, congenital heart block, Coxsacke myocarditis, CREST disease, essential mixed cryoglobulinemia, demyelinating neuropathies, dermatitis herpetiformis, dermatomyositis, Devic's disease, discoid lupus, Dressler' syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura, IgA nephropathy, IgG4-related sclerosing disease, immunoregulatory lipoproteins, inclusion body myositis, interstitial cystitis, juvenial arthritis, juvenial diabetes (Type 1 diabetes), juvenile myositis, Kawasaki syndrome, Lamber-Eaton syndrome, leukocytoclastic vasculitis, lichen planus, lichen sclerosus, ligneous conjunctivitis, linear IgA disease, lupus, lyme disease, Meniere's disease, microscopic polyangiitis, mixed connective tissue disease, Mooren's ulcer, Mucha-Habermann disease, multiple sclerosis, myasthenia gravis, myositis, narcolepsy, neuromyelitis optica, neutropenia, ocular cicatricial pemphigoid, optic neuritis, palindromic rheumatism, PANDAS, paraneoplastic cerebellar degeneration, paroxysmal nocturnal hemoglobinuria, Parry Romber syndrome, Parsonnage-Turner syndrome, pars planitis, pemphigus, peripheral neuropathy, perivenous encephalomyelitis, pernicious anemia, POEMS syndrome, polyarteritis *nodosa*, Type I, II and III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gengrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis/giant cell arteritis, thrombocytopenic purpura, Tolosa-Hunt syndrome, transverse myelitis, Type 1 diabetes, ulcerative colitis, undifferentiated connective tissue disease, uveitis, vasculitis, vesiculobullous dermatosis, vitiligo, and Wegener's granulomatosis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); i.n., intranasal(ly); i.v., intravenous(ly); s.c., subcutaneous(ly); M/ml, million units or $10^6$ CFU/ml; M, million units/mouse or $10^6$ CFU/mouse; and the like.

Materials and Methods

The following materials and methods were used in the Examples described below.

Materials

RPMI serum-free media was obtained from the Life Technologies (Burlington, Ontario, Canada). RPMI was supplemented with 5-10% fetal bovine serum, sodium pyruvate, Penicillin-streptomycin and 2-mercapto-ethanol to make complete medium, which was used in various cell cultures. ConA, PWM and LPS were obtained from Sigma Chemical Company. Cytokine kits and fluorescent-labeled anti-mouse antibodies were purchased from eBioscience (San Diego, Calif.). Anti mouse FOXP3 was purchased from biolegend (San Diego, Calif.). Aldra cream (5% imiquimod) was obtained University of Alberta Hospital pharmacy. Wild-type and lipopolysaccharide (LPS)-negative *Caulobacter crescentus* ($LPS^{-ve}$ CC) were grown at room temperature (22-27° C.) in the incubator, and stored in saline at 4° C. or room temperature for various time periods. Wild-type *Caulobacter vibroides* (CV) was grown at room temperature (22-27° C.) in the incubator, and stored in saline at 4° C. or room temperature for various time periods.

Methods

Mice 6-8 Weeks old C57BL/6 or 9-11 week BALB/c, male or female mice were purchased from Charles River Breeding Laboratories. All animal experimental protocols used in this study were approved by the University of Alberta Animal Care and Use Committee for Health Sciences, and conducted in accordance with the guidelines of the University of Alberta, Edmonton, Canada Treatments of Mice and Sample Collections The mice were administered single or multiple times with *Caulobacter crescentus* (CC) in PBS using doses, schedule and routes as described in different examples and figure legends. CC used was prepared in two formats: CC-1 (CC grown in liquid PYE medium and stored at room temperature in saline), and CC-2 (CC grown in liquid PYE medium and stored at 4° C. in refrigerator). CC-2 has also been referred to as CC in figures and description.

After euthanization of mice at specific times, blood, spleen, lungs, liver, lymph nodes, etc. were collected. Serum samples were used to determine biochemical markers using commercial Vet test kits (Idexx Laboratories).

Isolation of Lymphocytes from Spleen

At specific times after immunization, the mice were euthanized to obtain splenocytes. The spleens were pooled from 3-5 mice and ground to a single cell suspension and filtered through a Falcon 100 µm nylon cell strainer. After centrifugation, the cell pellet was resuspended in 2 ml of sterile distilled water and briefly vortexed. Immediately, 2×PBS were added and after a brief vortex the volume was made to 25 ml with 1×PBS. The tube was centrifuged and the cell pellet was resuspended in 10 ml of complete RPMI. It was again filtered through a Falcon 100 µm nylon cell strainer and centrifuged. The cell pellet was resuspended in 2 ml of RPMI media. These lymphocytes were used for the experiment.

Mouse Cytokine ELISA

Cytokines and chemokines secreted in the supernatant of proliferating co-cultures, or mouse serum samples were measured using sandwich enzyme-linked immunosorbent assay (ELISA) kits following the manufacturer's protocol (eBioscience, CA, USA) for the presence of IL-10, GM-CSF, IL-17A, IFN-γ, TNF-α, IL-2, IL-6, IL-1βIL-22, MIP-1α, IL-8/KC. A dilution of 1:2 to 1:50 was used for the samples with the standards ranging from 5 to 2,000 µg/ml.

Finally the ELISA plates were read and the concentrations were calculated with an automated ELISA plate reader (Fluostar Optima, BMG Labtech).

Evaluation of Antibody Responses

The levels of antibodies (IgG, IgG2a, IgE) in serum and lung washes were determined using enzyme-linked immunosorbent assays (ELISAs). Briefly, 96-well nitrocellulose (Nunc) plates were coated with relevant antigen (such as OVA, MOG peptide) and incubated overnight at 4° C. The plates were blocked with PBS containing normal mouse serum, followed by incubating with the experimental samples at different dilutions for 2 hrs at room temperature. After washing the plates for 4 times, Anti mouse Ig isotype antibodies conjugated with Alkaline phosphatase (AP) were added, followed by incubation for 2 hrs. After washing the plates, PNPP substrate was added and color development was read on Fluostar ELISA reader at 405 nm wavelength. All reagents for antibody detection were obtained from Southern Biotech (Birmingham, Ala.).

T Cell Proliferation Assay

Proliferative responses of splenic T cells were measured in triplicate cultures in 96-well flat-bottomed microtiter plates. A total of $4 \times 10^5$ spleen T cells from immunized mice and $4 \times 10^5$ antigen-presenting cells (APCs) (spleen cells from control syngeneic mice irradiated with 18 Gy) were mixed with different concentrations (0.1, 1 and 10 μg/mL) of MOG peptide were cultured in RPMI medium (with 10% fetal bovine serum (FBS)) at 37° C. (5% $CO_2$) for 4 days. The cells were pulsed with 0.5 μCi/well [$^3$H]-thymidine (Amersham) for 12-18 h and harvested on filter papers (Perkin Elmer). The levels of [$^3$H]-thymidine incorporated into the DNA of proliferating cells were counted in a Microbeta Trilux liquid scintillation counter (Perkin Elmer). Proliferation is represented as the mean cpm±SE (standard error) of triplicate cultures.

Flow Cytometry Analysis of Surface Markers, Intracellular IL-10 and Foxp3

A total of $5 \times 10^5$ cells from immunized mice were taken for intracellular and extracellular staining with multicolor fluorescently labeled mAbs (concentrations according to manufacturer's instructions). The cells were incubated with Fc mouse-serum (Sigma) to prevent non-specific binding and washed with fluorescence-activated cell sorter (FACS)-buffer (2% fetal bovine serum in 1× phosphate-buffered saline (PBS). After incubation for 30 minutes with anti-mouse CD3e-FITC, CD4-PECy-5, CD25-PE-Cy7, CD8a-APC-Cy7, anti-PD-1-PerCP eFluore 710, anti-CD49b-Alexafluor-700 (for BALB/c and C57bl/6 mice) etc. (eBioscience) for extracellular markers at 4° C., the cells were washed twice and fixed in fixative solution (1% paraformaldehyde in FACS-buffer) for 5 minutes. After washing twice, the cells were incubated with cold permeabilization buffer (FACS-buffer+0.3% Saponin (Sigma)+5% normal human serum in PBS) for 5 minutes followed by addition of anti-mouse IL-10 (eBioscience) and anti-Foxp3-PE (biolegend) and further incubated for 30 minutes at 4° C. The cells were washed once with FACS-buffer containing 1% Saponin and fixed. They were read in Fortessa and analyzed using FACS-DIVA software (Becton Dickinson, Mountain View, Calif.). Each marker was gated based on its respective isotype-matched control monoclonal antibodies.

Human PBMCs and DCs

Peripheral blood mononuclear cells (PBMCs) were obtained from normal human donors using Ficoll-Paque. To obtain dendritic cells (DCs), adherent PBMCs were cultured with recombinant GM-CSF and IL-4 for 5-6 days in RPMI media, using procedures well established in the literature. Human PBMCs cultured with test materials for specified times as described in individual examples were stained with antibodies against CD34, CD45, CD11c and CD11b, labeled with various fluorophores obtained commercially (eBiosciences), using standard procedures.

Results

The following examples are intended to illustrate rather than limit the scope of the invention.

The immunomodulatory effects of CC were tested alone and with different antigens in different models and indications via systemic and mucosal routes as follows.

Example 1: Effect of *Caulobacter crescentus* (CC) on Modulation of Inflammatory Cytokines in Concanavalin A (ConA) Stimulated Splenocytes Upon Oral and Intranasal Administration of CC in Healthy Mice C57/bl6 male mice were treated twice weekly orally or intranasally for five times with CC at $500 \times 10^6$ CFU/mouse or PBS control. Mice were euthanized 8 days after the last treatment. The spleens isolated and ex-vivo stimulated with T cell mitogen ConA at 1 ug/ml concentration for 24 hrs. Supernatant were collected and cytokines (IFN-γ, TNF-α, IL-6, and IL-17A) were measured using ELISA (FIG. 1). These results demonstrate that treatment with CC down-regulates production of inflammatory cytokines in splenocytes upon ex-vivo stimulation with Con A and suggest the role of CC in suppressing inflammation mediated by T cells from a variety of infections including viral, bacterial, fungal as well as from environmental toxins, drug reactions and autoimmune disorders.

Figure 2:
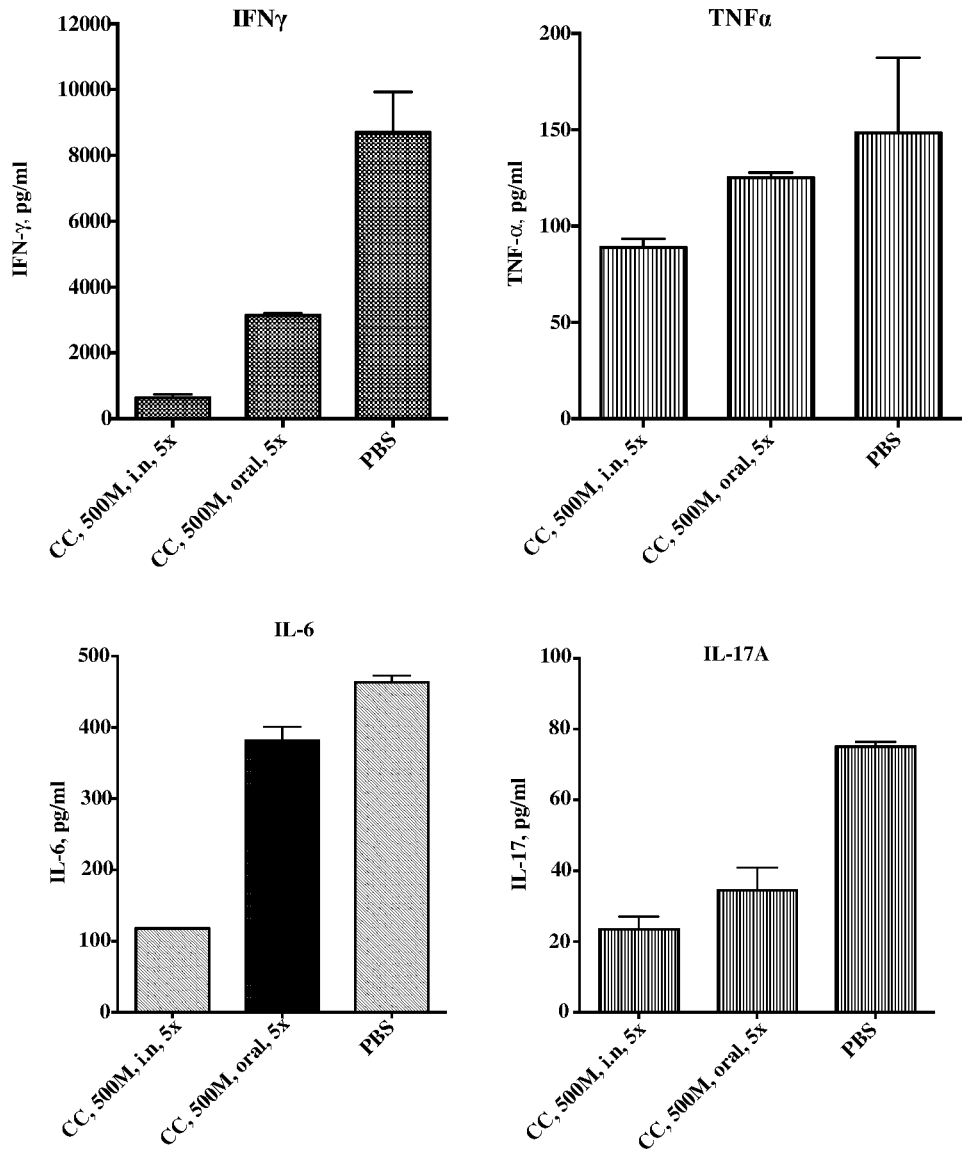
FIG. 2 demonstrates the reduction in pokeweed mitogen (PWM) induced pro-inflammatory cytokines (IFN-γ, TNF-α, IL-6 and IL-17A) production in splenocytes isolated from CC and phosphate buffered saline (PBS) treated mice by intranasal and oral routes twice weekly. Data are expressed in pg/ml and shown as average±SD of triplicates.

Example 2: Effect of *Caulobacter crescentus* (CC) on Modulation of Inflammatory Cytokines from Pokeweed (PWM) Stimulated Splenocytes Upon Oral and Intranasal Administration of CC in Healthy Mice C57/bl6 male mice were treated twice weekly orally or intranasally for five times with CC at $500 \times 10^6$ CFU/mouse or PBS control. Mice were euthanized 8 days after the last treatment. The spleens of treated mice were isolated and ex-vivo stimulated with a B cell mitogen PWM at 0.1 ug/ml concentration for 24 hrs. Supernatant were collected for cytokines (IFN-γ, TNF-α, IL-6 and IL-17A) measurements using ELISA (FIG. 2). These results demonstrate that treatment with CC down-regulates production of inflammatory cytokines in splenocytes upon ex-vivo stimulation with PWM and suggest the role of CC in reducing excessive production of proinflammatory cytokines in infection and non-infection related systemic inflammatory disorders.

Example 3: Effect of *Caulobacter crescentus* (CC) on Induction of Anti-Inflammatory Cytokine IL-10 In Vivo Upon Oral and Intranasal Administration Groups of five C57/bl6 male mice were treated twice weekly orally or intranasally for five times with CC at $500 \times 10^6$ CFU/mouse or PBS control. Mice were euthanized 8 days after the last treatment and spleens were isolated. Splenocytes were cultured with media, ConA and PWM for 24 hr. Supernatant were collected for IL-10 measurement using ELISA (FIG. 3A-FIG. 3C). The results obtained demonstrate that CC up-regulates IL-10 production ex-vivo in splenocytes upon 24 hr culture with or without stimulants and suggest that CC can induce IL-10 production in vivo.

These results also indicate systemic immunomodulatory and anti-inflammatory role of CC in reestablishing homeostatic balance in inflammatory conditions.

Figure 3:
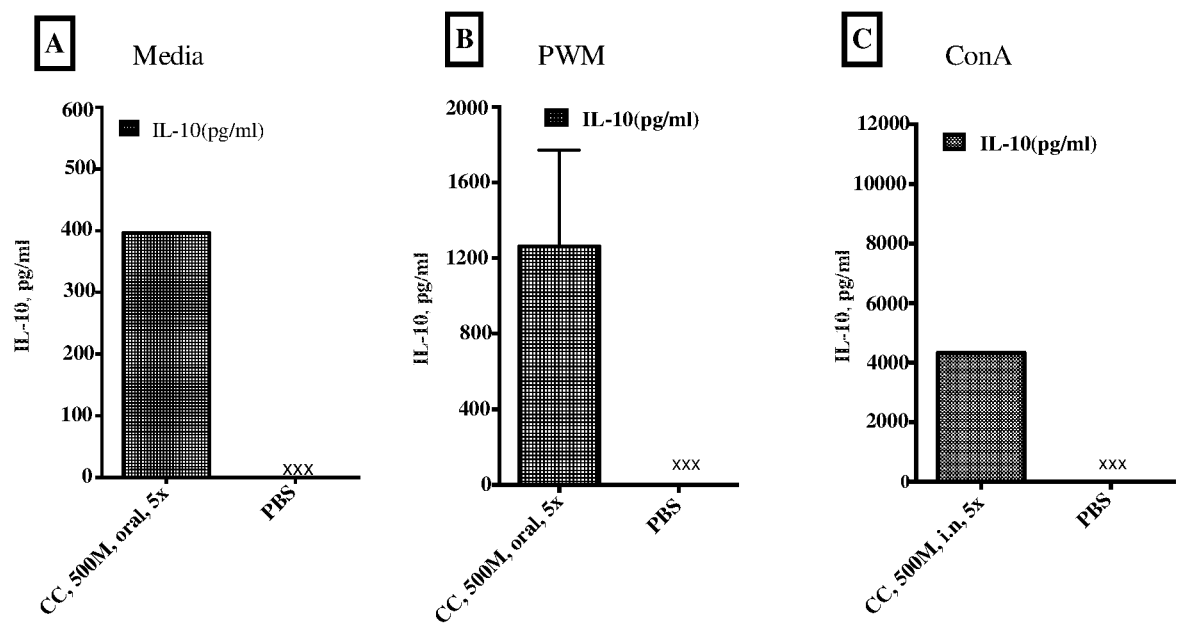
FIG. 3A-3C illustrate the induction of IL-10 in splenocytes isolated from CC and PBS treated mice by intranasal and oral routes twice weekly and stimulated ex vivo for 24 h with medium (A), PWM (B) and ConA (C). Data are expressed in pg/ml and shown as average+SD of triplicates.

Overall, results described in FIG. 1, FIG. 2, and FIG. 3 suggest that CC has capacity to induce higher levels of the anti-inflammatory cytokine IL-10 and down-regulate levels of inflammatory cytokines IFN-γ, TNF-α, IL-6 and IL-17A. Pro-inflammatory cytokines play a major role in the pathogenesis of many diseases and hence there is an interest in developing therapeutics to modulate their excessive production in a range of afflicted diseases.

Figure 4:
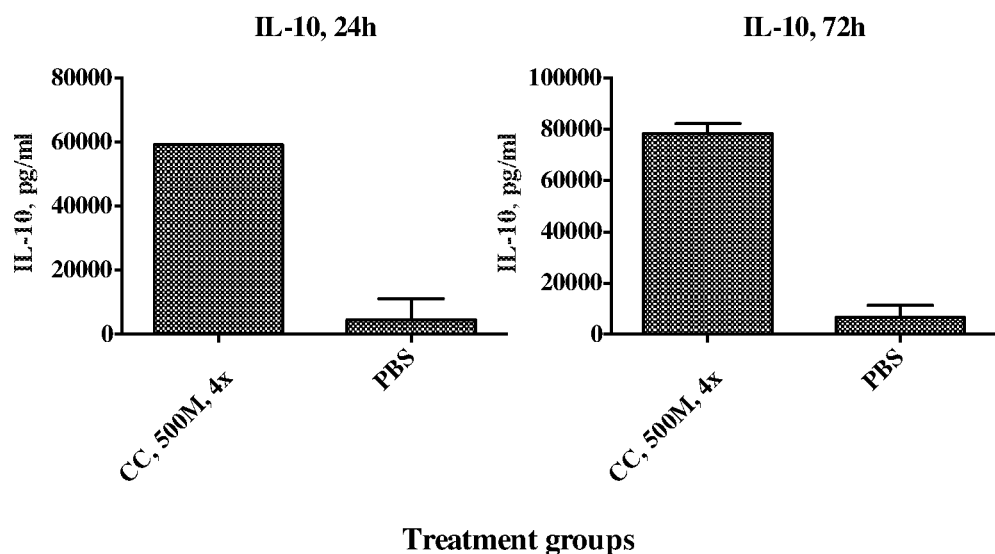
FIG. 4 illustrates the induction profile of IL-10 in splenocytes isolated from CC and PBS treated mice orally twice a week. Cells were stimulated in vitro with LPS for 24 or 72 hrs.

Example 4: Effect of *Caulobacter crescentus* (CC) on IL-10 Production from Ex Vivo LPS-Stimulated Splenocytes Isolated from CC Treated Mice Female C57/bl6 mice were treated twice weekly orally via gavage for four times with CC at $500 \times 10^6$ CFU/mouse or PBS control. Mice were euthanized 4 days after the last treatment and spleens were collected. Splenocytes were stimulated with LPS at 1 ug/ml concentration for 24 and 72 hrs. Supernatants were collected and IL-10 was measured using ELISA (FIG. 4). The results obtained demonstrate that CC upregulates IL-10 production ex-vivo in splenocytes upon LPS stimulation compared to placebo group (PBS). These studies suggest the anti-inflammatory activity of CC in normalizing the dysregulated release of pro-inflammatory cytokines and protection against inflammatory responses and/or autoimmune disorders.

Figure 5:
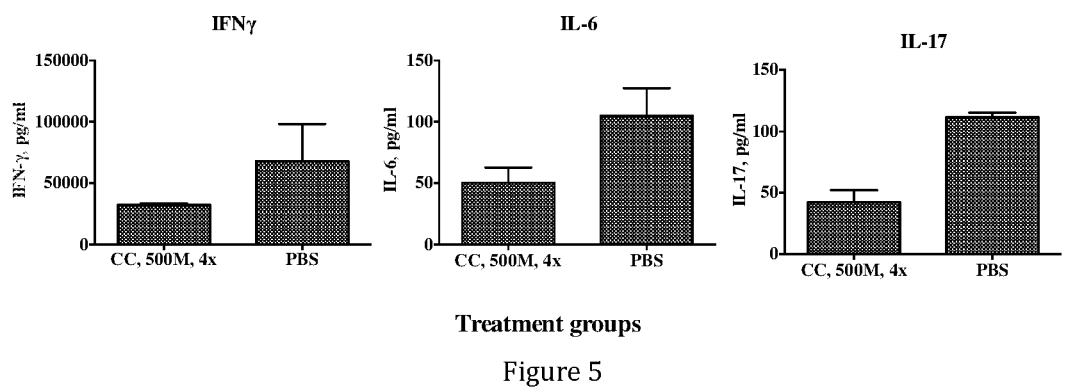
FIG. 5 shows the reduction profile of cytokines (IFN-γ, IL-6 and IL-17A) in mesenteric lymph nodes isolated from CC and PBS administered mice orally twice a week. Cells were stimulated in vitro with lipopolysaccharide (LPS) for 24 hrs. Data are shown as average+SD.

Example 5: Effect of *Caulobacter crescentus* (CC) on Pro-Inflammatory Cytokines in Gut-Associated Mesenteric Lymph Nodes Upon Oral Treatment In order to determine the effect of CC on inflammatory cytokines levels in intestinal lymphoid tissue, female C57/bl6 mice were treated twice weekly orally for four times with CC at $500 \times 10^6$ CFU/mouse or PBS control. Three days after the last treatment, mice were euthanized and local mesenteric lymph nodes were collected. Cytokines levels were determined in supernatant collected after 24 hr LPS stimulation. Oral administration of CC led to decrease in the levels of IFN-γ, IL-6 and IL-17A compared to PBS group (FIG. 5). These results demonstrated that CC can down-regulates production of Th1 and Th17 cytokines in local mesenteric lymph nodes. Thus, CC has ability to reduce TH1 and/or TH17 mediated pro-inflammatory cytokine levels in a variety of inflammatory disorders where immune dysregulation and inflammation is triggered by external or internal stimuli or microorgamisms such as Gram+ and Gram− bacteria, viruses, fungi, parasites, LPS, toxins, autoantigens, glycosylphosphatidyl-inositol, tissue injury (trauma, burns) etc.

Figure 6:
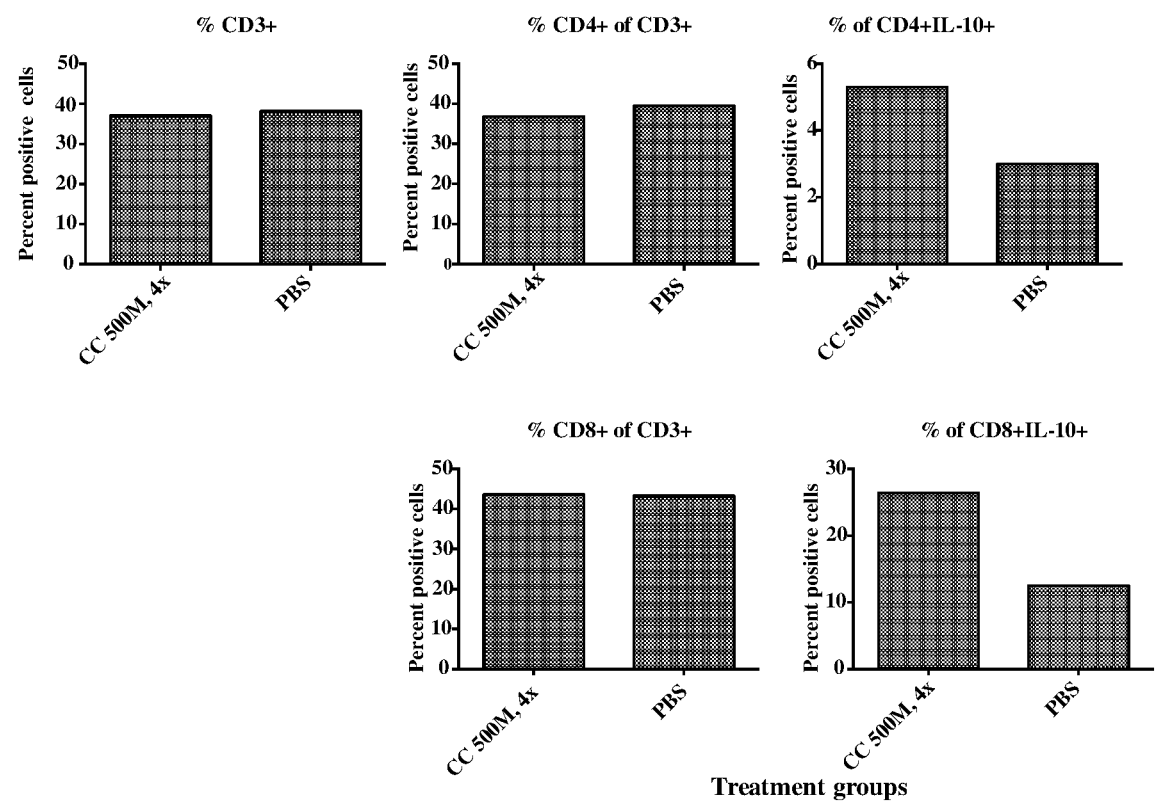
FIG. 6 illustrates the enhancement of IL-10 producing CD4+ and CD8+ T cells in splenocytes isolated from CC and PBS fed mice twice weekly. Percent of cells positive for CD3 and CD4 or CD8, expressing intracellular IL-10 are presented.

Example 6: Effect of *Caulobacter crescentus* (CC) in Systemic Immune Modulation in Mice after Oral Treatment Female C57/bl6 mice were treated orally twice weekly for four times with CC at $500 \times 10^6$ CFU/mouse or PBS control. Mice were euthanized 4 days after the last treatment and spleens were collected. The percentage of CD3+CD4+ and CD3+CD8+ cells expressing IL-10$^+$ were analyzed by flow cytometry. Treatment with CC led to increased expression of intracellular IL-10 on both CD4$^+$ and CD8$^+$ T cells in splenocytes (FIG. 6). Taken together, the results shown in FIG. 4-FIG. 6 demonstrate that CC has strong ability to normalize immune dysregulation both locally and systemically in inflammatory and autoimmune disorders.

Figure 7:
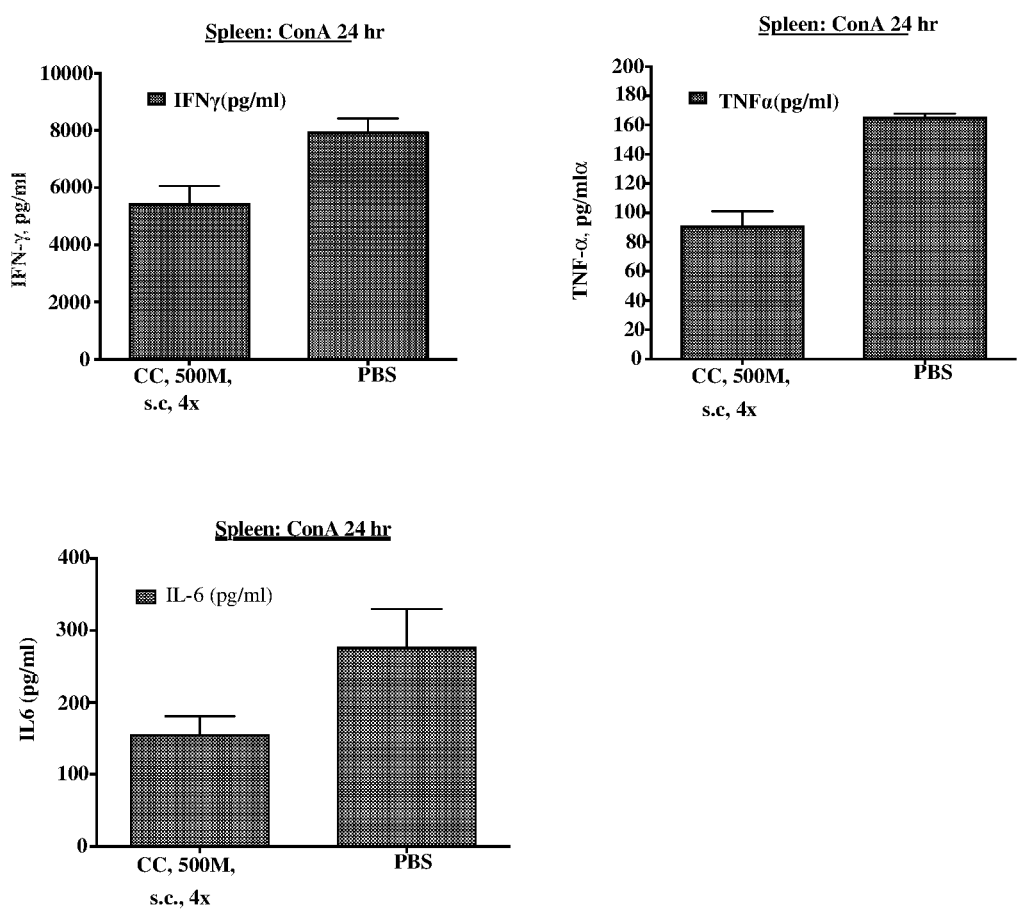
FIG. 7 demonstrates the modulation in ConA induced pro-inflammatory cytokines (IFN-γ, TNF-α and IL-6) production in splenocytes isolated from CC and PBS treated mice by subcutaneous route once weekly. Data are expressed in pg/ml and shown as average+SD of triplicates.

Example 7: Effect of *Caulobacter crescentus* (CC) on Modulation of Pro-Inflammatory Cytokine Production in Spleen after Subcutaneous Treatment Groups of three C57/bl6 male mice were administered with CC ($500 \times 10^6$ CFU/mouse) or PBS once weekly for four weeks by subcutaneous route. Mice were euthanized 28 days after the last treatment. Spleens were harvested and splenocytes were cultured with ConA. Cytokines levels were determined in supernatant collected after 24 hr ConA stimulation. The results presented in FIG. 7 show that CC led to persistent modulation in the production of IFN-γ, TNF-α and IL-6 cytokines (FIG. 7). Thus, CC can provide long-lasting immunomodulatory effect even after cessation of therapy.

Example 8: Modulation of Innate and Adaptive Immune Cells after Oral Treatment with *Caulobacter crescentus* (CC)

Figure 8:
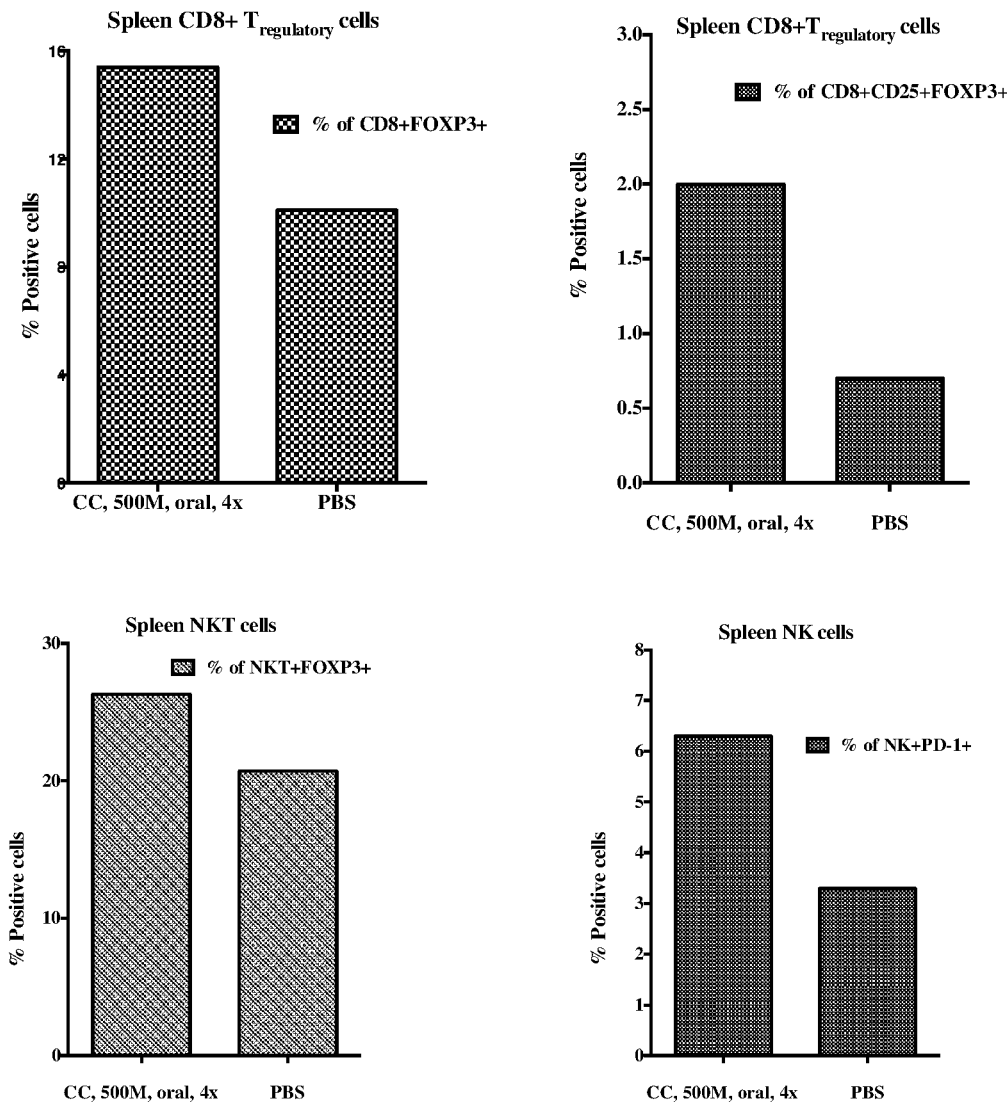
FIG. 8 demonstrates the induction of regulatory lymphocytes (CD8 T cells, NKT cells and NK cells) in mice treated with CC or PBS orally once weekly. The data represent $CD3^+CD8^+$, CD3+CD49b+ and $CD3-CD49b^+$ populations expressing CD25, FoxP3 or PD-1.

Groups of three C57/bl6 male mice were treated orally with CC ($500 \times 10^6$ CFU/mouse) or PBS once weekly for four weeks. Mice were euthanized 28 days after the last treatment and splenocytes were harvested and analyzed by flow cytometry. Oral treatment with CC led to increased FOXP3 expression on CD8$^+$, CD8$^+$CD25$^+$ and NKT (CD3$^+$CD49b$^+$) cells and increased PD-1 expression on NK cells (FIG. 8). Thus CC induces various regulatory lymphocytes to control inflammation. This data suggest that CC can induce homeostasis by regulating the expression of different regulatory molecules on innate and adaptive immune cells and therefore, CC can be used to control excessive inflammation in various diseases. PD-1 expression on NK cells has been shown to control inflammatory responses in mycobacterial infection. In addition, PD-1 on NK has also shown to protect from inflammation including viral, bacterial and autoimmune disorders.

NK and/or NKT cells have been shown in down regulating autoimmune responses in several diseases including multiple sclerosis, rheumatoid arthritis, systemic lupus erythematosus, Sjogren's syndrome, autoimmune thyroid disease, psoriasis, Behcet's disease, type I diabetes, neurodegenerative disease etc. Therefore, the present disclosure represents attractive biotherapeutic for the prevention and/or treatment of a range of inflammatory, allergic and autoimmune disorders. Thus, overall the present disclosure represents a strategy to prevent and/or treat systemic and local inflammation in infectious and non-infectious settings through modulating the activity of adaptive and innate T and/or NK and/or NKT cells.

Example 9: Modulation of T Cells in Splenocytes after Subcutaneous Treatment with *Caulobacter crescentus* (CC)

Figure 9:
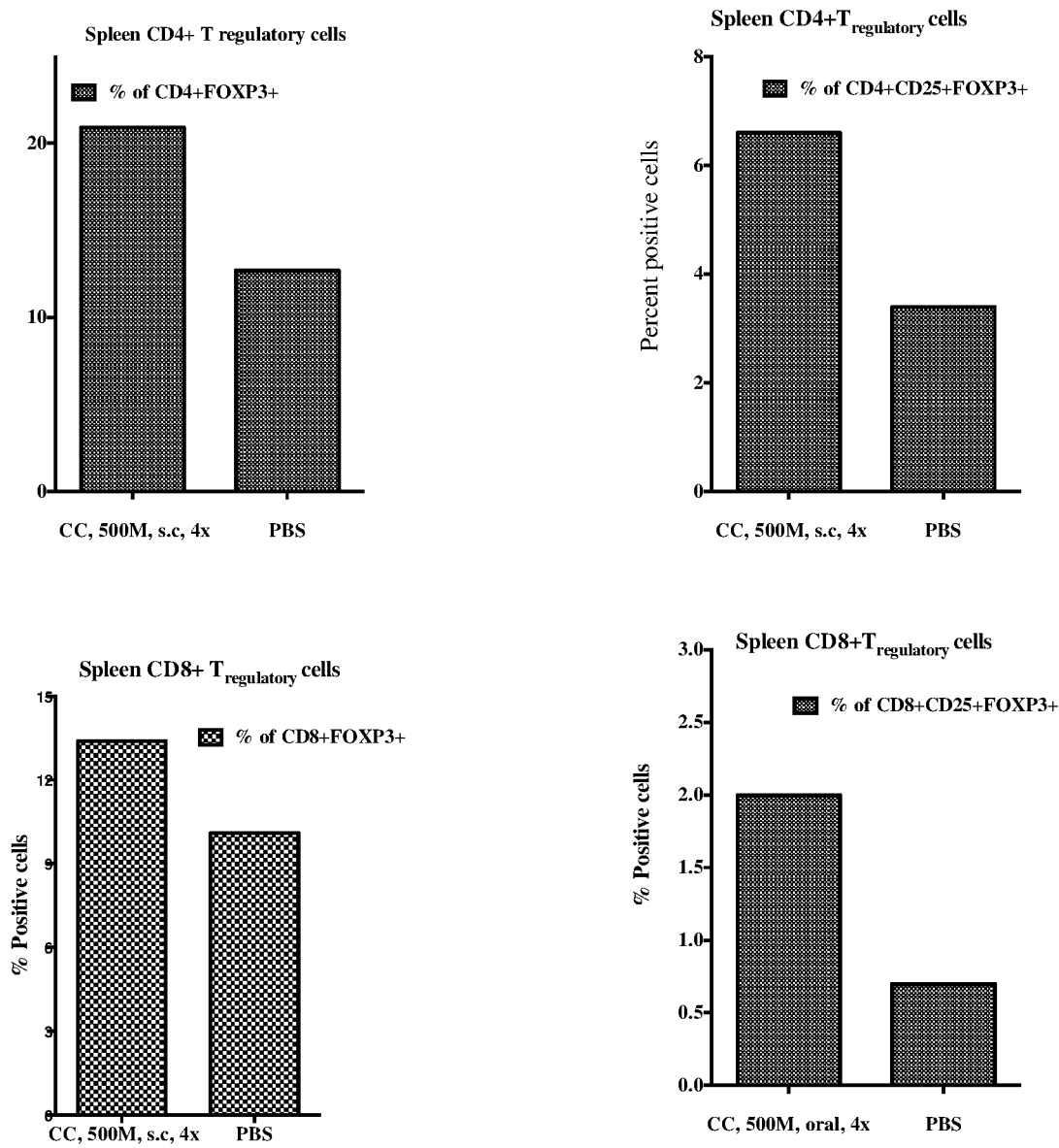
FIG. 9 demonstrates the induction of regulatory lymphocytes (CD4 and CD8 T cells) in mice treated with CC or PBS subcutaneously once weekly. The data represent $CD3^+CD4^+$ and $CD3^+CD8^+$ populations expressing CD25 and FoxP3.

Groups of three C57/bl6 male mice were treated subcutaneously with CC ($500 \times 10^6$ CFU/mouse) or PBS once weekly for four weeks. Mice were euthanized 28 days after the last treatment and splenocytes were harvested and analyzed by flow cytometry. Subcutaneous treatment with CC led to increased FOXP3 expression on CD4$^+$, CD4$^+$CD25$^+$, CD8$^+$ and CD8$^+$CD25$^+$ T cells (FIG. 9). Thus parenteral administration of CC can also provide long-lasting immunomodulatory effects. These results demonstrate the effect of CC in inducing and expanding subsets of regulatory T cells. T regulatory cells have been shown to suppress inflammatory activity in a wide range of diseases including autoimmune encephalomyelitis, IBD, bacterial-induced colitis, type 1 diabetes, airway eosinophilic inflammation, graft vs. host disease, organ transplantation etc.

Figure 10:
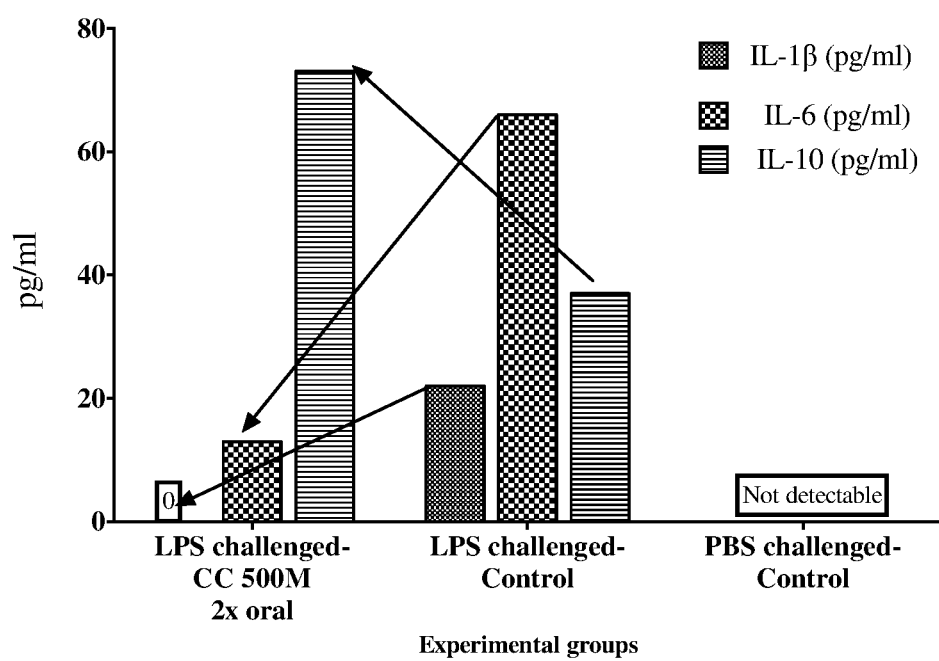
FIG. 10 shows the modulation of IL-1β, IL-6 and IL-10 in sera samples from CC and PBS treated mice orally post 2 hours (hrs) in vivo challenge with LPS at 7 mg/Kg. The LPS challenged mice has dramatic increase in inflammatory cytokines in sera, which were reduced in mice treated with CC. In contrast CC treatment led to an increase in IL-10 levels in LPS challenged mice.

Example 10: *Caulobacter crescentus* (CC) Exhibits Positive Benefits in Controlling Systemic Inflammation in LPS Challenged Model of Sepsis/Inflammation: Modulation of Cytokine Levels in Serum Groups of 3 C57/bl6 male mice were challenged with LPS at 7 mg/Kg in 100 μl PBS intraperitonially and treated orally with CC ($500\times10^6$ CFU/mouse) post 2 and 24 hr in vivo challenge with LPS. Healthy unchallenged and PBS fed mice were also included as controls. Mice were euthanized after the second treatment and blood samples were collected and analyzed for cytokines by ELISA. The LPS challenged mice had high levels of inflammatory cytokines in sera. In contrast, CC treatment down-regulated production of inflammatory cytokines IL-1β and IL-6 and up-regulated the production of anti-inflammatory cytokine IL-10 (FIG. 10). Thus, CC promotes non-damaging immune responses. Induction of IL-1β and IL-6 has been associated with a number of acute and chronic inflammatory and auto-immune diseases such as sepsis, MS, Alzheimers, Parkinsons, RA, gout, metabolic diseases (atherosclerosis, type II diabetes), hypertension, chronic obstructive pulmonary disease (COPD), asthma, psoriasis and allergy. Therefore, CC could help in managing and ameliorating these inflammatory medical conditions.

Figure 11:
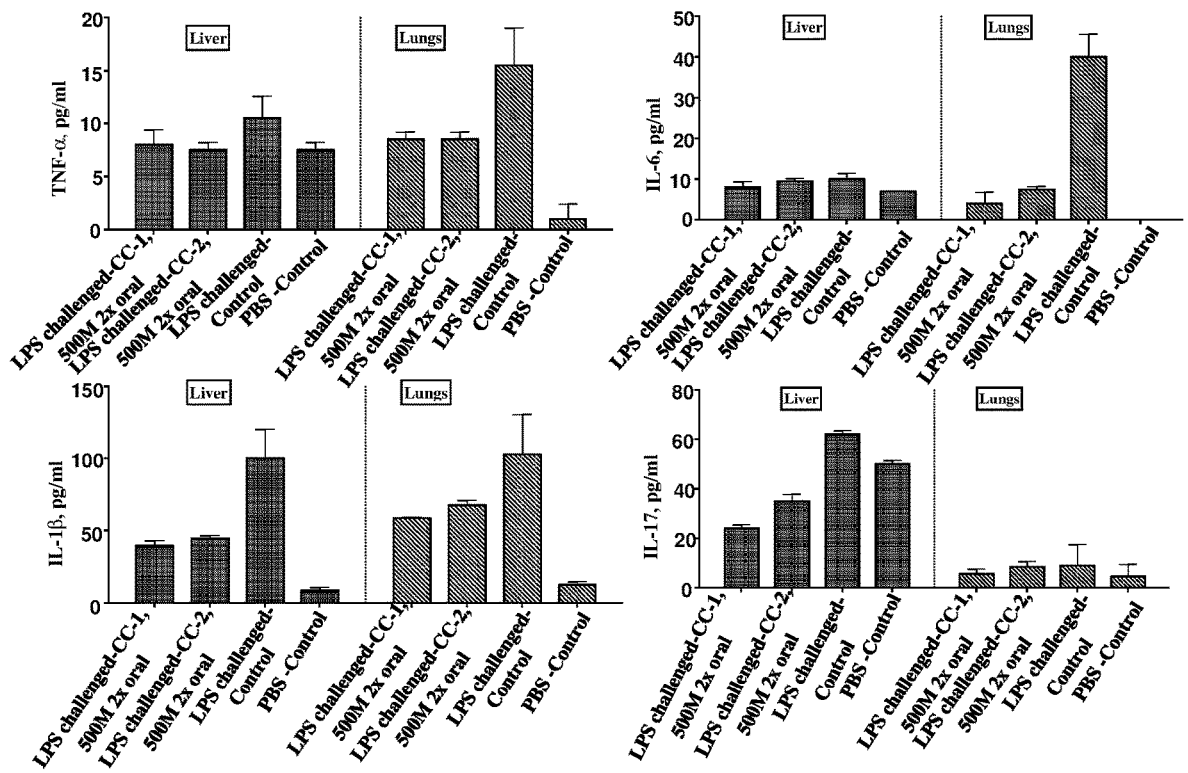
FIG. 11 demonstrates the modulation of TNF-α, IL-6, IL-1β, and IL-17A in liver and lung homogenate samples from CC and PBS treated mice orally post 2 hrs in vivo challenge with LPS at 7 mg/kg. CC used was prepared in two formats: CC-1 (CC grown in liquid peptone yeast extract (PYE) medium and stored at room temperature in saline), and CC-2 (CC grown in liquid PYE medium and stored at 4° C. in refrigerator). Data represent average+SD of triplicate wells.

Example 11: *Caulobacter crescentus* (CC) Exhibits Positive Benefits in Controlling Local Inflammation in a Sepsis/Inflammation Model: Modulation of Cytokine Levels in Lungs and Liver Groups of 3 C57/bl6 male mice were challenged with LPS at 7 mg/Kg in 100 μl PBS intraperitonially and treated orally with CC (500×106 CFU/mouse) post 2 and 24 hr in vivo challenge with LPS. Healthy unchallenged and PBS fed mice were also included as controls. In these studies, CC used was prepared in two formats: CC-1 (CC grown in liquid PYE medium and stored at room temperature in saline), and CC-2 (CC grown in liquid PYE medium and stored at 4° C. in refrigerator). Mice were euthanized after 2nd treatment of CC-1 and CC-2, and lungs and liver were harvested followed by determining cytokines in their homogenates. Both CC-1 and CC-2 down-regulated production of inflammatory cytokines TNF-α, IL-6, IL-1β and IL-17A in lungs and liver, compared to LPS challenged group (FIG. 11). These results demonstrate that CC can be utilized in controlling inflammatory processes and normalizing tissue functions including post-inflammatory medical conditions related to viral and bacterial pathogens, tissue damage, cellular stress, metabolic perturbations etc. in various (intestine, lung, liver, brain, skin, heart etc.) organs. LPS mediated sepsis is a common cause of fatality in critical care, surgical and burn units. Therapeutic approaches directed towards ameliorating LPS mediated fatal inflammatory cascade through targeting host immune components could have clinical and therapeutic advantages.

Figure 12:
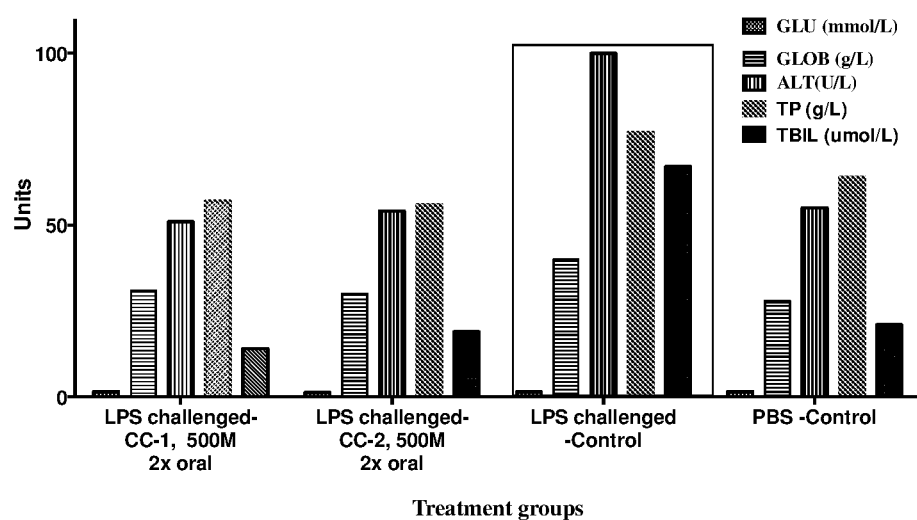
FIG. 12 illustrates the biochemical parameters (GLU: glucose; GLOB: Globulin; ALT: Alanine aminotransferases; TP: total phosphates; TBIL: total bilirubin) in the sera samples from CC and PBS treated mice orally post 2 hrs in vivo challenge with LPS at 7 mg/Kg. CC used was prepared in two formats: CC-1 (CC grown in liquid PYE medium and stored at room temperature in saline), and CC-2 (CC grown in liquid PYE medium and stored at 4° C. in refrigerator).

Example 12: *Caulobacter crescentus* (CC) Exhibits Positive Effects on Biochemical Parameters of Liver Damage in LPS Challenged Mouse Model of Inflammation Groups of 3 C57/bl6 male mice were challenged with LPS at 7 mg/Kg in 100 μl PBS intraperitonially and treated orally with CC ($500\times10^6$ CFU/mouse) post 2 and 24 hr in vivo challenge with LPS. Healthy unchallenged and PBS fed mice were also included as controls. In these studies, CC used was prepared in two formats: CC-1 (CC grown in liquid PYE medium and stored at room temperature in saline), and CC-2 (CC grown in liquid PYE medium and stored at 4° C. in refrigerator). Mice were euthanized after 2nd treatment of CC-1 and CC-2, and blood samples were collected to determine the effects on biochemical markers. Treatment with both CC-1 and CC-2 normalized the serum levels of glucose (GLU), globulin (GLOB), alanine aminotransferases (ALT), total phosphates (TP) and total bilirubin (TBIL) of LPS challenged mice to the levels of non-challenged and PBS fed mice (FIG. 12). These results demonstrate that CC could be used effectively in treating various inflammation mediated disorders including liver associated diseases.

Figure 13:
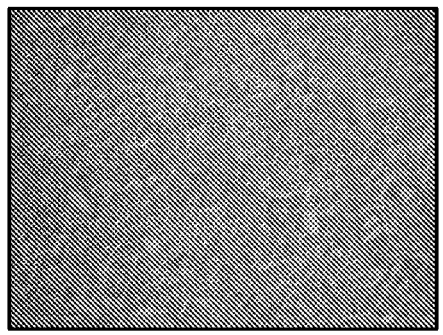
FIG. 13 shows hematoxylin and eosin (H& E) staining of the liver sections isolated from CC and PBS treated mice orally post 2 hrs in vivo challenge with LPS at 7 mg/Kg. CC used was prepared in two formats: CC-1 (CC grown in liquid PYE medium and stored at room temperature in saline), and CC-2 (CC grown in liquid PYE medium and stored at 4° C. in refrigerator).
Figure 13:
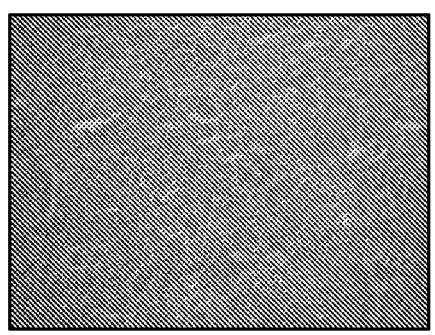
Figure 13:
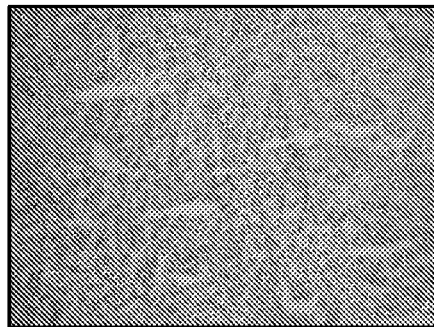
Figure 13:
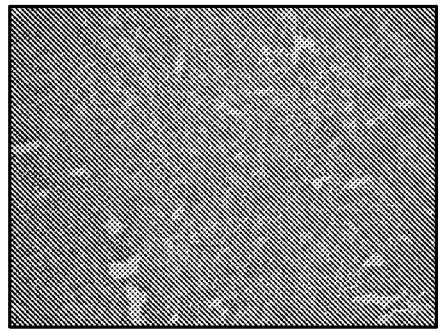

Example 13: *Caulobacter crescentus* (CC) Prevents Liver Injury in LPS Challenged Mice Model Groups of 3 C57/bl6 male mice were challenged with LPS at 7 mg/Kg in 100 μl PBS intraperitonially and treated orally with CC ($500\times10^6$ CFU/mouse) post 2 and 24 hr in vivo challenge with LPS. Healthy unchallenged and PBS fed mice were also included as controls. In these studies, CC used was prepared in two formats: CC-1 (CC grown in liquid PYE medium and stored at room temperature in saline), and CC-2 (CC grown in liquid PYE medium and stored at 4° C. in refrigerator). Mice were euthanized after 2nd treatment of CC-1 and CC-2 and various organs were collected. No inflammation or damage to lung, liver and other organs was observed with both CC-1 and CC-2. H & E staining of liver sections were performed. The results shown in FIG. 13 demonstrate a protective effect of CC administered by oral route in the prevention of LPS induced inflammation and liver damage, compared to LPS challenged mice. Massive destruction of liver has been associated with a number of medical conditions due to undesirable inflammatory activities as a result of infectious and non-infectious pathogenesis. Therefore, CC has strong potential in preventing and ameliorating liver damage from autoimmune hepatitis, alcohol related hepatic disorders, viral mediated hepatitis etc.

Example 14: Modulation of Cytokines in Imiquimod (IMQ)-Induced Psoriasis-Like Dermatitis Mouse Model Upon Oral Treatment with *Caulobacter crescentus* (CC)

Figure 14:
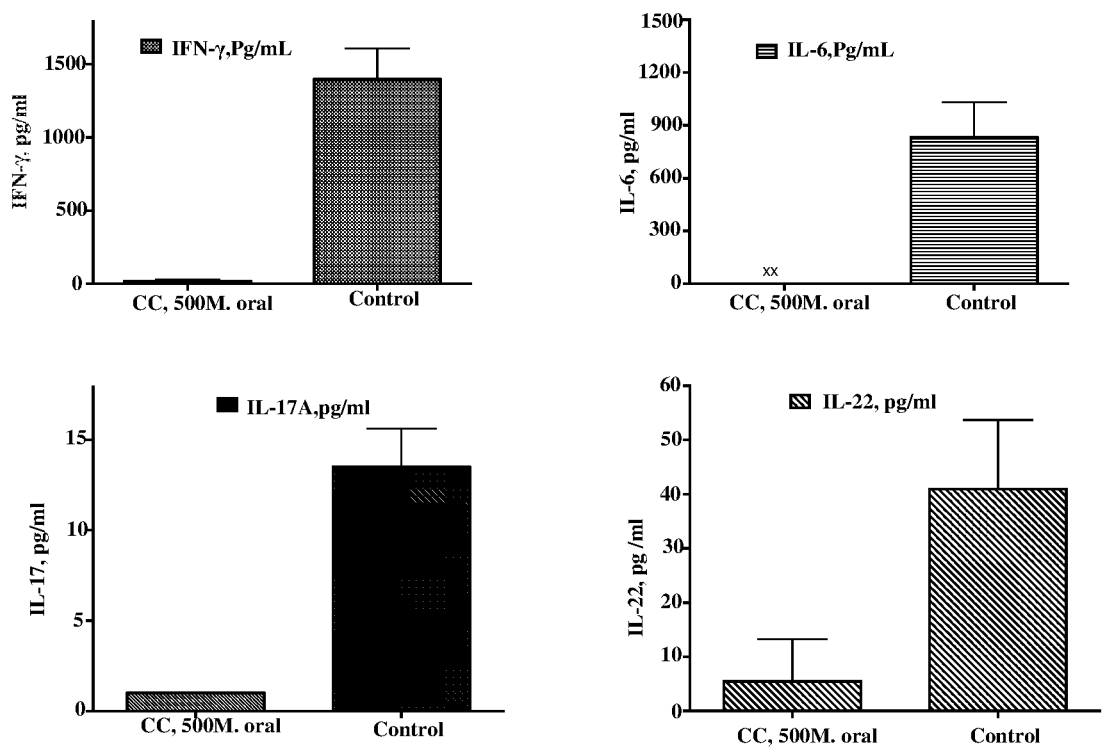
FIG. 14 demonstrates the modulation of cytokines (IFN-γ, IL-6, IL-17A and IL-22) in Aldra (Imiquimod) induced psoriasis mouse model upon two week (5 days/wk) oral treatment with CC and PBS. Splenocytes were harvested from mice and cultured ex vivo for 4 days in medium, followed by collecting supernatant and testing cytokines.

10-11 Weeks old Balb/c female mice were administered a topical dose of 6.25 mg of 5% IMQ cream (Aldra, Imiquimod) for 6 consecutive days on shaved back. Mice were treated orally with CC at $500\times10^6$ CFU/mouse from day 3 (5 days a week for two weeks). Mice were euthanized 3 days after the last treatment and spleens were harvested. Splenocytes were cultured ex vivo with medium for 4 days and culture supernatants were examined for cytokines (FIG. 14). Treatment with CC led to a reduction in the production of IFN-γ, IL-6, IL-17A and IL-22 in Aldra induced psoriasis mice compared to PBS treated psoriatic mice (FIG. 14). These studies suggest that CC can correct cytokine dysregulation in inflammatory and autoimmune diseases and lead to beneficial therapeutic effects. Besides psoriasis, infiltration of immune cells in the dermis and epidermis also occur in other chronic skin diseases such as atopic dermatitis, acne inversa, rosacea etc. Therefore, CC can be used in treating various skin disorders with an inflammatory component. Taken together, the results presented in FIG. 14 demonstrate that CC has systemic immunomodulatory and anti-inflammatory activity to protect against pathogen or autoimmune associated inflammatory responses.

Figure 15:
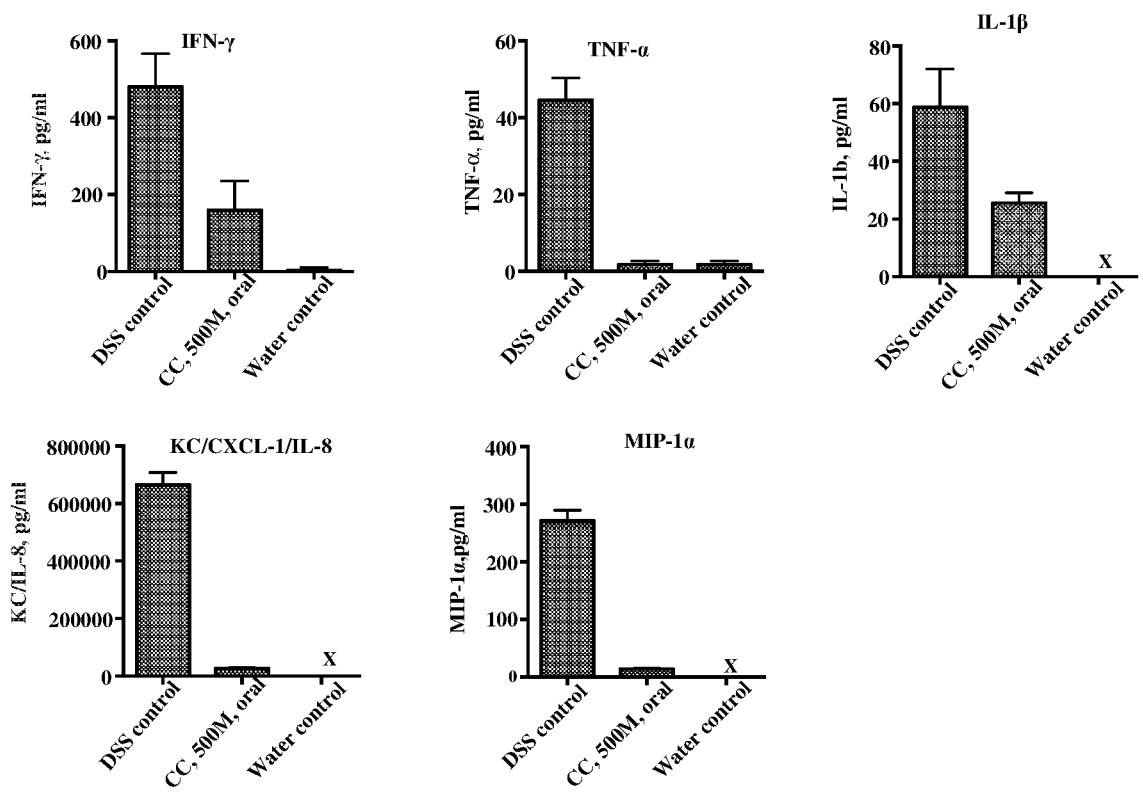
FIG. 15 demonstrates the modulation of cytokines (IFN-γ, TNF-α, IL-1β, IL-8, MIP-1α) in DSS (Dextran sulfate sodium) induced IBD (inflammatory bowel disease) mouse model. Data are expressed in pg/ml and shown as average±SD of triplicates.

Example 15: Effect of *Caulobacter cescentus* (CC) in Reducing Pro-Inflammatory Cytokines and Chemokines in Colon Tissues of DSS-Induced Inflammatory Bowel Disease (IBD) Afflicted Mice Groups of 5 male C57bl/6 were given 3% dextran sulfate sodium (DSS) in drinking water for 7 consecutive days. Mice were treated with CC ($500 \times 10^6$ CFU/mouse) on the same day DSS was started. Water treated mice were used as controls. On day 10, mice were euthanized and colon tissues were harvested and cultured for 24 h. Cytokines were determined in culture supernatants using ELISA. The results obtained indicate that CC reduced pro-inflammatory cytokines IFN-γ, TNF-α, IL-1β, and chemokines IL-8/KC and MIP-1α (FIG. 15). Thus, oral treatment of CC attenuated aberrant levels of inflammatory cytokines and chemokines locally in colon in the murine DSS-induced colitis model for IBD, which account for activation of cascades leading to epithelial permeability, apoptosis, ulceration, diarrhea etc. in IBD.

Figure 16:
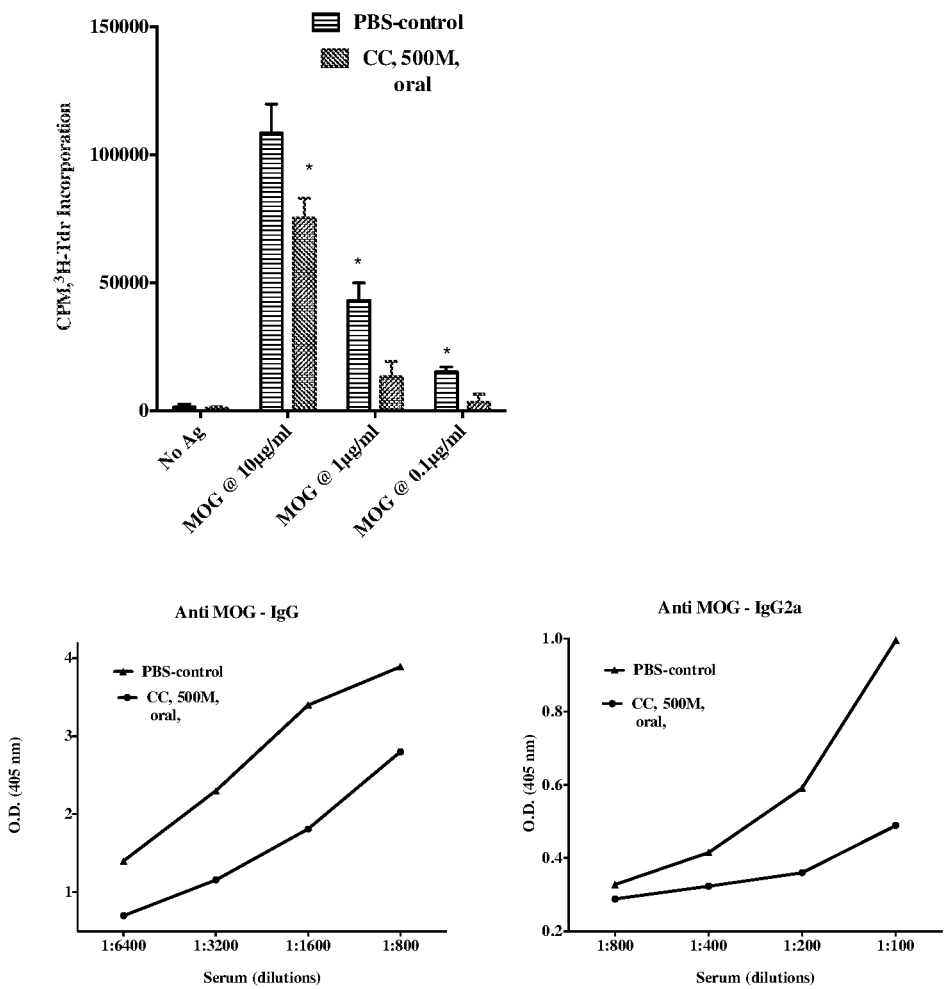
FIG. 16 demonstrates the suppression of autoantigen specific T cell proliferation and antibody (IgG and IgG2a) responses in an experimental autoimmune encephalomyelitis (EAE) mouse model upon oral treatment with CC.

Example 16: Effect of *Caulobacter crescentus* (CC) in Suppressing Auto-Antigen Specific T Cell and Antibody Responses in Experimental Autoimmune Encephalomyelitis (EAE) Model To determine the effect of CC in reducing auto-antigen specific immune responses, groups of five C57Bl6 female mice were immunized with 200 µg $MOG_{35-55}$ peptide emulsified in CFA in 100 µl saline subcutaneously. Additionally, mice received 400 ng of pertussis toxin in 200 µl saline intraperitoneally at day 0 and 3. Starting from day 3 of immunization, mice were treated orally with CC ($500 \times 10^6$ cfu/mouse) continuously every $3^{rd}$ day till the end of the experiment. PBS treated challenged mice were used as controls. Mice were euthanized 30 days after immunization and spleen and blood samples were collected. T cell responses were examined in splenocytes against MOG peptide (10, 1 and 0.1 µg/ml). Anti-MOG antibody (IgG and IgG2a) titers were analyzed by ELISA in serum samples. Interestingly, CC reduced autoantigen-MOG-specific T cell responses compared to PBS control group (FIG. 16). CC also reduced the autoantigen-MOG-specific IgG and IgG2a antibody titers compared to PBS control group (FIG. 16). These results suggest that CC can reduce autoantigen specific T and B cell responses. EAE model is a commonly used model for the human inflammatory demyelinating disease, multiple sclerosis (MS). MS is an inflammatory disease of the central nervous system (CNS). EAE is a complex condition where interaction between immunopathological and neuropathological mechanisms leads to pathological features of MS, viz., inflammation, demyelination, axonal loss and gliosis. Therefore, CC can be effective in treating autoimmune and neurological disorders, autoimmune blood diseases, autoimmune hemolytic anemia etc.

Figure 17:
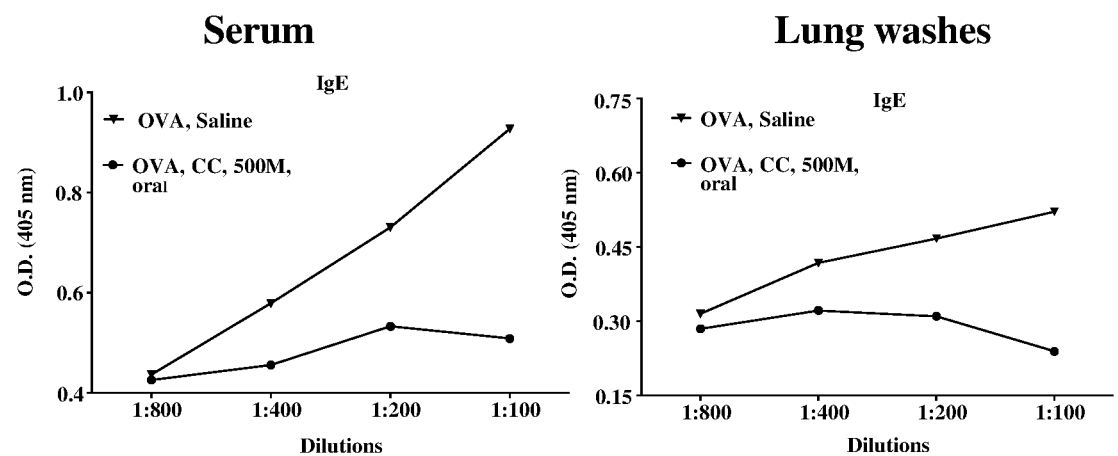
FIG. 17 demonstrates the suppression of allergen specific IgE antibody responses in an ovalbumin-induced allergic airway inflammation model upon oral treatment with CC.
Figure 18:
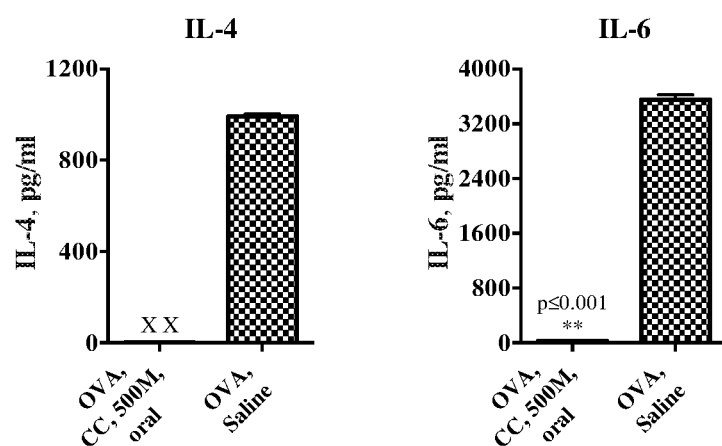
FIG. 18 demonstrates reduction of allergen specific cytokines (IL-4 and IL-6) in spleen in an ovalbumin-induced allergic airway inflammation model upon oral treatment with CC. Data are expressed in pg/ml and shown as average±SD of triplicates.
Figure 19:
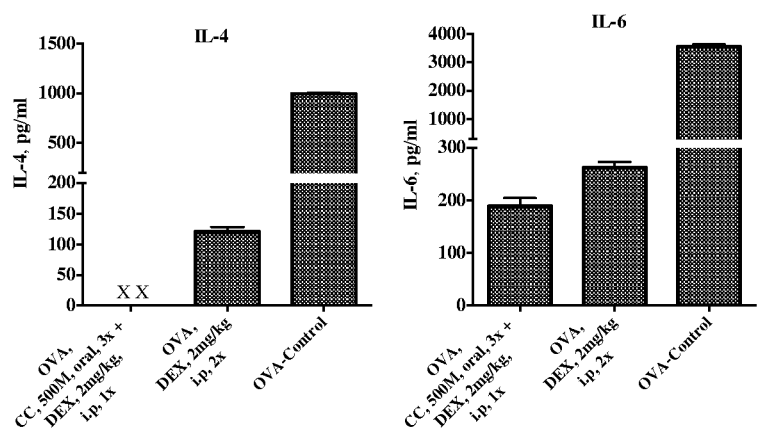
FIG. 19 illustrates reduction of allergen specific cytokines (IL-4 and IL-6) in spleen in an ovalbumin-induced allergic airway inflammation model upon oral treatment with CC+dexamethasone (DEX), DEX alone or no treatment control. Data are expressed in pg/ml and shown as average±SD of triplicates.

Example 17: Effect of *Caulobacter crescentus* (CC) in Reducing Allergen (OVA)-Specific Antibody and Cytokine Responses in a Mouse Model of Ovalbumin-Induced Airway Inflammation Model To determine the effect of CC in airway/lung inflammatory diseases, groups of 5 Balb/c male mice were sensitized on day 1 and day 6 with 10 µg ovalbumin and 2 mg $Al(OH)_3$ in 400 µl saline intraperitoneally. Mice were challenged intranasally (15 µl/nostril) with 50 µg ovalbumin on days 12 and 14. From day 7 onwards of sensitization, mice were treated orally with CC ($500 \times 10^6$ CFU/mouse) every third day up to day 17. In separate groups, mice were treated with dexamethasone (DEX, 2 mg/Kg, i.p.) alone once on day 13 or dexamethasone and CC. Control mice received saline at the same schedule as CC. Mice were euthanized next day of the last treatment, blood samples, lung washes and spleen were collected. A single cell-suspension ($2 \times 10^6$ cells/ml) of splenocytes was cultured with 50 µg OVA for 96 h and cytokines (IL-4 and IL-6) levels were analyzed in culture supernatants by ELISA. Oral treatment with CC reduced the production of OVA specific IgEs in serum and lung washes in mice sensitized with OVA (FIG. 17). It was found that levels of IL-4 and IL-6 were also reduced in spleen by CC treatment (FIG. 18). Combining CC treatment with dexamethasone led to further reduction in IL-4 and IL-6 levels in spleen compared to dexamethasone alone treatment (FIG. 19). These data suggest that treatment with CC prevents OVA-induced allergic airway inflammation in mice. Allergy is a complex disease where multiple immune cells and inflammatory mediators contribute to the initiation and manifestation of allergic diseases. Allergies are most frequently the results of IgE-mediated hypersensitivity reactions. Increased production of IL-4 and IL-6 has been correlated with the allergic diseases. The presence of IgE in serum is a hallmark of allergic diseases driven by IL-4 mediated Ig class switching in B cells. IgE dependent allergic reactions may affect one or more target organs and allergic diseases such as rhinitis, sinusitis, conjunctivitis, asthma, dermatitis, and food allergies etc.

Figure 20:
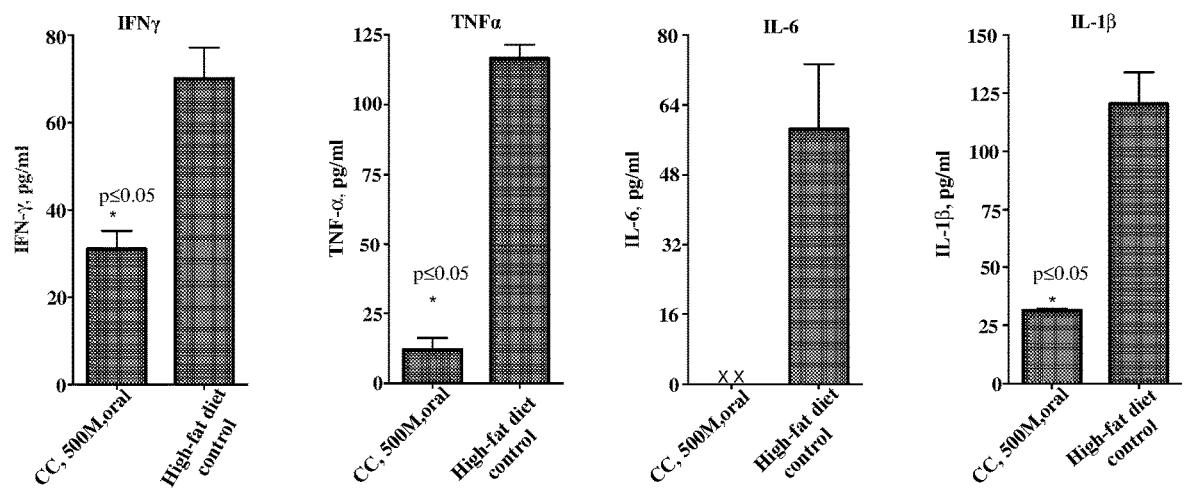
FIG. 20 demonstrates the effect of oral treatment with CC on pro-inflammatory cytokines (IFN-γ, TNF-α, IL-6 and IL-1β) in liver of mice on high fat diet, compared to untreated high-fat diet fed mice. Data were obtained at ~180 days after initiation of high-fat diet and are shown as mean±SD of 5 mice. Data are expressed in pg/ml and shown as average±SD of triplicates.
Figure 21:
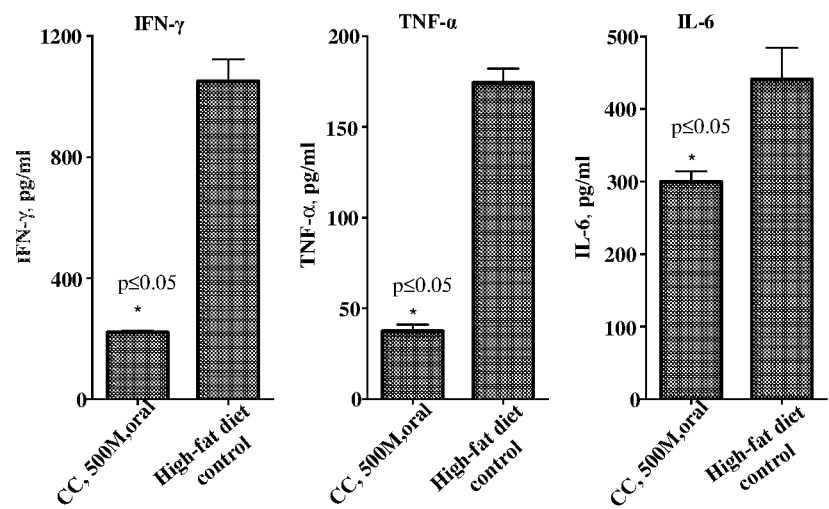
FIG. 21 shows the effect of oral treatment with CC on pro-inflammatory cytokines (IFN-γ, TNF-α and IL-6) in spleen of mice on high fat diet, compared to untreated high-fat diet fed mice. Data were obtained at ~180 days after initiation of high-fat diet and are shown as mean±SD of 5 mice. Data are expressed in pg/ml.
Figure 22:
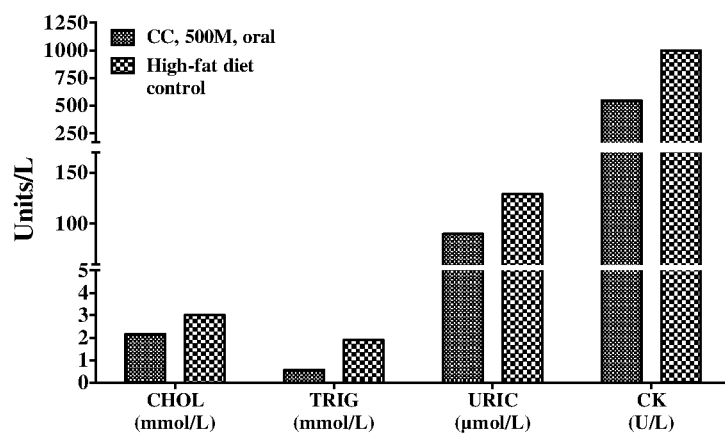
FIG. 22 illustrates the biochemical parameters (CHOL: cholesterol, TRIG: triglycerides, URIC: uric acid, CK: creatine kinase) in the sera samples from CC treated mice on high fat diet, and compared to untreated high fat diet fed mice. Data were obtained at ~180 days after initiation of high-fat diet and are shown as mean of 5 mice.
Figure 23:
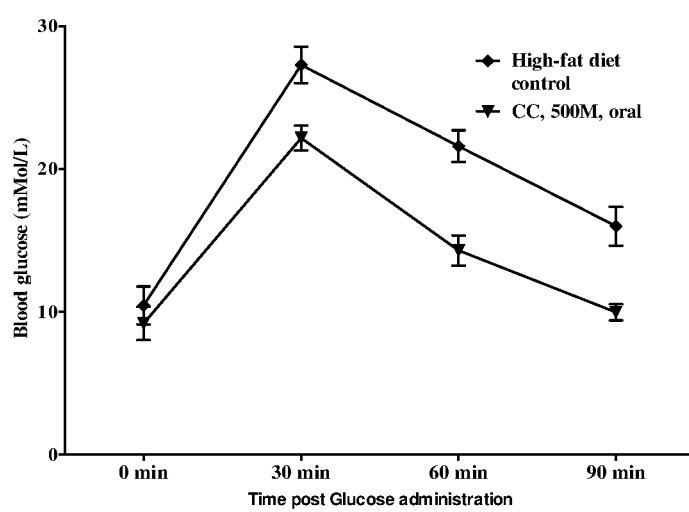
FIG. 23 illustrates the effect of CC on glucose tolerance in mice on high fat diet, compared to untreated high-fat diet fed mice. Data were obtained at ~180 days after initiation of high-fat diet and are shown as mean±SD of 5 mice.

Example 18: Effect of *Caulobacter crescentus* (CC) in Treating Metabolic Disorders and Reducing Systemic Inflammation in High-Fat Diet Induced Obesity Model Groups of five C57bl/6 mice were fed high-fat diet for 4-6 months and treated with CC ($500 \times 10^6$ cfu/mouse) thrice weekly for 4-6 months. PBS treated high-fat diet fed mice were used as controls. Glucose tolerance test was performed prior to terminating the experiment at ~180 days. Blood glucose was measured using OneTouch monitoring system. Mice were euthanized and blood, liver and spleen were collected. Serum samples were used to determine biochemical parameters by Vet test. Liver homogenates were prepared and pro-inflammatory cytokines (IFN-γ, TNF-α, IL-6, IL-1β) were determined by ELISA. Splenocytes ($2 \times 10^6$ cells/ml) were cultured with LPS (1 mg/ml) for 24 h and cytokines (IFN-γ, TNF-α, IL-6) were analyzed in culture supernatants by ELISA. Oral treatment with CC significantly reduced pro-inflammatory cytokines in liver (FIG. 20) and spleen (FIG. 21) compared to high-fat diet control mice, suggesting that CC can effectively reduce chronic and systemic inflammation. Oral treatment with CC also provided positive benefits in biochemical parameters associated with metabolic diseases in high-fat diet induced obesity model (FIG. 22). Further mice on CC treatment demonstrated improved glucose tolerance compared to control group (FIG. 23). It has been well established that obesity is associated with low-grade inflammation contributing to a number of metabolic disorders including type 2 diabetes mellitus, cardiovascular diseases, hypertension, hypercholesterolemia, hypertriglyceridemia, non-alcoholic fatty liver disease, hair loss etc. In obese state, production of a number of inflammatory cytokines and chemokines (e.g., IFN-γ, TNF-α, IL-6, IL-1β etc.) is dysregulated. Obesity is also associated with insulin resistance leading to glucose intolerance, and non-alcoholic fatty liver disease. It has been shown that inhibition of the activity of TNF-α also significantly inhibits the development of steatohepatitis in alcohol-fed animals. High cholesterol is associated with elevated risks of coronary heart disease (atherosclerosis), stroke, peripheral vascular diseases, diabetes, and high blood pressure. Elevated levels of triglycerides are associated with atherosclerosis and also increase the risk of acute pancreatitis. A high uric acid level occurs when kidneys do not eliminate uric acid efficiently. Other factors that may cause high uric acid include obesity, hypothyroidism etc. Build up of uric acid can lead to inflammation and intense pain of a gout attack. An elevated level of creatine kinase is seen in heart attacks, all types of muscular dystrophy, endocrine disorders, neuromuscular diseases etc. Pro-inflammatory cytokines such as TNF-α, IL-6, IFN-γ, IL-1β are known to be involved in obesity, obesity-related pathologies such as type 2 diabetes, insulin-resistance, non-alcoholic fatty liver disease, alcohol-induced liver disease, vascular dysfunction related neurodegenerative processes such as Alzheimer disease, neuropsychiatric disorders such as depression, schizophrenia etc. Mitochondrial reactive oxygen species (ROS) drive pro-inflammatory cytokine (TNF-α, IL-6, IFN-γ, IL-1β) production in chronic human diseases. These studies show that treatment with CC reduces serum biochemical markers associated with metabolic disorders, improves glucose tolerance and reduces pro-inflammatory cytokines in liver in obese mice on high-fat diet.

Figure 24:
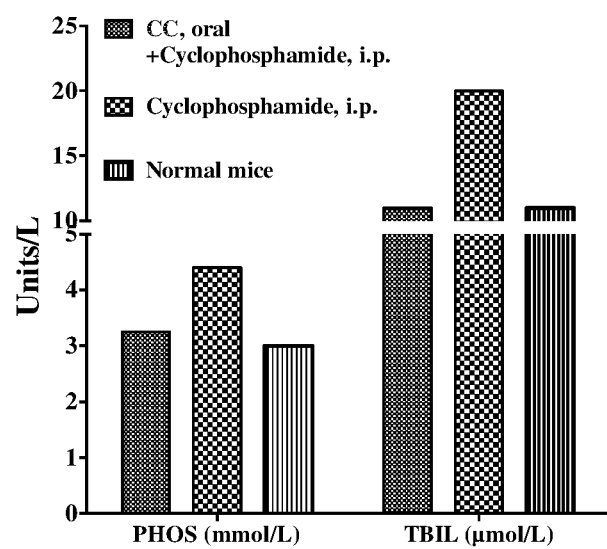
FIG. 24 illustrates the biochemical parameters (PHOS: phosphate; TBIL: total bilirubin) in the sera samples from CC+cyclophosphamide and cyclophosphamide treated mice bearing EL-4 subcutaneous tumor, and compared to normal mice.

Example 19: Effect of *Caulobacter crescentus* (CC) in Reducing Hepato- and Nephro-Toxicities Associated with Anticancer Drug Cyclophosphamide in EL-4 Lymphoma-Bearing Mice To determine the effect of CC in reducing toxicities associated with a therapeutic treatment, groups of five C57B16 mice were challenged with $0.25 \times 10^6$ EL-4 cells/mouse in 100 µl saline subcutaneously in the lower left flank. Starting from day 5 post challenge with EL-4 cells, CC ($50 \times 10^6$ cfu/mouse) was administered once weekly orally. On days seventeen and twenty-one, mice were treated with cyclophosphamide at 150 mg/Kg intraperitoneally. Healthy unchallenged and cyclophosphamide alone treated challenged mice were used as controls. Mice were humanely euthanized 30 days after EL-4 challenge and blood samples were collected. Treatment with CC along with cyclophosphamide normalized the serum levels of phosphate (PHOS) and total bilirubin (TBIL) in EL-4 tumor bearing mice to the levels of non-challenged normal mice (FIG. 24). These results demonstrate that CC could be used effectively in reducing toxicities of anticancer agents or a therapeutic treatment.

Figure 25:
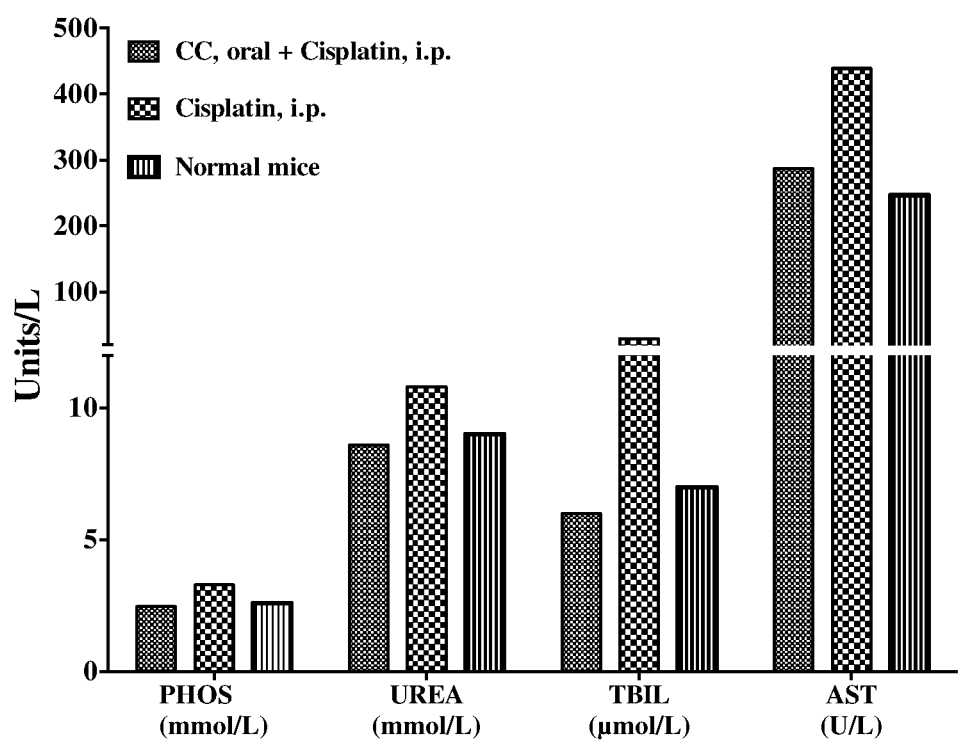
FIG. 25 illustrates the biochemical parameters (PHOS: phosphate; UREA; TBIL: total bilirubin; AST: aspartate aminotransferase) in the sera samples from CC+cisplatin and cisplatin treated mice with B16 metastatic cancer, and compared to normal mice.

Example 20: Effect of *Caulobacter crescentus* (CC) in Reducing Organ Toxicities Associated with Anticancer Drug Cisplatin in B16 Metastatic Cancer Model To determine the effect of CC in reducing toxicity associated with cancer chemotherapy, groups of five C57B16 mice were challenged with $0.4 \times 10^6$ B16 cells/mouse in 100 µl saline intraperitoneally. Mice were treated with cisplatin (4 mg/kg) intraperitoneally at days 7 and 10 post B16 challenge and CC ($50 \times 10^6$ cfu/mouse) was administered orally once weekly. Healthy unchallenged and cisplatin alone treated challenged mice were used as controls. Mice were euthanized 30 days after B16 challenge and blood samples were collected to determine the effects on serum biochemical markers. Treatment with CC along with cisplatin normalized the serum levels of phosphate (PHOS), urea, total bilirubin (TBIL) and aspartate aminotransferase (AST) in B16 metastatic cancer bearing mice to the levels of non-challenged normal mice (FIG. 25). These results demonstrate that CC could be used effectively in reducing toxicities of anticancer agents or a therapeutic treatment.

Figure 26:
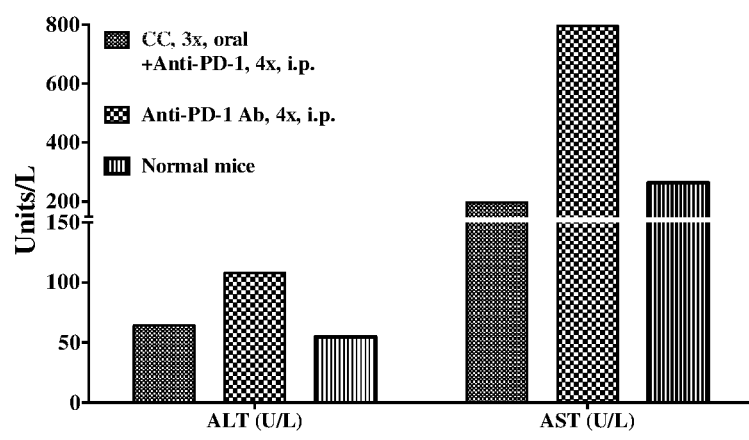
FIG. 26 illustrates the biochemical parameters (ALT: alanine aminotransferases; AST: aspartate aminotransferase) in the sera samples from CC+anti-PD-1 monoclonal antibody and anti-PD-1 monoclonal antibody treated mice with B16 tumor, and compared to normal mice.

Example 21: Effect of *Caulobacter crescentus* (CC) in Reducing Elevated Levels of Biochemical Parameters of Hepatotoxicity Associated with Checkpoint Inhibitor Antibody (Anti-PD-1) in Mouse Model of B16 Melanoma To determine the effect of CC in reducing toxicities associated with therapeutic antibodies, groups of five C57B16 mice were challenged with $0.4 \times 10^6$ B16 cells/mouse in 100 µl saline subcutaneously in the lower left flank. Starting from day 3 post challenge with B16 melanoma cancer cells, CC ($50 \times 10^6$ cfu/mouse) was administered orally once weekly. Two days after first treatment with CC, anti-PD-1 antibody (200 ug/mouse) was administered intraperitoneally and continued every 3-4 days. Healthy unchallenged and anti-PD-1 antibody alone treated challenged mice were used as controls. Mice were euthanized 25 days after tumor challenge and blood samples were collected to determine the effects on biochemical markers. Treatment with CC along with anti-PD-1 monoclonal antibody normalized the serum levels of phosphate alanine aminotransferases (ALT) and aspartate aminotransferase (AST) in B16 tumor bearing mice to the levels of non-challenged normal mice (FIG. 26). These results demonstrate that CC could be used effectively in reducing toxicities of therapeutic and checkpoint inhibitor antibodies or a therapeutic treatment.

Figure 27:
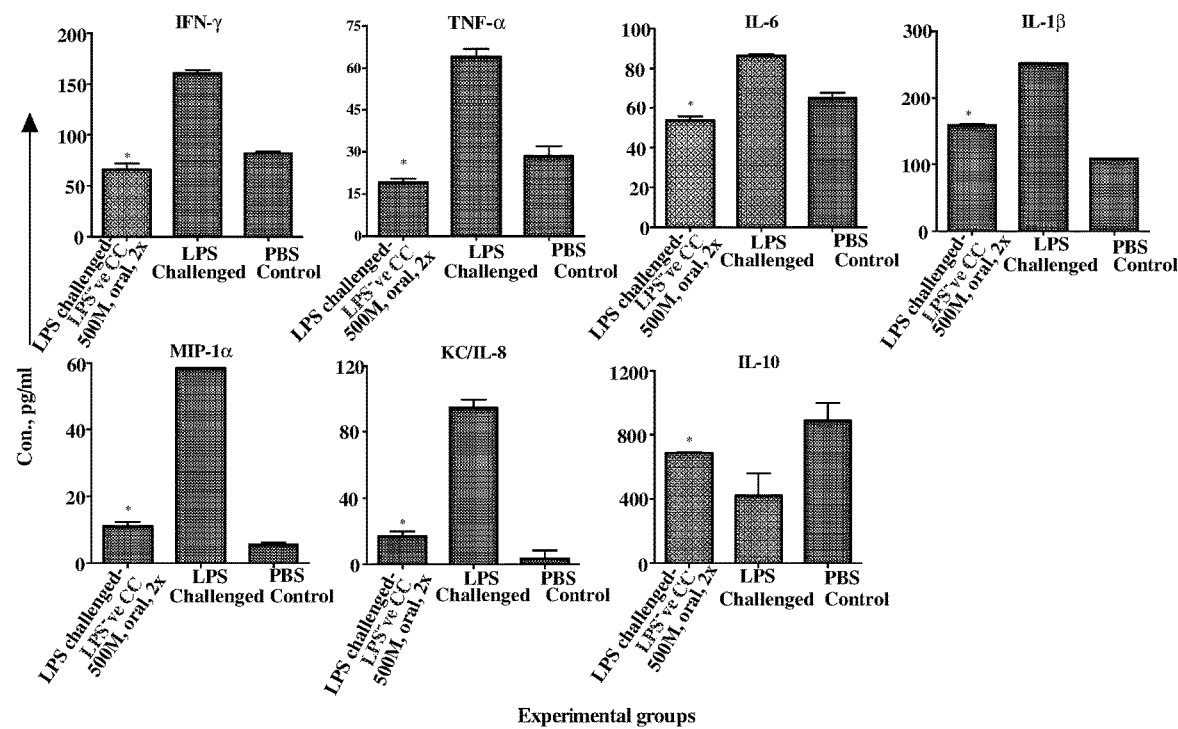
FIG. 27 demonstrates the modulation of IFN-γ, TNF-α, IL-6, IL-1β, MIP-1α, IL-8 and IL-10 in liver homogenate samples from LPS$^{-ve}$ CC and PBS treated mice orally post 2 and 24 hrs in vivo challenge with LPS at 25 mg/Kg, i.p. Data are expressed in pg/ml and represent average±SD of triplicate wells.

Example 22: LPS Negative *Caulobacter crescentus* ($LPS^{-ve}$ CC) Protects Mice from Liver Damage in LPS Challenged Model of Sepsis/Inflammation: Modulation of Cytokine Levels in Liver To determine the role of lipopolysaccharide negative ($LPS^{-ve}$) CC in immune modulation, C57/bl6 female mice were challenged with LPS at 25 mg/Kg in 200 µl saline intraperitonially and treated orally with $LPS^{-ve}$ CC ($500 \times 10^6$ CFU/mouse) post 2 and 20 h in vivo challenge with LPS. Healthy unchallenged and PBS fed mice were also included as controls. Mice were euthanized after 24 h of the second treatment, and liver was harvested followed by determining cytokines in their homogenates. LPS challenged mice had high levels of inflammatory cytokines and chemokines in liver homogenate. In contrast, $LPS^{-ve}$ CC treatment down-regulated production of inflammatory cytokines IFN-γ, TNF-α, IL-1β, IL-6, IL-8/KC, and chemokine MIP-1α and up-regulated the production of anti-inflammatory cytokine IL-10 (FIG. 27). These results demonstrate that $LPS^{-ve}$ CC also exhibits positive effect in controlling inflammatory processes, similar to those obtained using wild-type CC. Therefore, LPS negative CC can be utilized in controlling inflammatory processes and normalizing tissue functions including post-inflammatory medical conditions.

Figure 28:
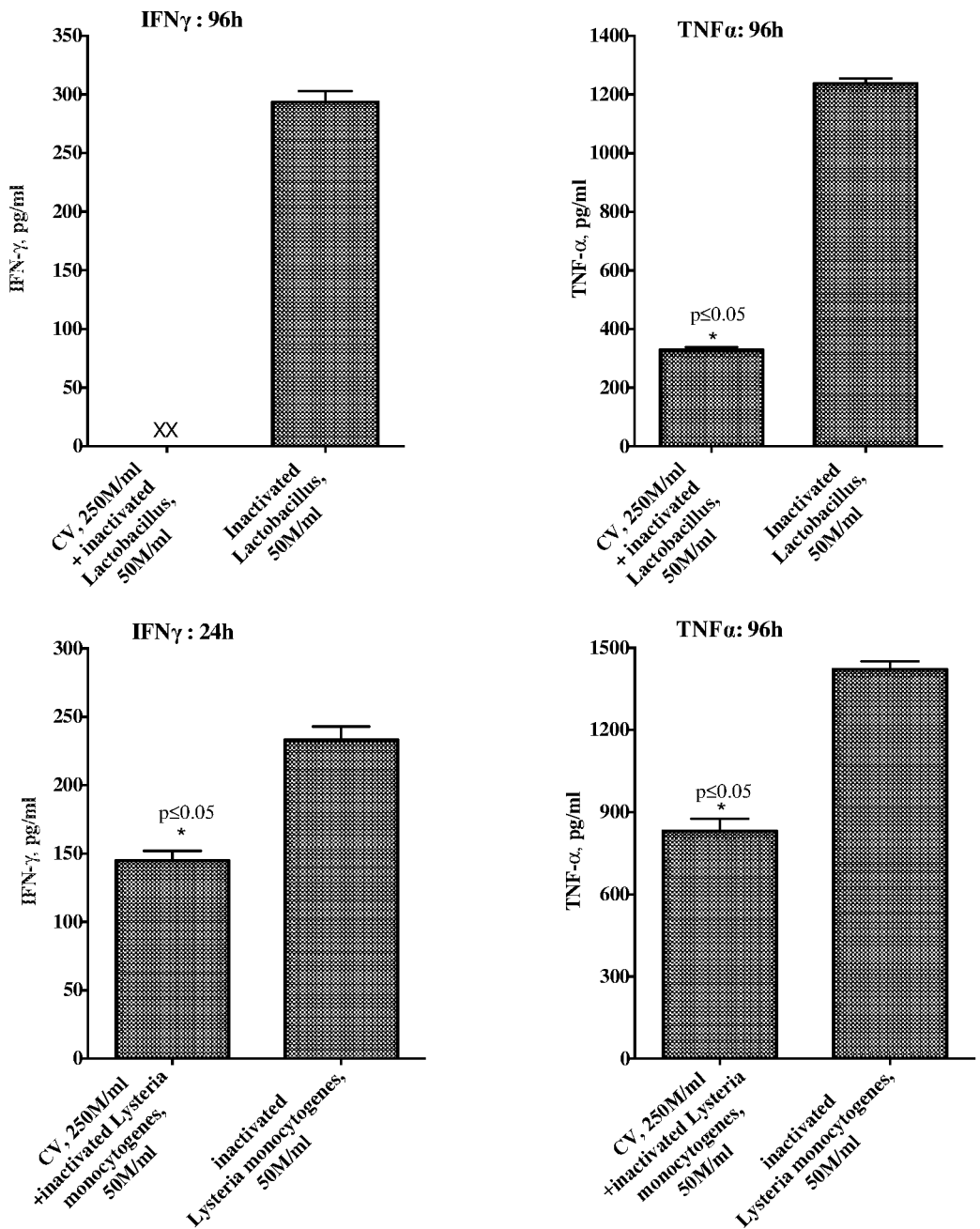
FIG. 28 demonstrates that *Caulobacter vibroides* (CV) can lead to down regulation of inflammatory cytokines (IFN-γ and TNF-α) induced by a probiotic (*Lactobacillus rhamnosus*, LB) or a pathogenic bacterium (*Lysteria monocytogenes*, LM) from human PBMCs in cell cultures. Data are expressed in pg/ml and represent average+SD of triplicate wells.

Example 23: Effect of *Caulobacter vibroides* (CV) in Reducing Pro-Inflammatory Cytokines Induced by a Probiotic or Pathogenic Bacteria in Human PBMCs Human PBMCs ($4 \times 10^6$/well) were stimulated with inactivated *Lactobacillus rhamnosus* (LB) or *Lysteria monocytogenes* (LM) ($50 \times 10^6$ CFU/ml) for 6 h. After that CV ($250 \times 10^6$ CFU/ml) was added and plates were incubated for additional 24 or 96 h. Culture supernatants were collected and assayed for IFN-γ and TNF-α by ELISA. Treatment with CV reduced the levels of IFN-γ and TNF-α induced by LB and LM (FIG. 28). These results suggest that other species of *Caulobacter* can reduce the inflammation related to bacterial or viral pathogens. These results also suggest that *Caulobacter* species can be used to treat undesirable inflammatory responses induced by microbiome related and unrelated microbes. Further, they can be used to modulate immunomodulatory activity of a microbiome therapeutic.

Figure 29:
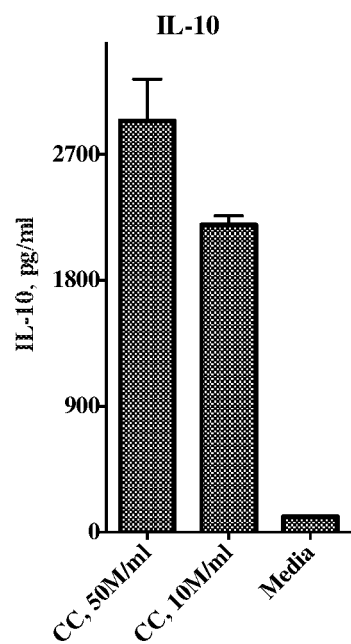
FIG. 29 shows that CC induces IL-10 production from human myeloid dendritic cells (DCs) cultured ex vivo. Data are expressed in pg/ml and represent average±SD of triplicate wells.

Example 24: Effect of *Caulobacter* Cescentus (CC) in Ex Vivo Manipulation of Human Myeloid Dendritic Cells Human myeloid dendritic cells differentiated from peripheral blood monocytes ($2 \times 10^6$/ml) were cultured for 24 h in the absence and presence of CC (50 or 10 CFU/ml). Culture supernatants were collected and examined for IL-10 levels by ELISA. The results obtained suggest that CC can generate a population of modulated DCs producing IL-10 (FIG. 29). Dendritic cells (DCs) are key regulators of adaptive immunity with the potential to induce T cell suppression and tolerance. IL-10 produced by DCs plays a role in generation, expansion and maintenance of regulatory T cells. These results suggest that CC can be used for ex vivo manipulation of DCs for DC-based immunotherapeutic strategies.

Example 25: Effect of *Caulobacter* Cescentus (CC) on Differentiation/Expansion of Pluripotent Stem Cells from Human PBMCs into Myeloid Cells Human PBMCs ($4 \times 10^6$/well) were cultured with CC ($500 \times 10^6$, $50 \times 10^6$, $10 \times 10^6$ and $1 \times 10^6$ CFU/ml) and saline for 10 days. PBMCs were stained for surface markers CD34, CD45, CD11c and CD11b. Cells were gated for CD34+ CD45-pluripotent stem cells, which were further gated for CD11c+ and CD11b+ DCs and macrophages, and data were analyzed by flow cytometry. The results obtained suggest that CC can differentiate stem cells into myeloid cells (FIG. 30). Myeloid cells originate from multipotent hematopoietic stem cells. These cells play a critical role in innate and adaptive immunity, inflammatory reaction, restoration of immune homeostasis, bone remodelling etc. Thus, CC can lead to differentiation and/or expansion of myeloid cells from stem cells for use in patient specific immunotherapy.

What is claimed is:

1. A method of preventing or treating a metabolic disease, disorder or condition in an individual, the method comprising administering to the individual an effective amount of an immunomodulatory composition, the immunomodulatory composition comprising:
   a) live *Caulobacter* spp.; and
   b) a pharmaceutically acceptable excipient;
   wherein the composition is administered via an oral, nasal, or topical route of administration;
   wherein the *Caulobacter* spp. is selected from the group consisting of *Caulobacter crescentus*, lipopolysaccharide-negative *Caulobacter crescentus*, S-layer-negative *Caulobacter crescentus*, *Caulobacter vibroides*, *Caulobacter subvibriodes*, *Caulobacter henricii*, *Caulobacter fusiformis*, and *Caulobacter intermedius*.

2. The method of claim 1, further comprising administering to the individual an additional therapeutic agent or antibody to treat the metabolic disease, disorder or condition.

3. The method of claim 1, further comprising administering to the individual an additional therapeutic agent or antibody to treat a cardiovascular disease, diabetes, dyslipidemia, hypertension, or inflammation.

4. The method of claim 1, further comprising administering to the individual a therapeutic microbe.

5. The method of claim 1, wherein the individual is a human, a non-human mammal, or a non-mammalian animal.

6. The method of claim 1, where the metabolic disease, disorder or condition is selected from the group consisting of insulin resistance, glucose metabolism disorder, glucose-intolerance, hypoglycemia, hypoinsulinemia, retinopathy, peripheral neuropathy, depression, anxiety, lipid metabolism disorder, dyslipidemia, hypercholesterolemia, peripheral vascular disease, hypertriglyceridemia, polycystic ovary syndrome, acne, muscular dystrophy, hypertension, cardiomyopathy, stroke, ischemia, myasthenia gravis, cardiovascular disease, fibromyalgia, anemia, chronic fatigue syndrome, metabolic syndrome, wounds, ulcers, oxidative stress, mitochondrial disease, mitochondrial dysfunction, epilepsy, neurodegenerative disease, chronic kidney disease and gout.

* * * * *